US009988674B2

(12) United States Patent
Joung et al.

(10) Patent No.: US 9,988,674 B2
(45) Date of Patent: Jun. 5, 2018

(54) FULL INTERROGATION OF NUCLEASE DSBS AND SEQUENCING (FIND-SEQ)

(71) Applicant: The General Hospital Corporation, Boston, MA (US)

(72) Inventors: J. Keith Joung, Winchester, MA (US); Shengdar Tsai, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days. days.

(21) Appl. No.: 15/262,972

(22) Filed: Sep. 12, 2016

(65) Prior Publication Data

US 2017/0073747 A1    Mar. 16, 2017

Related U.S. Application Data

(60) Provisional application No. 62/217,690, filed on Sep. 11, 2015.

(51) Int. Cl.
| | | |
|---|---|---|
| C12Q 1/68 | (2006.01) | |
| C12N 15/10 | (2006.01) | |
| C40B 50/06 | (2006.01) | |

(52) U.S. Cl.
CPC ....... C12Q 1/6855 (2013.01); C12N 15/1093 (2013.01); *C40B 50/06* (2013.01)

(58) Field of Classification Search
None
See application file for complete search history.

(56) References Cited

U.S. PATENT DOCUMENTS

| | | | |
|---|---|---|---|
| 7,803,550 | B2 | 9/2010 | Makarov et al. |
| 8,071,312 | B2 | 12/2011 | Makarov et al. |
| 8,399,199 | B2 | 3/2013 | Makarov et al. |
| 8,420,319 | B2 | 4/2013 | Mikawa |
| 8,728,737 | B2 | 5/2014 | Makarov et al. |
| 2006/0292611 | A1 | 12/2006 | Berka et al. |
| 2009/0082295 | A1 | 3/2009 | Jungnelius et al. |
| 2010/0317722 | A1 | 12/2010 | Lavon |
| 2011/0060493 | A1 | 3/2011 | Miura et al. |
| 2011/0287545 | A1 | 11/2011 | Cost |
| 2013/0137605 | A1 | 5/2013 | Shendure et al. |
| 2013/0143204 | A1 | 6/2013 | Von Kalle |
| 2013/0303461 | A1 | 11/2013 | Iafrate et al. |
| 2013/0309668 | A1 | 11/2013 | Makarov et al. |
| 2014/0024542 | A1 | 1/2014 | Richards |

(Continued)

FOREIGN PATENT DOCUMENTS

| | | |
|---|---|---|
| WO | WO 2012/065143 | 5/2012 |
| WO | WO 2013/078470 | 5/2013 |

(Continued)

OTHER PUBLICATIONS

'ncbi.nlm.nih.gov' [online]. "Homologs Are Descended from a Common Ancestor," 2002, [retrieved on Jan. 30, 2017]. Retrieved from the Internet: URL <https://www.ncbi.nlm.nih.gov/books/NBK22355/>. 1 page.

(Continued)

*Primary Examiner* — Kaijiang Zhang
(74) *Attorney, Agent, or Firm* — Fish & Richardson P.C.

(57) ABSTRACT

Sensitive, unbiased methods for genome-wide detection of potential off-target nuclease cleavage sites in DNA, e.g., in cell type-specific genomic DNA samples.

18 Claims, 17 Drawing Sheets

(14 of 17 Drawing Sheet(s) Filed in Color)

(56) References Cited

U.S. PATENT DOCUMENTS

2014/0295557 A1     10/2014    Joung et al.

FOREIGN PATENT DOCUMENTS

| WO | WO 2014/093701 | 6/2014 |
| --- | --- | --- |
| WO | WO 2015/200378 | 12/2015 |

OTHER PUBLICATIONS

'thermofisher.com' {online}. "PCR Methods-Top Ten Strategies," 2017, [retrieved on Feb. 1, 2017]. Retrieved from the Internet: URL <https://www.thermofisher.com/us/en/home/life-science/cloning/cloning-learningcenter/invitrogen-school-of-molecular-biology/per-education/per-reagents-enzymes/per-methods.html>. 10 pages.
International Search Report and Written Opinion in International Application No. PCT/US16/51097, dated Jan. 24, 2017, 12 pages.
International Search Report and Written Opinion in International Application No. PCT/US16/54912, dated Jan. 24, 2017, 12 pages.
Mullis and Faloona, "Specific synthesis of DNA in vitro via a polymerase-catalyzed chain reaction," Methods in Enzymology, 1987, 155: 335-350.
Office Action in U.S. Appl. No. 15/192,753, dated Feb. 9, 2017, 43 pages.
Bolukbasi et al., "Creating and evaluating accurate CRISPR-Cas9 scalpels for genomic surgery," Nat Meth, Jan. 2016, 13: 41-50.
Cencic et al., "Protospacer Adjacent Motif (PAM)-Distal Sequences Engage CRISPR Cas9 DNA Target Cleavage," Oct. 2014, PLOS One, 9(10): e109213.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choi & Meyerson, "Targeted genomic rearrangements using CRISPR/Cas technology," Nat Commun., Apr. 24, 2014, 5:3728, doi: 10.1038/ncomms4728.
Cong et al., "Multiplex genome engineering using CRISPR/Cas systems," Science, 2013, 339:819-823 (Author Manuscript).
Cox et al., "Therapeutic genome editing: prospects and challenges," Nat Med, 2015, 21:121-131.
Cradick et al., "CRISPR/Cas9 systems targeting beta-globin and CCR5 genes have substantial off-target activity," Nucleic Acids Res., 2013, 41(20):9584-92.
Crosetto et al, "Nucleotide-resolution DNA double-strand break mapping by next-generation sequencing," Apr. 2013, Nat Methods 10(4): 361-365.
DiCarlo et al., "Genome engineering in *Saccharomyces cerevisiae* using CRISPR-Cas systems," Nucleic Acids Res, 2013, 41(7):4336.
Duan et al., "Genome-wide identification of CRISPR/Cas9 off-targets in human genome," Cell Res, 2014, 24(8):1009-1012.
Fonfara et al., "Phylogeny of Cas9 determines functional exchangeability of dual-RNA and Cas9 among orthologous type II CRISPR-Cas systems," 2014, Nucleic Acids Res 42(4): 2577-2590.
Frock et al., "Genome-wide detection of DNA double-stranded breaks induced by engineered nucleases," Nat Biotechnol, Feb. 2015, 33: 179-186.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat Biotechnol, Mar. 2014, 32(3): 279-284.
Gabriel et al., "An unbiased genome-wide analysis of zinc-finger nuclease specificity," Nat Biotechnol, Sep. 2011, 29(9): 816-823.
Gaj et al., "ZFN, TALEN and CRISPR/Cas-based methods for genome engineering," Trends Biotechnol,, Jul. 2013, 31(7):397-405.
Ghezraoui et al., "Chromosomal translocations in human cells are generated by canonical nonhomologous end-joining," Mol Cell, Sep. 18, 2014, 55: 829-842.
Gnirke et al., "Solution hybrid selection with ultra-long oligonucleotides for massively parallel targeted sequencing," Nature Biotechnology, 2009, 27: 182-189.
Gori et al., "Delivery and Specificity of CRISPR-Cas9 Genome Editing Technologies for Human Gene Therapy," Hum Gene Ther, 2015, 26: 443-451.
Gostissa et al., "IgH class switching exploits a general property of two DNA breaks to be joined in cis over long chromosomal distances," Proc Natl Acad Sci, Feb. 18, 2014, 111(7): 2644-2649.
Guilinger et al., "Fusion of catalytically inactive Cas9 to FokI nuclease improves the specificity of genome modification," Nat Biotechnol, Jun. 2014, 32(6): 577-582.
Heigwer et al., "E-CRISP: fast CRISPR target site identification," Nat Methods, Feb. 2014, 11: 122-123.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Hwang et al., "Efficient In Vivo Genome Editing Using RNA-Guided Nucleases," Nat Biotechnol., 2013, 31:227-229 (Author Manuscript).
International Search Report and Written Opinion in International Application No. PCT/US15/37269, dated Oct. 15, 2015, 26 pages.
Jiang et al., "Characterization of *Escherichia coli* Endonuclease VIII," J. Biol. Chem, 1997, 272:32230-32239.
Jiang et al., "CRISPR-assisted editing of bacterial genomes," Nat Biotechnol, Mar. 2013, 31(3): 233-239.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Kim et al., "Digenome-seq: genome-wide profiling of CRISPR-Cas9 off-target effects in human cells," Nat Meth, Mar. 2015, 12: 237-243.
Kim et al., "Genome-wide target specificities of CRISPR-Cas9 nucleases revealed by multiplex Digenome-seq.," Genome Res, 2016, 26: 406-415.
Kuscu et al., "Genome-wide analysis reveals characteristics of off-target sites bound by the Cas9 endonuclease," Nat Biotechnol, Jul. 2014, 32 (7): 677-683.
Lin et al., "CRISPR/Cas9 systems have off-target activity with insertions or deletions between target DNA and guide RNA sequences," Nucleic Acids Res, 2014, 42(11): 7473-7485.
Lindahl, "DNA repair enzymes," Annu. Rev. Biochem, 1982, 51:61-64.
Lindhal et al., "DNA N-glycosidases: properties of uracil-DNA glycosidase from *Escherichia coli*," J. Biol. Chem., May 1977, 252:3286-3294.
Mali et al, "CAS9 transcriptional activators for target specificity screening and paired nickases for cooperative genome engineering," Nat Biotechnol, Sep. 2013, 31(9): 833-838.
Mali et al., "RNA-guided human genome engineering via Cas9," Science, Feb. 2013, 339:823-826 (Author Manuscript).
Marx et al., "Gene editing: how to stay on-target with CRISPR," Nat Methods, 2014, 11:1021-1026.
Melamede et al., "Isolation and characterization of endonuclease VIII from *Escherichia coli*," Biochemistry, Feb. 1994, 33:1255-1264.
Ochman et al., Genetic Applications of an Inverse Polymerase Chain Reaction, Genetics, Nov. 1998, 120: 621-623.
Orlando et al., "Zinc-finger nuclease-driven targeted integration into mammalian genomes using donors with limited chromosomal homology," Nucleic Acids Res, 2010, 38(15): e152.
Osborn et al., "TALEN-based gene correction for epidermolysis bullosa," 2013, Mol Ther, 21: 1151-1159.
Pattanayak et al., "High-throughput profiling of off-target DNA cleavage reveals RNA-programmed Cas9 nuclease specificity," Nat Biotechnol., 2013, 31:839-843 (Author Manuscript).

(56) References Cited

OTHER PUBLICATIONS

Ran et al., "Double nicking by RNA-guided CRISPR Cas9 for enhanced genome editing specificity," Cell, Sep. 2013, 154: 1380-1389.

Ran et al., "Genome engineering using the CRISPR-Cas9 system," Nat Protoc, Nov. 2013, 8(11): 2281-2308.

Ran et al., "In vivo genome editing using *Staphylococcus aureus* Cas9," Nature, Apr. 2015, 520, 186-191.

Sander and Joung et al., "CRISPR-Cas systems for editing, regulating and targeting genomes," Nat Biotechnol., Apr. 2014, 32(4):347-55.

Sander et al., "In silico abstraction of zinc finger nuclease cleavage profiles reveals an expanded landscape of off-target sites," Nucleic Acids Res, Oct. 2013, 41(19): e181.

Schmidt et al., "High-resolution insertion-site analysis by linear amplification-mediated PCR (LAM-PCR)," Nat Methods, Dec. 2007, 4(12): 1051-1057.

Shen et al., "Generation of gene-modified mice via Cas9/RNA-mediated gene targeting," Cell Res, 2013, 23:720-723.

Smith et al, "Whole-genome sequencing analysis reveals high specificity of CRISPR/Cas9 and TALEN-based genome editing in human iPSCs," Cell Stem Cell, Jul. 3, 2014, 15(1):12-13.

Tsai and Joung, "Defining and improving the genome-wide specificities of CRISPR-Cas9 nucleases," Nature, Apr. 2016, 17: 300-312.

Tsai et al., "Dimeric CRISPR RNA-guided FokI nucleases for highly specific genome editing," Nat Biotechnol, Jun. 2014, 32(6): 569-576.

Tsai et al., "GUIDE-seq Enables Genome-Wide Profiling of Off-Target Cleavage by CRISPR-Cas Nucleases," Nature Biotechnology, Dec. 2014, 187-197.

Tsai et al., "What's changed with genome editing?," Jul. 2014, Cell Stem Cell, 15(1): 3-4.

Veres et al., "Low incidence of off-target mutations in individual CRISPR-Cas9 and TALEN targeted human stem cell clones detected by whole-genome sequencing," Cell Stem Cell, Jul. 3, 2014, 15: 27-30.

Wu et al., "Genome-wide binding of the CRISPR endonuclease Cas9 in mammalian cells," Nat Biotechnol. Jul. 2014; 32(7):670-6.

Yang et al., "Targeted and genome-wide sequencing reveal single nucleotide variations impacting specificity of Cas9 in human stem cells," Nature Communications, Nov. 2014, 5: 5507.

Zheng et al., "Anchored multiplex PCR for targeted next-generation sequencing," Nat Med, Nov. 10, 2014, 20(12): 1479-1484.

Cameron et al., "Mapping the genomic landscape of CRISPR—Cas9 cleavage," Nature Methods, 2017, 10 pages.

Canela et al., "DNA Breaks and End Resection Measured Genomewide by End Sequencing," Molecular Cell, 2016, 63: 1-14.

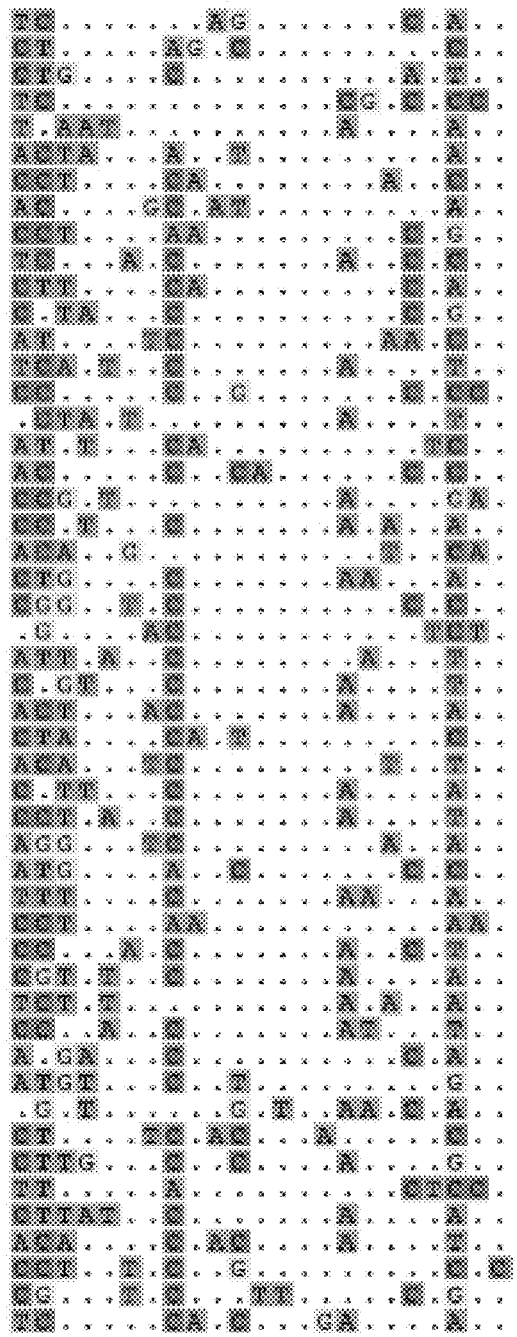
FIG. 3C, Continued

FIG. 5C

FULL INTERROGATION OF NUCLEASE DSBS AND SEQUENCING (FIND-SEQ)

CLAIM OF PRIORITY

This application claims priority under 35 USC § 119(e) to U.S. Patent Application Ser. No. 62/217,690, filed on Sep. 11, 2015. The entire contents of the foregoing are hereby incorporated by reference.

SEQUENCE LISTING

The instant application contains a Sequence Listing which has been submitted electronically in ASCII format and is hereby incorporated by reference in its entirety. Said ASCII copy, created on Nov. 23, 2016, is named 29539-019001 SL.TXT and is 198,150 bytes in size.

FEDERALLY SPONSORED RESEARCH OR DEVELOPMENT

This invention was made with Government support under Grant No. DP1 GM105378 awarded by the National Institutes of Health. The Government has certain rights in the invention.

TECHNICAL FIELD

Described herein are in vitro methods for defining the genome-wide cleavage specificities of engineered nucleases such as CRISPR-Cas9 Nucleases.

BACKGROUND

Engineered nuclease technology including zinc fingers, TALENs, and CRISPR-Cas9 nucleases, is revolutionizing biomedical research and providing important new modalities for therapy of gene-based diseases.

SUMMARY

At least in part, the present invention is based on the development of sensitive, unbiased methods for genome-wide detection of potential engineered nuclease (e.g., CRISPR-Cas9) off-target cleavage sites from cell type-specific genomic DNA samples. The present methods use exonuclease selection of covalently closed DNA molecules to create a population of genomic DNA molecules with very few free DNA ends, as a starting population for cleavage-specific enrichment and sequencing. Enrichment of these cleaved fragments, estimated to be >20,000× from human genomic DNA, enables very sequencing-efficient discovery of in vitro cleaved DNA fragments, in contrast to methods such as Digenome-Seq (Kim et al., Nat Methods. 2015 March; 12(3):237-43) that rely on whole-genome sequencing. After optimization, the present in vitro assay detected 100% of off-target cleavage sites detected by the in-cell GUIDE-seq assay at the VEGFA site target site used as a test case and described in Tsai et al., Nat Biotechnol. 2015 February; 33(2):187-97 (in other words, the present in vitro assay detects a superset of GUIDE-seq detected cleavage sites).

Described herein are methods of enzymatically preparing a library of DNA fragments without DNA double-stranded breaks (DSBs) (the terms "breaks" and "cleavage" are used herein interchangeably) by ligation of stem-loop or hairpin adapters followed by exonuclease selection, and for detecting nuclease-induced cleavage of this enzymatically purified library of covalently closed DNA fragments by sequencing. Together, these two methods comprise a strategy for efficiently mining for nuclease-induced cleavage sites in complex mixtures of DNA. Thus the methods can include creating a population of molecules without ends, treating that population with a nuclease, and finding molecules in this population that have newly created ends as a result of nuclease-induced cleavage.

In a first aspect, the invention provides methods for preparing a library of covalently closed DNA fragments. The methods include providing DNA, e.g., gDNA from a cell type or organism of interest; optionally randomly shearing the DNA to a defined average length, e.g., an average length of about 200-1000 bps, e.g., about 500 bps, to provide a population of DNA fragments; preparing the fragments for end-ligation, e.g., by end-repairing and then A-tailing the sheared DNA; ligating a first hairpin adapter comprising at least a single deoxyuridine (uracil) and a first primer site compatible for use in PCR priming and/or sequencing, e.g., next generation sequencing (NGS) to the ends of the fragments, to prepare a population of ligated fragments; contacting the ligated fragments with a nuclease that induces double stranded breaks; and purifying the ligated fragments using an exonuclease, thereby preparing a library of covalently closed DNA fragments.

The methods can also include contacting the library of covalently closed DNA fragments with a nuclease to induce site-specific cleavage; ligating a second hairpin adapter comprising at least a single deoxyuridine and a second primer site compatible for use with the first primer site in PCR priming and/or sequencing; contacting the library with an enzyme, e.g., uracil DNA glycosylase (UDG) and/or endonuclease VIII, a DNA glycosylase-lyase, to nick the DNA at the deoxyuridine; and sequencing those fragments having a first and second hairpin adapter.

Also provided herein are methods for preparing a library of fragments comprising nuclease-induced double stranded breaks in DNA, e.g., genomic DNA (gDNA). The methods can include providing DNA, e.g., gDNA from a cell type or organism of interest; randomly shearing the DNA to a defined average length, e.g., an average length of about 200-1000 bps, e.g., about 100-500 bps; optionally end-repairing and then A-tailing the sheared DNA; ligating a first single-tailed hairpin adapter, preferably comprising a first region, e.g., of about 10-20, e.g., 12 nucleotides; a second region, e.g., of about 45-65, e.g., 58 nucleotides, that forms one or more hairpin loops and comprises a first primer site compatible for use in PCR priming and/or sequencing, e.g., next generation sequencing (NGS); and a third region, e.g., of about 10-20, e.g., 13 nucleotides (e.g., one longer than the first region) that is complementary to the first region, with a single deoxyuridine nucleotide between the first and second regions; contacting the sample with one or more exonucleases (e.g., bacteriophage lambda exonuclease, E. coli ExoI, PlasmidSafe™ ATP-dependent exonuclease), sufficient to degrade any DNA molecules that lack the first (e.g., 5') single-tailed hairpin adapter ligated to both of their ends; treating the sample with a nuclease to induce site-specific cleavage (e.g., of on- and/or off-target sites, e.g., to induce blunt or staggered/overhanging ends) optionally end-repairing and then A-tailing the resulting ends; ligating a second (e.g., 3') single-tailed hairpin adapter comprising a first region of about 10-20, e.g., 15 nucleotides; a second region of about 40-60, e.g., 48, nucleotides that forms one or more hairpin loops and comprises a second primer compatible for use with the first primer site in PCR priming and/or sequencing, e.g., next generation sequencing (NGS); and a third region of about 10-20, e.g., 16 nucleotides (e.g., one longer than the first region) that is complementary to the first region and that also contains a single deoxyuridine nucleotide between the second and third regions, to create a population wherein the DNA fragments that were cleaved by the nuclease have a first and second single-tailed hairpin adapter ligated to their respective ends; thereby preparing a library of fragments, e.g., wherein one end was created by a nuclease-induced double stranded break in the DNA.

In some embodiments, the methods include contacting the library with uracil DNA glycosylase (UDG) and/or endonuclease VIII, a DNA glycosylase-lyase to nick the DNA at the deoxyuridine; and sequencing those fragments bearing a first and a second hairpin adapter.

Also provided herein are methods for detecting nuclease-induced double stranded breaks (DSBs) in DNA, e.g., in genomic DNA (gDNA) of a cell. The methods include providing DNA, e.g., gDNA from a cell type or organism of interest; randomly shearing the DNA to a defined average length, e.g., an average length of about 200-1000 bps, e.g., about 500 bps; optionally end-repairing and then A-tailing the sheared DNA; ligating a first single-tailed hairpin adapter, preferably comprising a first region, e.g., of about 10-20, e.g., 12 nucleotides; a second region, e.g., of about 45-65, e.g., 58 nucleotides, that forms one or more hairpin loops and comprises a first primer site compatible for use in PCR priming and/or sequencing, e.g., next generation sequencing (NGS); and a third region, e.g., of about 10-20, e.g., 13 nucleotides (e.g., one longer than the first region) that is complementary to the first region, with a single deoxyuridine nucleotide between the first and second regions; contacting the sample with one or more exonucleases (e.g., *bacteriophage lambda* exonuclease, *E. coli* ExoI, PlasmidSafe™ ATP-dependent exonuclease), sufficient to degrade any DNA molecules that lack the first single-tailed hairpin adapter ligated to both of their ends; treating the sample with a nuclease to induce site-specific cleavage the DNA, e.g., to produce on- and/or off-target cleavage sites; optionally end-repairing and then A-tailing the resulting cleaved ends; ligating a second (e.g., 3') single-tailed hairpin adapter comprising a first region of about 10-20, e.g., 15 nucleotides; a second region of about 40-60, e.g., 48, nucleotides that forms one or more hairpin loops and comprises a second primer compatible for use with the first primer site in PCR priming and/or sequencing, e.g., next generation sequencing (NGS); and a third region of about 10-20, e.g., 16 nucleotides (e.g., one longer than the first region) that is complementary to the first region, and that also contains a single deoxyuridine nucleotide between the second and third regions, to create a population wherein the DNA fragments that were cleaved by the nuclease have the first and second hairpin adapters ligated to their respective ends; thereby preparing a library of fragments comprising nuclease-induced double stranded breaks in the DNA, e.g., wherein one end was created by a nuclease-induced double stranded break in the DNA; contacting the library with uracil DNA glycosylase (UDG) and/or endonuclease VIII, a DNA glycosylase-lyase to nick the DNA at the deoxyuridine; and sequencing those fragments bearing a first and a second hairpin adapter; thereby detecting DSBs induced by the nuclease.

In some embodiments, the engineered nuclease is selected from the group consisting of meganucleases, MegaTALs, zinc-finger nucleases, transcription activator effector-like nucleases (TALEN), and Clustered Regularly Interspaced Short Palindromic Repeats (CRISPR)/Cas RNA-guided nucleases (CRISPR/Cas RGNs).

In some embodiments, treating the sample with a nuclease to induce site-specific cleavage, e.g., at on- and off-target sites, comprises contacting the sample with a Cas9 nuclease complexed with a specific guide RNA (gRNA).

Further, provided herein are methods for determining which of a plurality of guide RNAs is most specific, i.e., induces the fewest off-target DSBs. The methods include, for each of the plurality of guide RNAs: providing gDNA from a cell type or organism of interest; randomly shearing the gDNA to a defined average length, e.g., an average length of about 200-1000 bps, e.g., about 500 bps; optionally end-repairing and then A-tailing the sheared gDNA; ligating a first single-tailed hairpin adapter, preferably comprising a first region, e.g., of about 10-20, e.g., 12 nucleotides; a second region, e.g., of about 45-65, e.g., 58 nucleotides, that forms one or more hairpin loops and comprises a first primer site compatible for use in PCR priming and/or sequencing, e.g., next generation sequencing (NGS); and a third region, e.g., of about 10-20, e.g., 13 nucleotides (e.g., one longer than the first region) that is complementary to the first region, with a single deoxyuridine nucleotide between the first and second regions; contacting the sample with one or more exonucleases (e.g., *bacteriophage lambda* exonuclease, *E. coli* ExoI, PlasmidSafe™ ATP-dependent exonuclease), sufficient to degrade any DNA molecules that lack the first hairpin adapter ligated to both of their ends; treating the sample with a Cas9 nuclease compatible with the guide RNA to induce site-specific cleavage (e.g., of on- and/or off-target sites, e.g., to produce blunt or staggered/overhanging ends); optionally end-repairing and then A-tailing the resulting cleaved ends; ligating a second (e.g., 3') single-tailed hairpin adapter comprising a first region of about 10-20, e.g., 15 nucleotides; a second region of about 40-60, e.g., 48, nucleotides that forms one or more hairpin loops and comprises a second primer compatible for use with the first primer site in PCR priming and/or sequencing, e.g., next generation sequencing (NGS); and a third region of about 10-20, e.g., 16 nucleotides (e.g., one longer than the first region) that is complementary to the first region, and that also contains a single deoxyuridine nucleotide between the second and third regions, to create a population wherein the DNA fragments that have a first and second hairpin adapter ligated to their ends are those that were cleaved by the nuclease; thereby preparing a library of fragments comprising nuclease-induced double stranded breaks in DNA, e.g., wherein one end was created by a nuclease-induced double stranded break in the DNA; contacting the library with uracil DNA glycosylase (UDG) and/or endonuclease VIII, a DNA glycosylase-lyase to nick the DNA at the deoxyuridine; and sequencing those fragments bearing a first and a second hairpin adapter, thereby detecting DSBs induced by the nuclease in each sample; optionally identifying whether each DSB is on-target or off-target; comparing the DSBs induced by the nuclease in each sample; and determining which of the plurality of guide RNAs induced the fewest off-target DSBs.

In some embodiments, the DNA is isolated from a mammalian, plant, bacterial, or fungal cell (e.g., gDNA).

In some embodiments, the DNA is synthetic.

In some embodiments, the engineered nuclease is a TALEN, zinc finger, meganuclease, megaTAL, or a Cas9 nuclease.

In some embodiments, the engineered nuclease is a Cas9 nuclease, and the method also includes expressing in the cells a guide RNA that directs the Cas9 nuclease to a target sequence in the genome.

In some embodiments, the primer site in the first or second hairpin adapter comprises a next generation sequencing primer site, a randomized DNA barcode or unique molecular identifier (UMI).

The present methods have several advantages. For example, the present methods are in vitro; in contrast, GUIDE-seq is cell-based, requiring the introduction of double stranded oligodeoxynucleotides (dsODN) as well as expression or introduction of nuclease or nuclease-encoding components into cells. Not all cells will allow the introduction of dsODNs and/or nuclease or nuclease-encoding components, and these reagents can be toxic in some cases. If a cell type of particular interest is not amenable to introduction of dsODNs, nucleases, or nuclease-encoding components, a surrogate cell type might be used, but cell-specific effects might not be detected. The present methods do not require delivery of the dsODN, nuclease, or nuclease-encoding components into a cell, are not influenced by chromatin state, do not create toxicity issues, and enable interrogation of specific cellular genomes by cleavage of genomic DNA that is obtained from the cell-type of interest.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

Figure 5C:
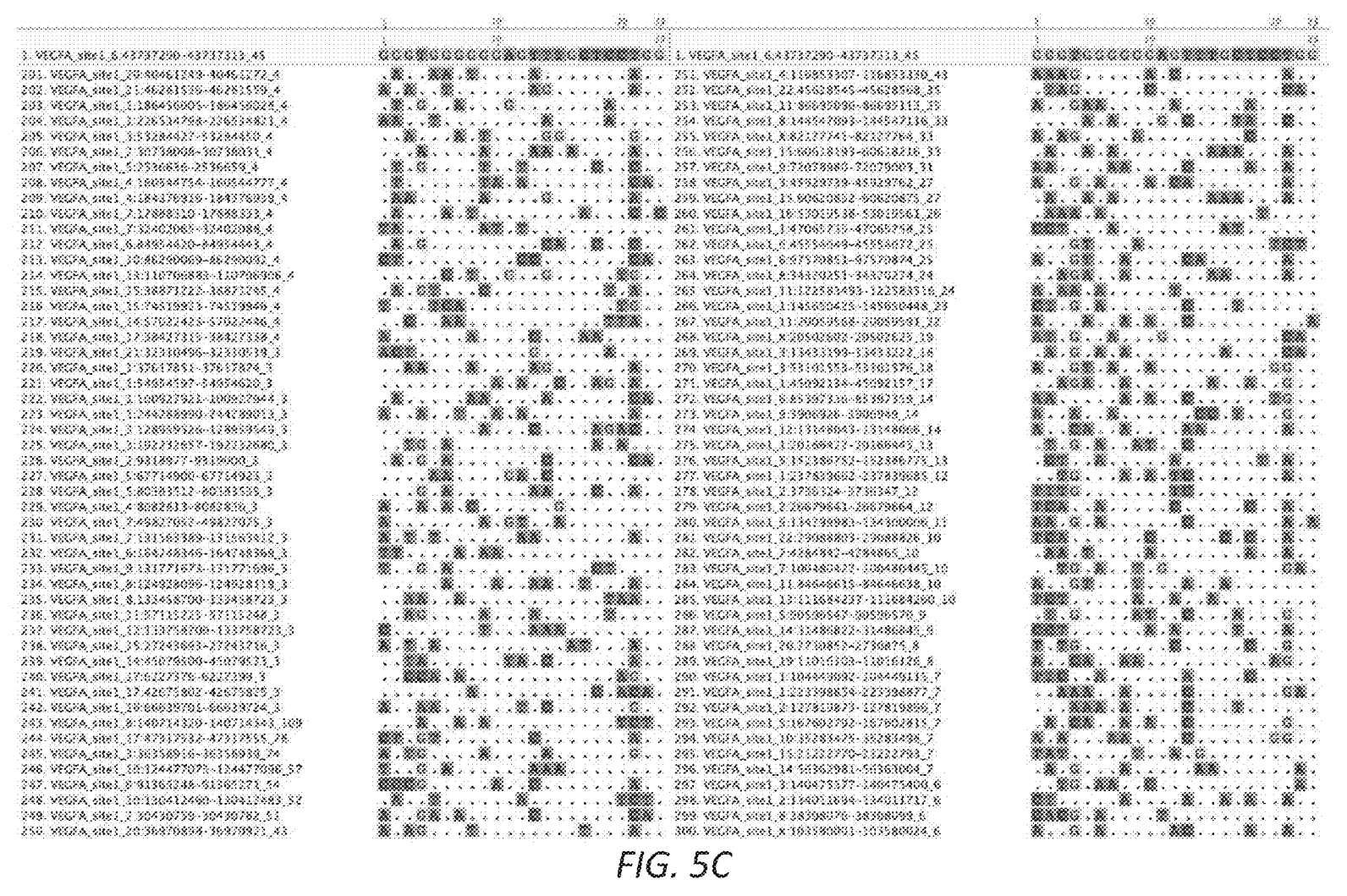

FIGS. 5A-D. Alignments of off-target sites detected by FIND-seq genomic in vitro cleavage assay for VEGFA site 1 based on combined higher-coverage depth sequencing data (SEQ ID NOS 390-439, 390, 440-489, 390, 490-539, 390, 540-589, 390, 590-639, 390, 640-689, 390, 690-739, 390 and 740-766, respectively, in order of appearance). Mismatched positions in the off-target cleavage sites relative to the intended site are indicated by bases highlighted with colored rectangles; matched positions are indicated by dots.

DETAILED DESCRIPTION

An important consideration for the therapeutic deployment of CRISPR-Cas9 nucleases is having robust, comprehensive, unbiased, and highly sensitive methods for defining their off-target effects. Recently, a number of methods for defining the genome-wide off-target effects of CRISPR-Cas9 and other customizable nucleases have been described. For example, the GUIDE-seq method, which relies on uptake of a short double-stranded oligonucleotide "tag" into nuclease-induced DSBs in living cells, has been shown to define off-target sites on a genome-wide scale, identifying sites that are mutagenized with frequencies as low as 0.1% of the time in a population of cells (Tsai et al., Nat Biotechnol. 2015). Other cell-based methods for defining nuclease-induced off-target breaks include a method that maps translocation fusions to the on-target site and another that relies on uptake of integration-deficient lentivirus (IDLV) genomes into sites of DSBs.

Despite this recent progress, cell-based methods for off-target determination have a number of limitations including: (1) a requirement to be able to introduce both the nuclease components and a tag such as the dsODN or IDLV genome into cells; (2) biological selection pressures that might favor or disfavor the growth of cells harboring certain types of off-target mutations; and/or (3) the potential confounding effects of cell-type-specific parameters such as chromatin, DNA methylation, gene expression, and nuclear architecture on nuclease off-target activities/effects.

In vitro methods using purified genomic DNA provide an attractive alternative because they would sidestep these various limitations of cell-based approaches. However, in vitro methods face the challenge that isolated genomic DNA is by experimental necessity randomly sheared (or broken) into smaller pieces. This poses a challenge because it is not easy to differentially identify DSBs induced by shearing from those induced by treatment of the genomic DNA in vitro by nucleases. The recently described Digenome attempted to use alignment of common ends induced by nucleases in genomic sequence but the signal for this type of event can be challenging to discern relative to the background of random DSBs from shearing of genomic DNA induced during genomic DNA isolation and by deliberate shearing of the DNA to smaller size pieces required for DNA sequencing methods. In addition, and perhaps more importantly, because there is no enrichment for the nuclease-induced DSBs, nearly all of the sequencing data generated with Digenome is just re-sequencing of random genomic DNA, a factor that further limits the sensitivity of the method since very few reads generated contribute the desired information about nuclease-induced DSBs. Indeed, Digenome failed to identify a number of off-target sites found by GUIDE-seq for a particular gRNA, although the caveat must be added that the two experiments were performed in different cell lines.

Figure 1A:
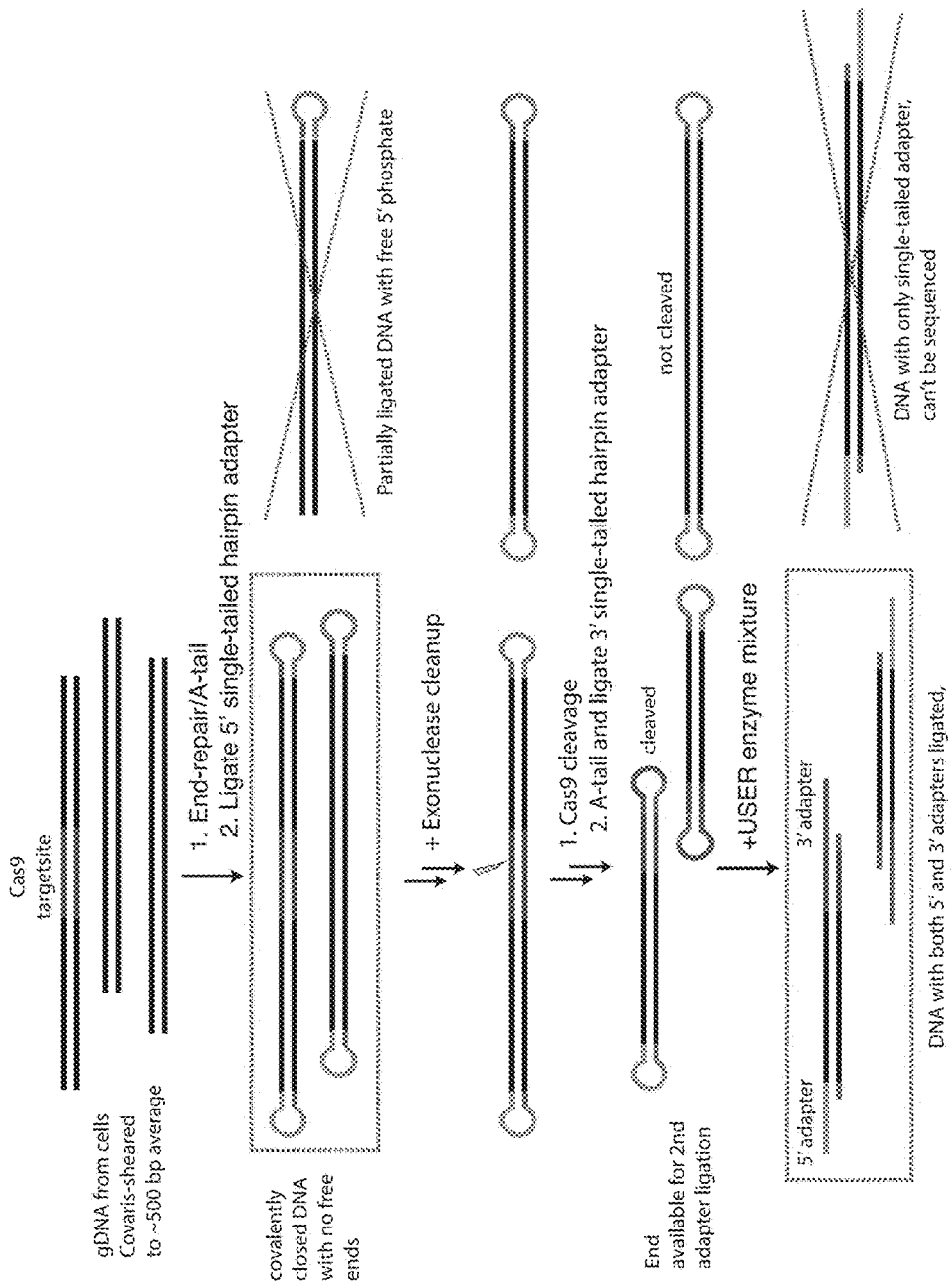
FIGS. 1A-B. Overview of an exemplary in vitro assay for genome-wide identification of CRISPR/Cas9 cleavage sites from complex mixtures of DNA called FIND-seq (Full Interrogation of Nuclease DSBs). (a) Genomic DNA is isolated from human cells and sheared to an average of ~500 bp using a Covaris S220 AFA instrument. Sheared DNA is end-repaired, A-tailed, and ligated with a 5' single-tailed hairpin adapter containing a single deoxyuradine. Successful ligation of the hairpin adapter to both ends of the DNA fragments will result in covalently closed DNA with no free end. Lambda Exonuclease and E. coli ExoI or PlasmidSafe ATP-dependent exonuclease can then be used to dramatically reduce the background of DNA with free ends, leaving a predominantly uniform population of covalently closed DNA molecules. Cas9 cleavage of adapter-ligated gDNA will produce ends with free 5' phosphates for the ligation of a second 3' single-tailed hairpin adapter that also contains a single uracil base. Treatment with USER enzyme mixture and PCR enriches for DNA molecules that have been ligated with both 5' and 3' single-tailed adapters. The use of single-tailed adapters reduces background, as only molecules that contain both 5' and 3' adapters can be amplified and sequenced. (b) Detailed schematic of adapter ligation steps, with sequence and predicted DNA secondary structure of hairpin adapters (SEQ ID NOS 1, 1, 1 and 9, respectively, in order of appearance). Ligation of hairpin adapters at both ends creates covalently closed DNA molecules that can be subsequently reopened at uracil-containing sites.
Figure 1B:
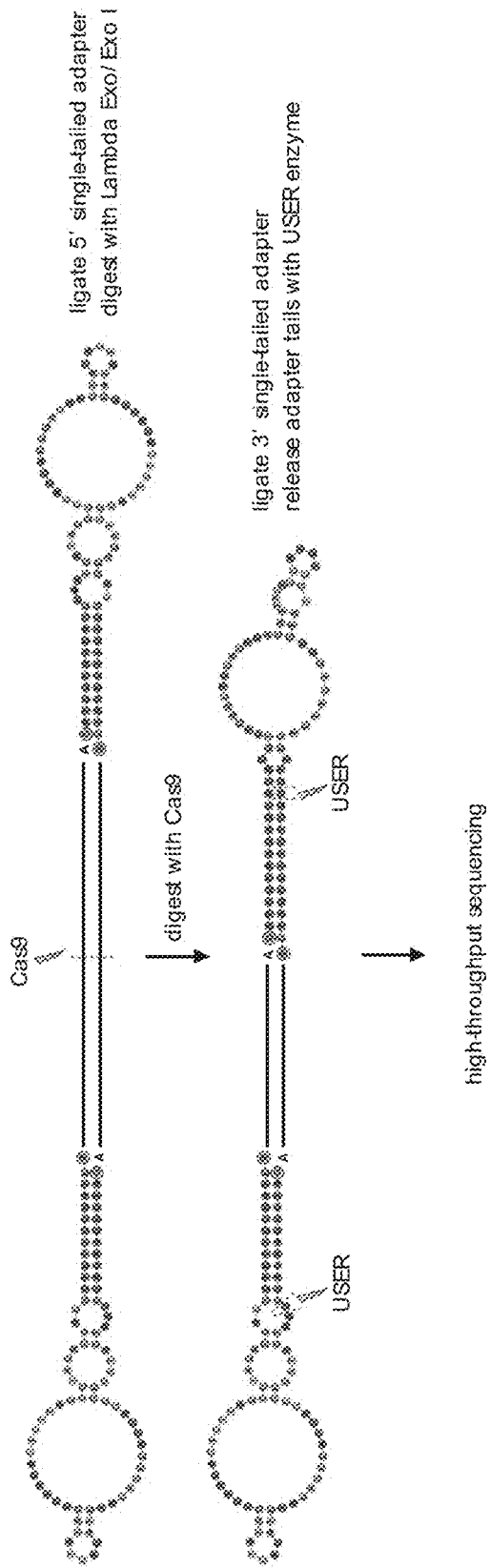

Described herein is an in vitro method that enables comprehensive determination of DSBs induced by nucleases on any genomic DNA of interest. This method enables enrichment of nuclease-induced DSBs over random DSBs induced by shearing of genomic DNA. An overview of how the method works can be found in FIGS. 1A and 1B. In brief, genomic DNA from a cell type or organism of interest is randomly sheared to a defined average length. In the present experiments, an average length of 500 bps worked well for subsequent next-generation sequencing steps; however, shorter or longer lengths can also be used. The random broken ends of this genomic DNA are end repaired (i.e., the random overhanging ends are filled in/blunted, e.g., using T4 polymerase, Klenow fragment, and T4 Polynucleotide Kinase (PNK)) and then A-tailed (i.e., an A (adenosine) is enzymatically added to the 3' end of a blunt, double-stranded DNA molecule). This then enables the ligation of a hairpin adapter, preferably bearing a 5' end next-generation sequencing primer site, that also contains a single deoxyuridine nucleotide at a specific position (FIG. 1B) and a 1-nucleotide (thymidine) overhang at the 3' end; hereafter this adapter is referred to as the "5' single-tailed hairpin adapter" or simply "5' hairpin adapter".

Following ligation of this adapter, the sample is then treated with one or more exonucleases (e.g., *bacteriophage lambda* exonuclease, *E. coli* ExoI, PlasmidSafe™ ATP-dependent exonuclease) that degrade any DNA molecules that have not had the 5' single-tailed hairpin adapter ligated to both of their ends. The collection of molecules is then treated to induce blunt-end cuts, e.g., with a Cas9 nuclease complexed with a specific guide RNA (gRNA). The resulting nuclease-induced blunt ends are A-tailed and then a second hairpin adapter bearing a 3' end next-generation sequencing primer site and that also contains a single deoxyuridine nucleotide at a specific position is ligated to these ends; this adapter is also referred to herein as the "3' single-tailed hairpin adapter" or simply "3' hairpin adapter".

As a result of these treatments, the only DNA fragments that should have a 5' and a 3' single-tailed hairpin adapter ligated to their ends are those that were cleaved by the nuclease. Following treatment (e.g., by the USER enzyme mixture) to nick DNA wherever a deoxyuridine is present, only those fragments bearing the two types of adapters can be sequenced.

The present methods can be used to prepare libraries of fragments for next generation sequencing, e.g., to identify guideRNA/Cas9 combinations that induce the most specific DSBs (e.g., that have the fewest off-target effects), e.g., for therapeutic or research purposes.

Single-Tailed Hairpin Adapters

The present methods include the use of non-naturally occurring 3' and 5' single-tailed hairpin adapters. The hairpin adapters include (from 5' to 3') a first region, e.g., of about 10-20, e.g., 12 or 15, nucleotides; a second region, e.g., of about 45-65, e.g., 58 or 48, nucleotides that forms one or more hairpin loops and includes a sequence compatible for use in PCR priming and/or sequencing, e.g., next generation sequencing (NGS); and a third region, e.g., of about 10-20, e.g., 13 or 16, nucleotides that is complementary to the first region. The lengths of the first, second and third regions can vary depending on the NGS method selected, as they are dependent on the sequences that are necessary for priming for use with the selected NGS platform.

The hairpin adapters include at least one, preferably only one, uracil that allows the adaptor to be opened by Uracil DNA glycosylase (UDG) and Endonuclease VIII, a DNA glycosylase-lyase, e.g., the USER (Uracil-Specific Excision Reagent) Enzyme mixture (New England BioLabs). The UDG catalyzes the excision of uracil bases to form an abasic site but leave the phosphodiester backbone intact (see, e.g., Lindhal et al., J. Biol. Chem. 252:3286-3294 (1977); Lindhal, Annu. Rev. Biochem. 51:61-64 (1982)). The Endonuclease VIII breaks the phosphodiester backbone at the 3' and 5' sides of the abasic site (see, e.g., Melamede et al., Biochemistry 33:1255-1264 (1994); Jiang et al., J. Biol. Chem. 272:32230-32239 (1997)). This combination generates a single nucleotide gap at the location of a uracil. In some embodiments, in the 5' single-tailed hairpin adapters the uracil is placed at or within 1, 2, 3, or 4 nucleotides of the end of the first region and the beginning of the second region, and in the 3' single-tailed hairpin adapters the uracil is placed at or within 1, 2, 3, or 4 nucleotides of the end of the first region and the beginning of the second region.

In the present methods, all parts of the hairpin adapters are preferably orthologous to the genome of the cell (i.e., are not present in or complementary to a sequence present in, i.e., have no more than 10%, 20%, 30%, 40%, or 50% identity to a sequence present in, the genome of the cell). The hairpin adapters can preferably be between 65 and 95 nts long, e.g., 70-90 nts or 75-85 nts long.

Each of the 5' and 3' single-tailed hairpin adapters should include a primer site that is a randomized DNA barcode (e.g., SHAPE-SEQ, Lucks et al., Proc Natl Acad Sci USA 108: 11063-11068), unique molecular identifier (UMI) (see, e.g., Kivioja et al., Nature Methods 9, 72-74 (2012); Islam et al., Nature Methods 11, 163-166 (2014); Karlsson et al., Genomics. 2015 March; 105(3):150-8), or unique PCR priming sequence and/or unique sequence compatible for use in sequencing (e.g., NGS). The sequence compatible for use in sequencing can be selected for use with a desired sequencing method, e.g., a next generation sequencing method, e.g., Illumina, Ion Torrent or library preparation method like Roche/454, lllumina Solexa Genome Analyzer, the Applied Biosystems SOLiD™ system, Ion Torrent™ semiconductor sequence analyzer, PacBio® real-time sequencing and Helicos™ Single Molecule Sequencing (SMS). See, e.g., WO2014020137, Voelkerding et al., Clinical Chemistry 55:4 641-658 (2009) and Metzker, Nature Reviews Genetics 11:31-46 (2010)). A number of kits are commercially available for preparing DNA for NGS, including the ThruPLEX DNA-seq Kit (Rubicon; see U.S. Pat. Nos. 7,803,550; 8,071,312; 8,399,199; 8,728,737) and NEB-Next® (New England BioLabs; see e.g., U.S. Pat. No. 8,420,319)). Exemplary sequences are shown in Table A, below.

In some embodiments, the hairpin adapters include a restriction enzyme recognition site, preferably a site that is relatively uncommon in the genome of the cell.

The hairpin adapters are preferably modified; in some embodiments, the 5' ends of the hairpin adapters are phosphorylated. In some embodiments, the hairpin adapters are blunt ended. In some embodiments, the hairpin adapters include a random variety of 1, 2, 3, 4 or more nucleotide overhangs on the 5' or 3' ends, or include a single T at the 5' or 3' end.

The hairpin adapters can also include one or more additional modifications, e.g., as known in the art or described in PCT/US2011/060493. For example, in some embodiments, the hairpin adapters is biotinylated. The biotin can be anywhere internal to the hairpin adapters (e.g., a modified thymidine residue (Biotin-dT) or using biotin azide), but not on the 5' or 3' ends. This provides an alternate method of recovering fragments that contain the FIND-seq hairpin adapters. Whereas in some embodiments, these sequences are retrieved and identified by PCR, in this approach they are physically pulled down and enriched by using the biotin, e.g., by binding to streptavidin-coated magnetic beads, or using solution hybrid capture; see, e.g., Gnirke et al., Nature Biotechnology 27, 182-189 (2009).

Although the present working examples include ligating the 5' adapter and then the 3' adapter, the adapters can be added in either order, i.e., 5' adapter then 3' adapter, or 3' adapter then 5' adapter. The order may be optimized depending on the exonuclease treatment used, e.g., for Lambda exonuclease, which is a highly processive 5'→3' exonuclease, where adding the 5' adapter second may be advantageous.

Engineered Nucleases

There are presently four main classes of engineered nucleases: 1) meganucleases, 2) zinc-finger nucleases, 3) transcription activator effector-like nucleases (TALEN), and 4) Clustered Regularly Interspaced Short Palindromic Repeats (CRISPR) Cas RNA-guided nucleases (RGN). See, e.g., Gaj et al., Trends Biotechnol. 2013 July; 31(7):397-405. Any of these, or variants thereof, can be used in the present methods. The nuclease can be transiently or stably expressed in the cell, using methods known in the art; typically, to obtain expression, a sequence encoding a protein is subcloned into an expression vector that contains a promoter to direct transcription. Suitable eukaryotic expression systems are well known in the art and described, e.g., in Sambrook et al., *Molecular Cloning, A Laboratory Manual* (4th ed. 2013); Kriegler, *Gene Transfer and Expression: A Laboratory Manual* (2006); and *Current Protocols in Molecular Biology* (Ausubel et al., eds., 2010). Transformation of eukaryotic and prokaryotic cells are performed according to standard techniques (see, e.g., the reference above and Morrison, 1977, J. Bacteriol. 132:349-351; Clark-Curtiss & Curtiss, Methods in Enzymology 101:347-362 (Wu et al., eds, 1983).

Homing Meganucleases

Meganucleases are sequence-specific endonucleases originating from a variety of organisms such as bacteria, yeast, algae and plant organelles. Endogenous meganucleases have recognition sites of 12 to 30 base pairs; customized DNA binding sites with 18 bp and 24 bp-long meganuclease recognition sites have been described, and either can be used in the present methods and constructs. See, e.g., Silva, G., et al., Current Gene Therapy, 11:11-27, (2011); Arnould et al., Journal of Molecular Biology, 355:443-58 (2006); Arnould et al., Protein Engineering Design & Selection, 24:27-31 (2011); and Stoddard, Q. Rev. Biophys. 38, 49 (2005); Grizot et al., Nucleic Acids Research, 38:2006-18 (2010).

CRISPR-Cas Nucleases

Recent work has demonstrated that clustered, regularly interspaced, short palindromic repeats (CRISPR)/CRISPR-associated (Cas) systems (Wiedenheft et al., Nature 482, 331-338 (2012); Horvath et al., Science 327, 167-170 (2010); Terns et al., Curr Opin Microbiol 14, 321-327 (2011)) can serve as the basis of a simple and highly efficient method for performing genome editing in bacteria, yeast and human cells, as well as in vivo in whole organisms such as fruit flies, zebrafish and mice (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194(4):1029-35 (2013)). The Cas9 nuclease from *S. pyogenes* can be guided via simple base pair complementarity between 17-20 nucleotides of an engineered guide RNA (gRNA), e.g., a single guide RNA or crRNA/tracrRNA pair, and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)).

In some embodiments, the present system utilizes a wild type or variant Cas9 protein from *S. pyogenes* or *Staphylococcus aureus*, either as encoded in bacteria or codon-optimized for expression in mammalian cells. The guide RNA is expressed in the cell together with the Cas9. Either the guide RNA or the nuclease, or both, can be expressed transiently or stably in the cell.

TAL Effector Repeat Arrays

TAL effectors of plant pathogenic bacteria in the genus *Xanthomonas* play important roles in disease, or trigger defense, by binding host DNA and activating effector-specific host genes. Specificity depends on an effector-variable number of imperfect, typically ~33-35 amino acid repeats. Polymorphisms are present primarily at repeat positions 12 and 13, which are referred to herein as the repeat variable-diresidue (RVD). The RVDs of TAL effectors correspond to the nucleotides in their target sites in a direct, linear fashion, one RVD to one nucleotide, with some degeneracy and no apparent context dependence. In some embodiments, the polymorphic region that grants nucleotide specificity may be expressed as a triresidue or triplet.

Each DNA binding repeat can include a RVD that determines recognition of a base pair in the target DNA sequence, wherein each DNA binding repeat is responsible for recognizing one base pair in the target DNA sequence. In some embodiments, the RVD can comprise one or more of: HA for recognizing C; ND for recognizing C; HI for recognizing C; HN for recognizing G; NA for recognizing G; SN for recognizing G or A; YG for recognizing T; and NK for recognizing G, and one or more of: HD for recognizing C; NG for recognizing T; NI for recognizing A; NN for recognizing G or A; NS for recognizing A or C or G or T; N* for recognizing C or T, wherein * represents a gap in the second position of the RVD; HG for recognizing T; H* for recognizing T, wherein * represents a gap in the second position of the RVD; and IG for recognizing T.

TALE proteins may be useful in research and biotechnology as targeted chimeric nucleases that can facilitate homologous recombination in genome engineering (e.g., to add or enhance traits useful for biofuels or biorenewables in plants). These proteins also may be useful as, for example, transcription factors, and especially for therapeutic applications requiring a very high level of specificity such as therapeutics against pathogens (e.g., viruses) as non-limiting examples.

Methods for generating engineered TALE arrays are known in the art, see, e.g., the fast ligation-based automatable solid-phase high-throughput (FLASH) system described in USSN 61/610,212, and Reyon et al., Nature Biotechnology 30,460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

Also suitable for use in the present methods are Mega-TALs, which are a fusion of a meganuclease with a TAL effector; see, e.g., Boissel et al., Nucl. Acids Res. 42(4): 2591-2601 (2014); Boissel and Scharenberg, Methods Mol Biol. 2015; 1239:171-96.

Zinc Fingers

Zinc finger proteins are DNA-binding proteins that contain one or more zinc fingers, independently folded zinc-containing mini-domains, the structure of which is well known in the art and defined in, for example, Miller et al., 1985, EMBO J., 4:1609; Berg, 1988, Proc. Natl. Acad. Sci. USA, 85:99; Lee et al., 1989, Science. 245:635; and Klug, 1993, Gene, 135:83. Crystal structures of the zinc finger protein Zif268 and its variants bound to DNA show a semi-conserved pattern of interactions, in which typically three amino acids from the alpha-helix of the zinc finger contact three adjacent base pairs or a "subsite" in the DNA (Pavletich et al., 1991, Science, 252:809; Elrod-Erickson et al., 1998, Structure, 6:451). Thus, the crystal structure of Zif268 suggested that zinc finger DNA-binding domains might function in a modular manner with a one-to-one interaction between a zinc finger and a three-base-pair "subsite" in the DNA sequence. In naturally occurring zinc finger transcription factors, multiple zinc fingers are typically linked together in a tandem array to achieve sequence-specific recognition of a contiguous DNA sequence (Klug, 1993, Gene 135:83).

Multiple studies have shown that it is possible to artificially engineer the DNA binding characteristics of individual zinc fingers by randomizing the amino acids at the alpha-helical positions involved in DNA binding and using selection methodologies such as phage display to identify desired variants capable of binding to DNA target sites of interest (Rebar et al., 1994, Science, 263:671; Choo et al., 1994 Proc. Natl. Acad. Sci. USA, 91:11163; Jamieson et al., 1994, Biochemistry 33:5689; Wu et al., 1995 Proc. Natl. Acad. Sci. USA, 92: 344). Such recombinant zinc finger proteins can be fused to functional domains, such as transcriptional activators, transcriptional repressors, methylation domains, and nucleases to regulate gene expression, alter DNA methylation, and introduce targeted alterations into genomes of model organisms, plants, and human cells (Carroll, 2008, Gene Ther., 15:1463-68; Cathomen, 2008, Mol. Ther., 16:1200-07; Wu et al., 2007, Cell. Mol. Life Sci., 64:2933-44).

One existing method for engineering zinc finger arrays, known as "modular assembly," advocates the simple joining together of pre-selected zinc finger modules into arrays (Segal et al., 2003, Biochemistry, 42:2137-48; Beerli et al., 2002, Nat. Biotechnol., 20:135-141; Mandell et al., 2006, Nucleic Acids Res., 34:W516-523; Carroll et al., 2006, Nat. Protoc. 1:1329-41; Liu et al., 2002, J. Biol. Chem., 277: 3850-56; Bae et al., 2003, Nat. Biotechnol., 21:275-280;

Wright et al., 2006, Nat. Protoc., 1:1637-52). Although straightforward enough to be practiced by any researcher, recent reports have demonstrated a high failure rate for this method, particularly in the context of zinc finger nucleases (Ramirez et al., 2008, Nat. Methods, 5:374-375; Kim et al., 2009, Genome Res. 19:1279-88), a limitation that typically necessitates the construction and cell-based testing of very large numbers of zinc finger proteins for any given target gene (Kim et al., 2009, Genome Res. 19:1279-88).

Combinatorial selection-based methods that identify zinc finger arrays from randomized libraries have been shown to have higher success rates than modular assembly (Maeder et al., 2008, Mol. Cell, 31:294-301; Joung et al., 2010, Nat. Methods, 7:91-92; Isalan et al., 2001, Nat. Biotechnol., 19:656-660). In preferred embodiments, the zinc finger arrays are described in, or are generated as described in, WO 2011/017293 and WO 2004/099366. Additional suitable zinc finger DBDs are described in U.S. Pat. Nos. 6,511,808, 6,013,453, 6,007,988, and 6,503,717 and U.S. patent application 2002/0160940.

DNA

The methods described herein can be applied to any double stranded DNA, e.g., genomic DNA isolated from any cell, artificially created populations of DNAs, or any other DNA pools, as it is performed in vitro.

Sequencing

As used herein, "sequencing" includes any method of determining the sequence of a nucleic acid. Any method of sequencing can be used in the present methods, including chain terminator (Sanger) sequencing and dye terminator sequencing. In preferred embodiments, Next Generation Sequencing (NGS), a high-throughput sequencing technology that performs thousands or millions of sequencing reactions in parallel, is used. Although the different NGS platforms use varying assay chemistries, they all generate sequence data from a large number of sequencing reactions run simultaneously on a large number of templates. Typically, the sequence data is collected using a scanner, and then assembled and analyzed bioinformatically. Thus, the sequencing reactions are performed, read, assembled, and analyzed in parallel; see, e.g., US 20140162897, as well as Voelkerding et al., Clinical Chem., 55: 641-658, 2009; and MacLean et al., Nature Rev. Microbiol., 7: 287-296 (2009). Some NGS methods require template amplification and some that do not. Amplification-requiring methods include pyrosequencing (see, e.g., U.S. Pat. Nos. 6,210,89 and 6,258,568; commercialized by Roche); the Solexa/Illumina platform (see, e.g., U.S. Pat. Nos. 6,833,246, 7,115,400, and 6,969,488); and the Supported Oligonucleotide Ligation and Detection (SOLiD) platform (Applied Biosystems; see, e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476,503). See, e.g., US 20130274147; US20140038831; Metzker, Nat Rev Genet 11(1): 31-46 (2010).

Alternatively, hybridization-based sequence methods or other high-throughput methods can also be used, e.g., microarray analysis, NANOSTRING, ILLUMINA, or other sequencing platforms.

Kits

Also provided herein are kits for use in the methods described herein. The kits can include one or more of the following: 5' single-tailed hairpin adapters; 3' single-tailed hairpin adapters; reagents and/or enzymes for end repair and A tailing (e.g., T4 polymerase, Klenow fragment, T4 Polynucleotide Kinase (PNK), and/or Taq DNA Polymerase); exonuclease; uracil DNA glycosylase (UDG) and/or endonuclease VIII, a DNA glycosylase-lyase, e.g., the USER (Uracil-Specific Excision Reagent) Enzyme mixture (New England BioLabs); purified cas9 protein; guideRNA (e.g., control gRNA); gDNA template (e.g., control gDNA template); and instructions for use in a method described herein.

EXAMPLES

The invention is further described in the following examples, which do not limit the scope of the invention described in the claims.

Materials

The following materials were used in Examples 1-2.

| Materials | Vendor | Model Number |
|---|---|---|
| HTP Library Preparation Kit | Kapa Biosystems | KK8235 |
| Hifi HotStart ReadyMix, 100 × 25 μL reactions | Kapa Biosystems | KK2602 |
| Lambda exonuclease (5 U/ul) | NEB | M0262L |
| E. Coli Exonuclease I (20 U/ul) | NEB | M0293S |
| USER enzyme (1000 U/ul) | NEB | M5505L |
| Cas9 enzyme (1000 nM) | NEB | M0386L |
| Ampure XP 60 ml | Agencourt | A63881 |

The following Primers were used in Examples 1-2.

TABLE A

| PrimerName | Sequence | SEQ ID NO: |
|---|---|---|
| oSQT1270 5'-Truseq-loop-adapter D501L | /5phos/gatcggaagagc/ideoxyU/ aatgatacggcgaccaccgagatctacac TATAGCCT acactctttccctacacgacgctcttccgatc*t | 1 |
| oSQT1302 5'-Truseq-loop-adapter D502L | /5phos/gatcggaagagc/ideoxyU/ aatgatacggcgaccaccgagatctacac ATAGAGGC acactctttccctacacgacgctcttccgatc*t | 2 |
| oSQT1303 5'-Truseq-loop-adapter D503L | /5phos/gatcggaagagc/ideoxyU/ aatgatacggcgaccaccgagatctacac CCTATCCT acactctttccctacacgacgctcttccgatc*t | 3 |

TABLE A-continued

| PrimerName | Sequence | SEQ ID NO: |
|---|---|---|
| oSQT1304 5'-Truseq-loop-adapter D504L | /5phos/gatcggaagagc/ideoxyU/ aatgatacggcgaccaccgagatctacac GGCTCTGA acactctttccctacacgacgctcttccgatc*t | 4 |
| oSQT1305 5'-Truseq-loop-adapter D505L | /5phos/gatcggaagagc/ideoxyU/ aatgatacggcgaccaccgagatctacac AGGCGAAG acactctttccctacacgacgctcttccgatc*t | 5 |
| oSQT1315 5'-Truseq-loop-adapter D506L | /5phos/gatcggaagagc/ideoxyU/ aatgatacggcgaccaccgagatctacac TAATCTTA acactctttccctacacgacgctcttccgatc*t | 6 |
| oSQT1316 5'-Truseq-loop-adapter D507L | /5phos/gatcggaagagc/ideoxyU/ aatgatacggcgaccaccgagatctacac CAGGACGT acactctttccctacacgacgctcttccgatc*t | 7 |
| oSQT1317 5'-Truseq-loop-adapter D508L | /5phos/gatcggaagagc/ideoxyU/ aatgatacggcgaccaccgagatctacac GTACTGAC acactctttccctacacgacgctcttccgatc*t | 8 |
| oSQT1271 3'-Truseq-loop-adapter D701L | /5phos/gatcggaagagcacacgtctgaactccagtcac ATTACTCG atctcgtatgccgtcttctgcttg/ ideoxyU/gctcttccgatc*t | 9 |
| oSQT1306 3'-Truseq-loop-adapter D702L | /5phos/gatcggaagagcacacgtctgaactccagtcac TCCGGAGA atctcgtatgccgtcttctgcttg/ ideoxyU/gctcttccgatc*t | 10 |
| oSQT1307 3'-Truseq-loop-adapter D703L | /5phos/gatcggaagagcacacgtctgaactccagtcac CGCTCATT atctcgtatgccgtcttctgcttg/ ideoxyU/gctcttccgatc*t | 11 |
| oSQT1308 3'-Truseq-loop-adapter D704L | /5phos/gatcggaagagcacacgtctgaactccagtcac GAGATTCC atctcgtatgccgtcttctgcttg/ ideoxyU/gctcttccgatc*t | 12 |
| oSQT1309 3'-Truseq-loop-adapter D705L | /5phos/gatcggaagagcacacgtctgaactccagtcac ATTCAGAA atctcgtatgccgtcttctgcttg/ ideoxyU/gctcttccgatc*t | 13 |
| oSQT1318 3'-Truseq-loop-adapter D706L | /5phos/gatcggaagagcacacgtctgaactccagtcac GAATTCGT atctcgtatgccgtcttctgcttg/ ideoxyU/gctcttccgatc*t | 14 |
| oSQT1319 3'-Truseq-loop-adapter D707L | /5phos/gatcggaagagcacacgtctgaactccagtcac CTGAAGCT atctcgtatgccgtcttctgcttg/ ideoxyU/gctcttccgatc*t | 15 |
| oSQT1320 3'-Truseq-loop-adapter D708L | /5phos/gatcggaagagcacacgtctgaactccagtcac TAATGCGC atctcgtatgccgtcttctgcttg/ ideoxyU/gctcttccgatc*t | 16 |
| oSQT1274 Truseq F1 | AATGATACGGCGACCACCGAG | 17 |
| oSQT1275 Truseq R1 | CAAGCAGAAGACGGCATACGAGAT | 18 |

The sequences in CAPS are dual-index barcodes (for demultiplexing samples) in the Illumina Truseq library preparation system.
The * represents a phosphorothioate linkage.

Example 1. Optimization of Exemplary FIND-Seq Methodology

Described herein is the development of an in vitro method that enables comprehensive determination of DSBs induced by nucleases on any genomic DNA of interest. This method enables enrichment of nuclease-induced DSBs over random DSBs induced by shearing of genomic DNA. An overview of how the method works can be found in FIGS. 1A and 1B. In brief, genomic DNA from a cell type or organism of interest is randomly sheared to a defined average length. In the present experiments, an average length of 500 bps works well for subsequent next-generation sequencing steps. The random broken ends of this genomic DNA are end repaired and then A-tailed. This then enables the ligation of a hairpin adapter bearing a 5' end next-generation sequencing primer site that also contains a single deoxyuridine nucleotide at a specific position (FIG. 1B); this adapter is also referred to herein as the "5' single-tailed hairpin adapter". Following ligation of this adapter, the sample is then treated with one or more exonucleases (e.g., *bacteriophage lambda* exonuclease, *E. coli* ExoI, PlasmidSafe ATP-dependent exonuclease), which degrades any DNA molecules that have not had the 5' single-tailed hairpin adapter ligation to both of their ends. The collection of molecules is then treated with Cas9 nuclease complexed with a specific guide RNA (gRNA). The resulting nuclease-induced blunt ends are A-tailed and then a second hairpin adapter bearing a 3' end next-generation sequencing primer site and that also contains a single deoxyuridine nucleotide at a specific position is ligated to these ends; this adapter is also referred to herein as the "3' single-tailed hairpin adapter". As a result of these treatments, the only DNA fragments that should have a 5' and a 3' single-tailed hairpin adapter ligated to their ends are those that were cleaved by the nuclease. The adapters can be added in any order. Following treatment by the USER enzyme mixture, which nicks DNA wherever a deoxyuridine is present, only those fragments bearing the two types of adapters can be sequenced.

Figure 2A:
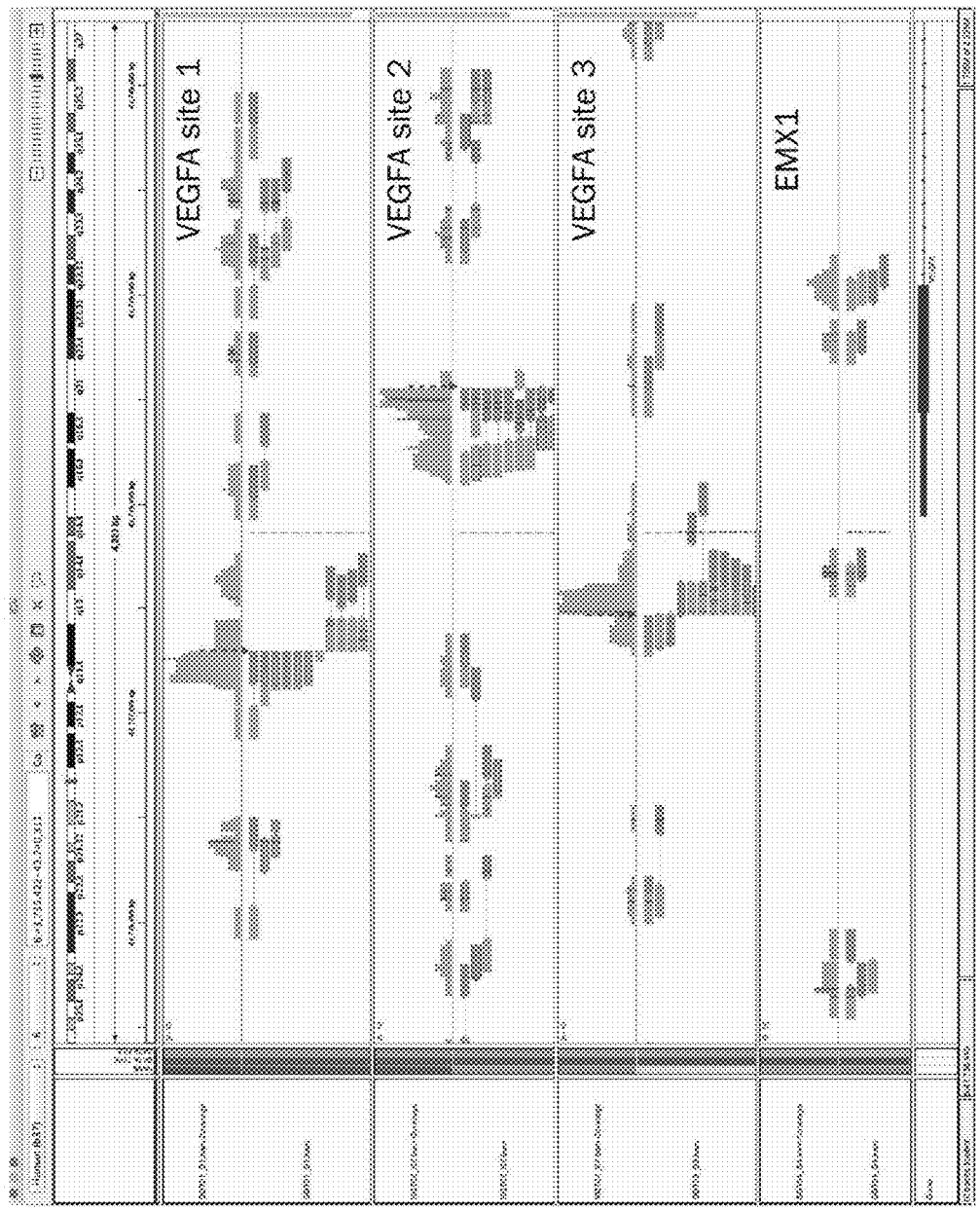
FIGS. 2A-B. Reads mapped at on-target and off-target cleavage sites. (a) Visualization of 'on-target' genomic regions where bidirectionally mapping uniform-end read signatures of Cas9 cleavage can be identified. Reads are indicated by red or blue rectangles; coverage is displayed above. The red arrow indicates the predicted cut site and data is shown for 3 target sites in the VEGFA locus. A sample treated with Streptococcus pyogenes Cas9 complexed with EMX1 gRNA is also shown as a negative control. (b) Visualization of example 'off-target' genomic region 20:56175349-56175372 in VEGFA site 1. Bidirectionally mapping reads with 'uniform' ends can be observed in this region and are typical of sites detected by this in vitro assay. Reads generally start within 1-bp of the predicted cut-site and originate outward in both directions from this position.
Figure 2B:
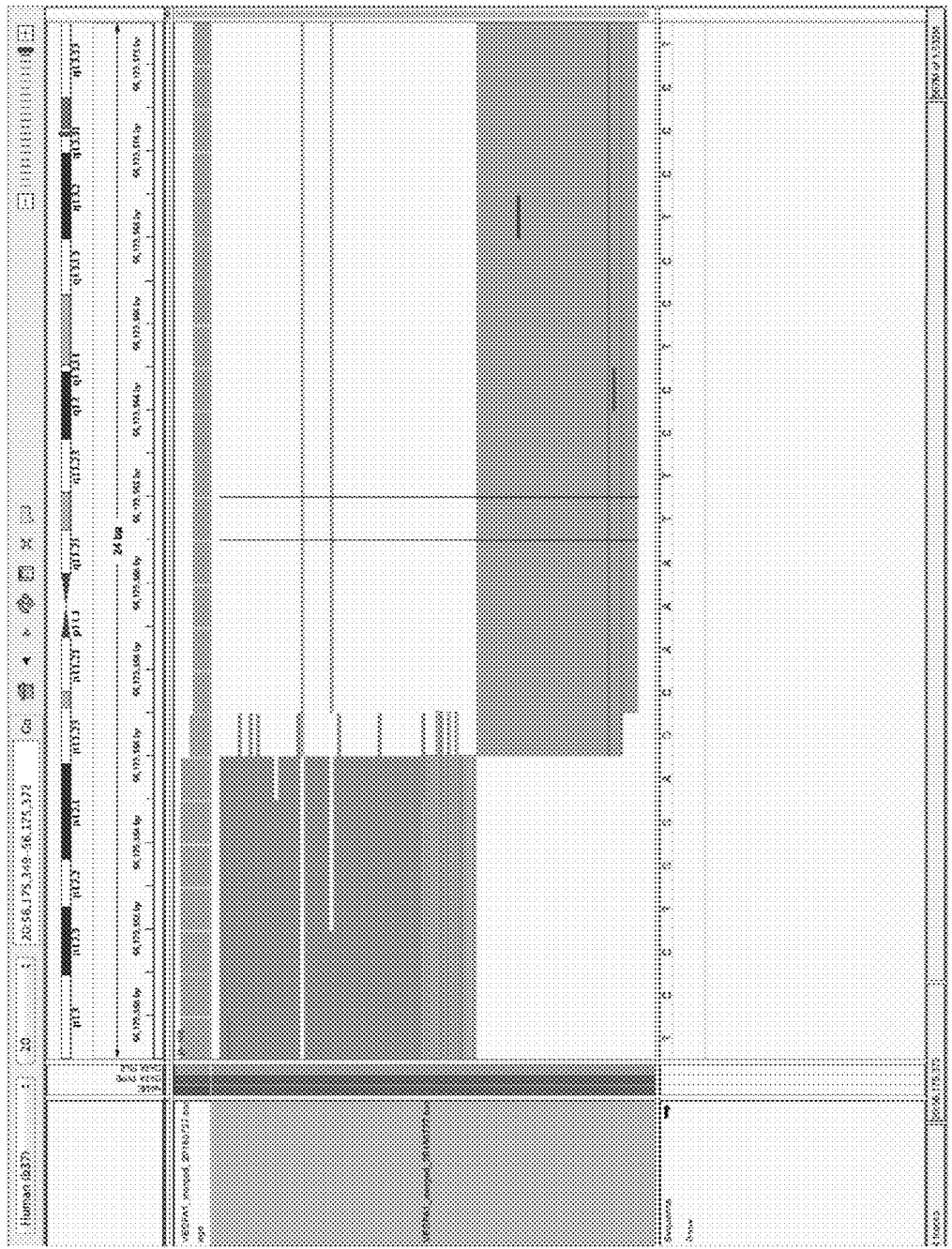
Figure 3A:
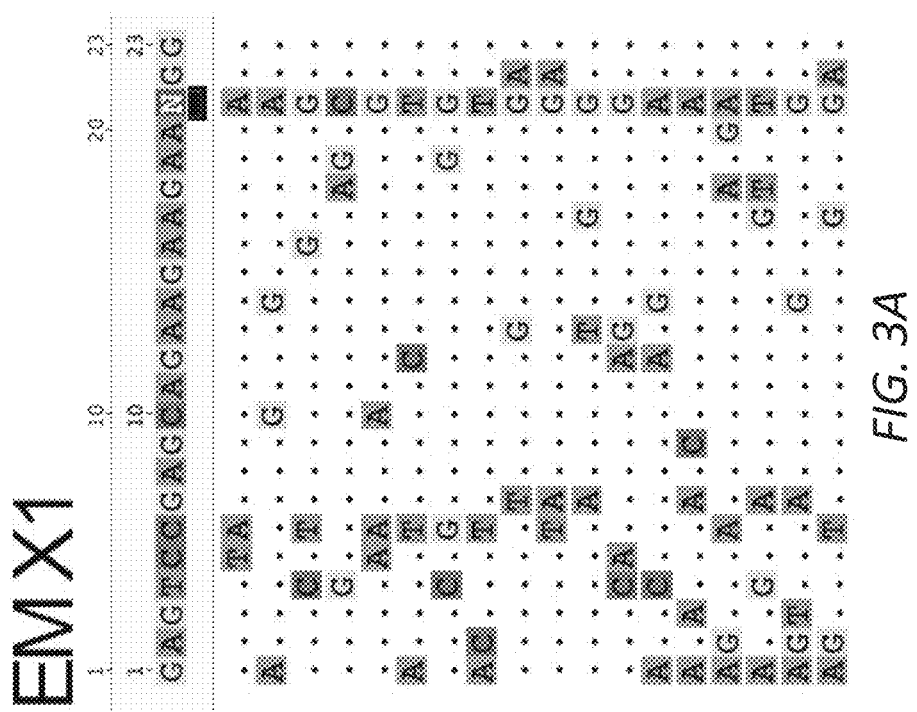
FIGS. 3A-D. Alignments of off-target cleavage sites detected by an exemplary genome-wide in vitro cleavage assay called FIND-seq. The intended target site is listed at the top of each alignment. Mismatched positions in the off-target cleavage sites relative to the intended site are indicated by bases highlighted with colored rectangles; matched positions are indicated by dots. Alignments are presented for four target sites: (a) EMX1 (SEQ ID NOS 23-41, respectively, in order of appearance), (b), VEGFA site 1 (SEQ ID NOS 42-81, respectively, in order of appearance), (c) VEGFA site 2 (SEQ ID NOS 82-264, respectively, in order of appearance), and (d) VEGFA site 3 (SEQ ID NOS 265-389, respectively, in order of appearance).
Figure 3B:
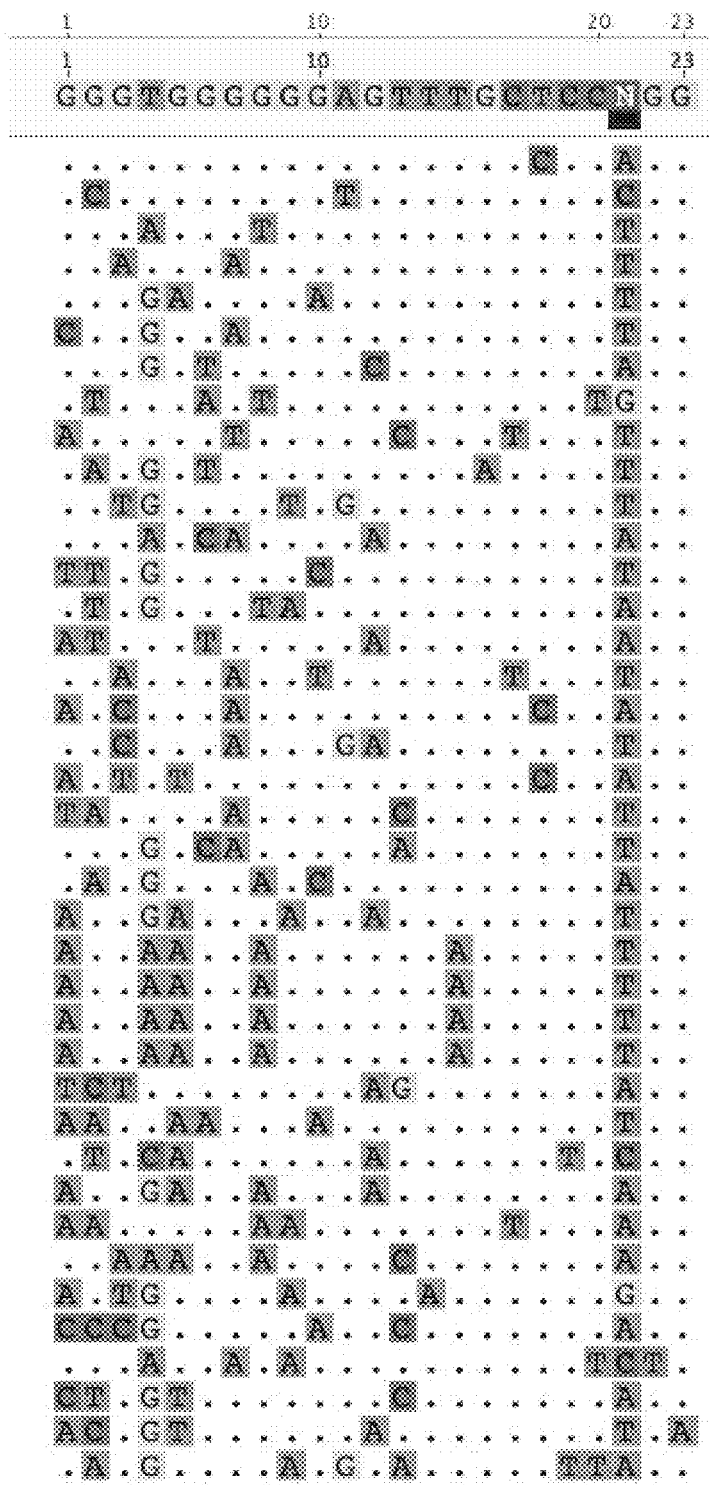
Figure 3C:
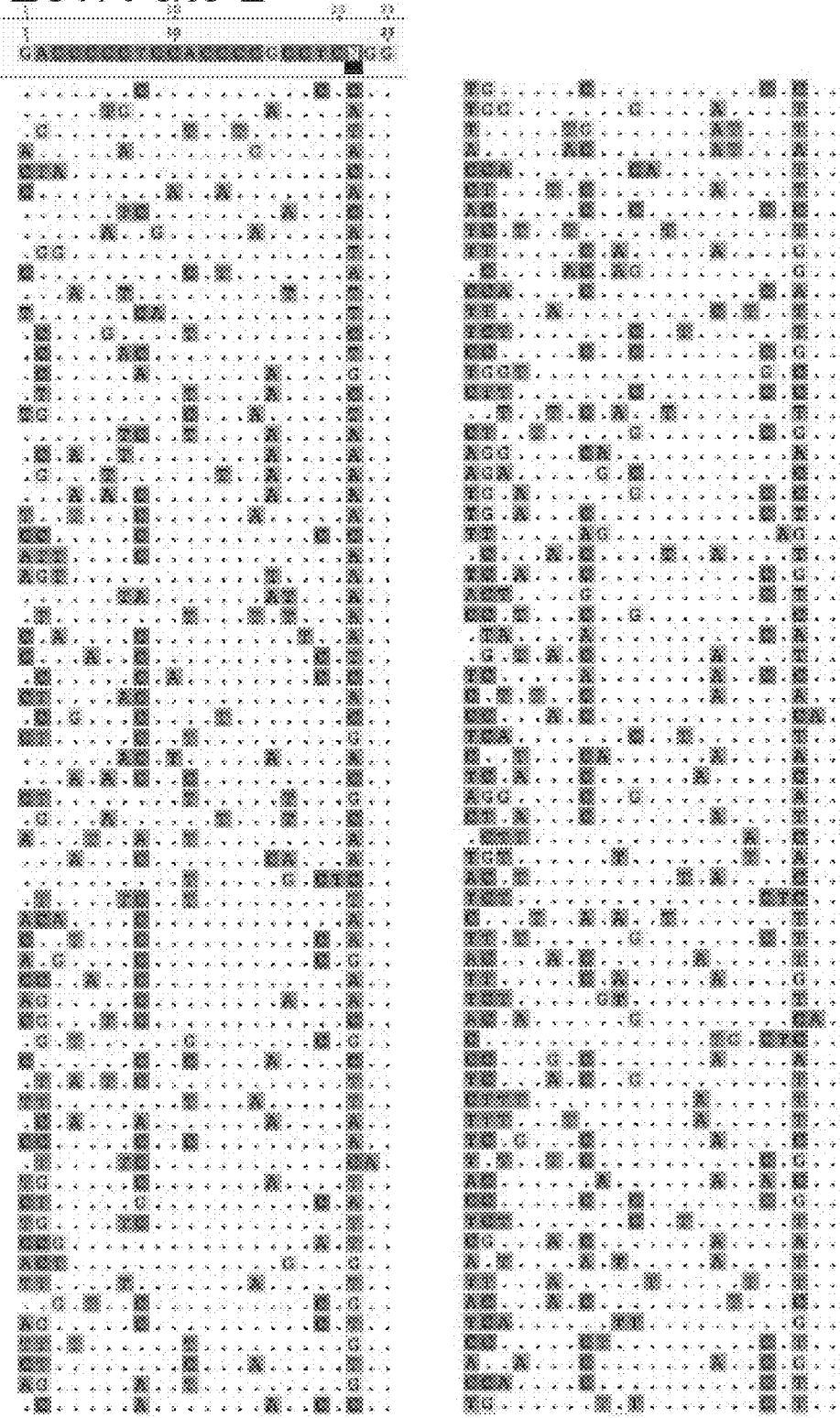
Figure 3D:
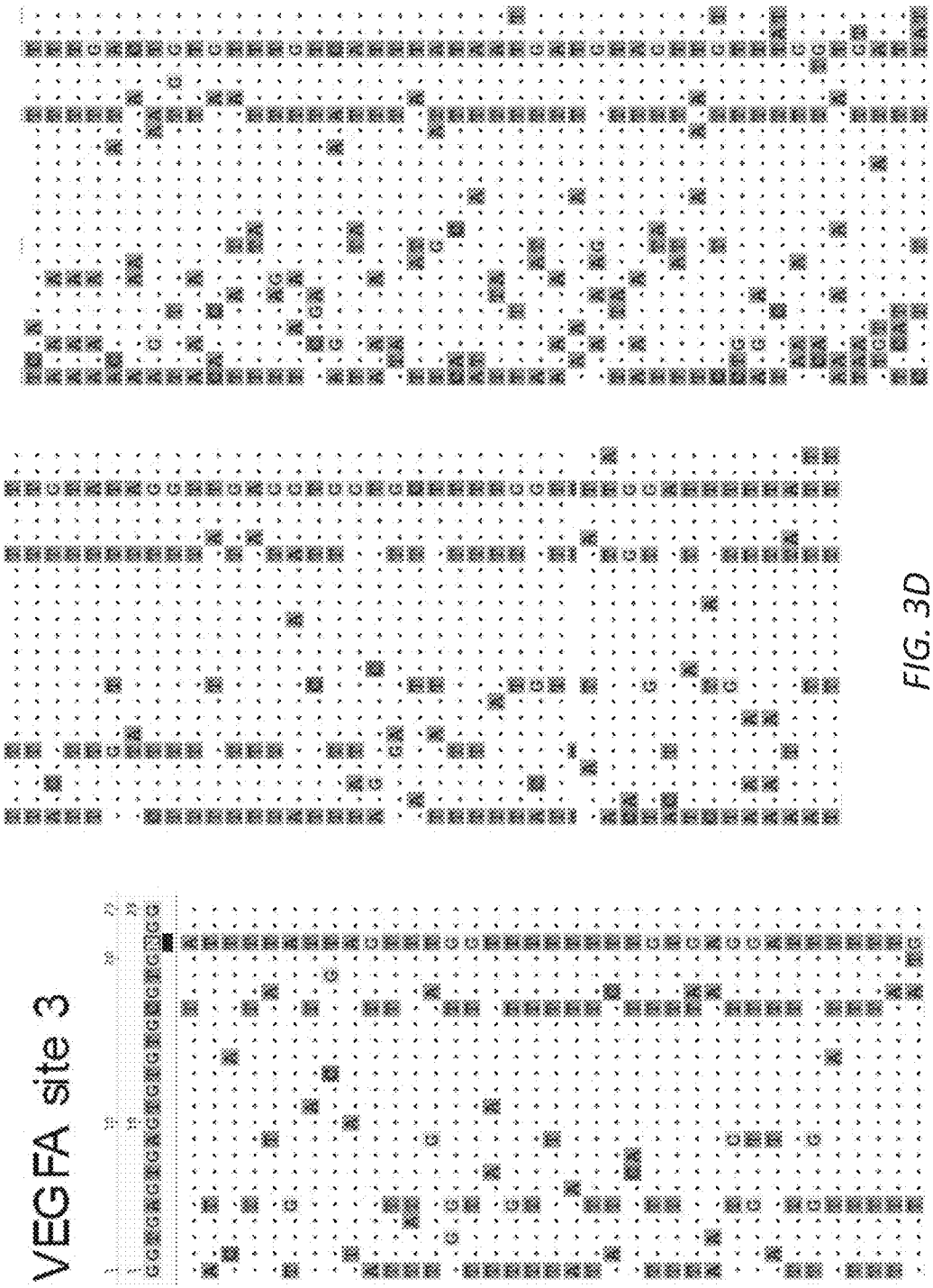
Figures 4A, 4B:
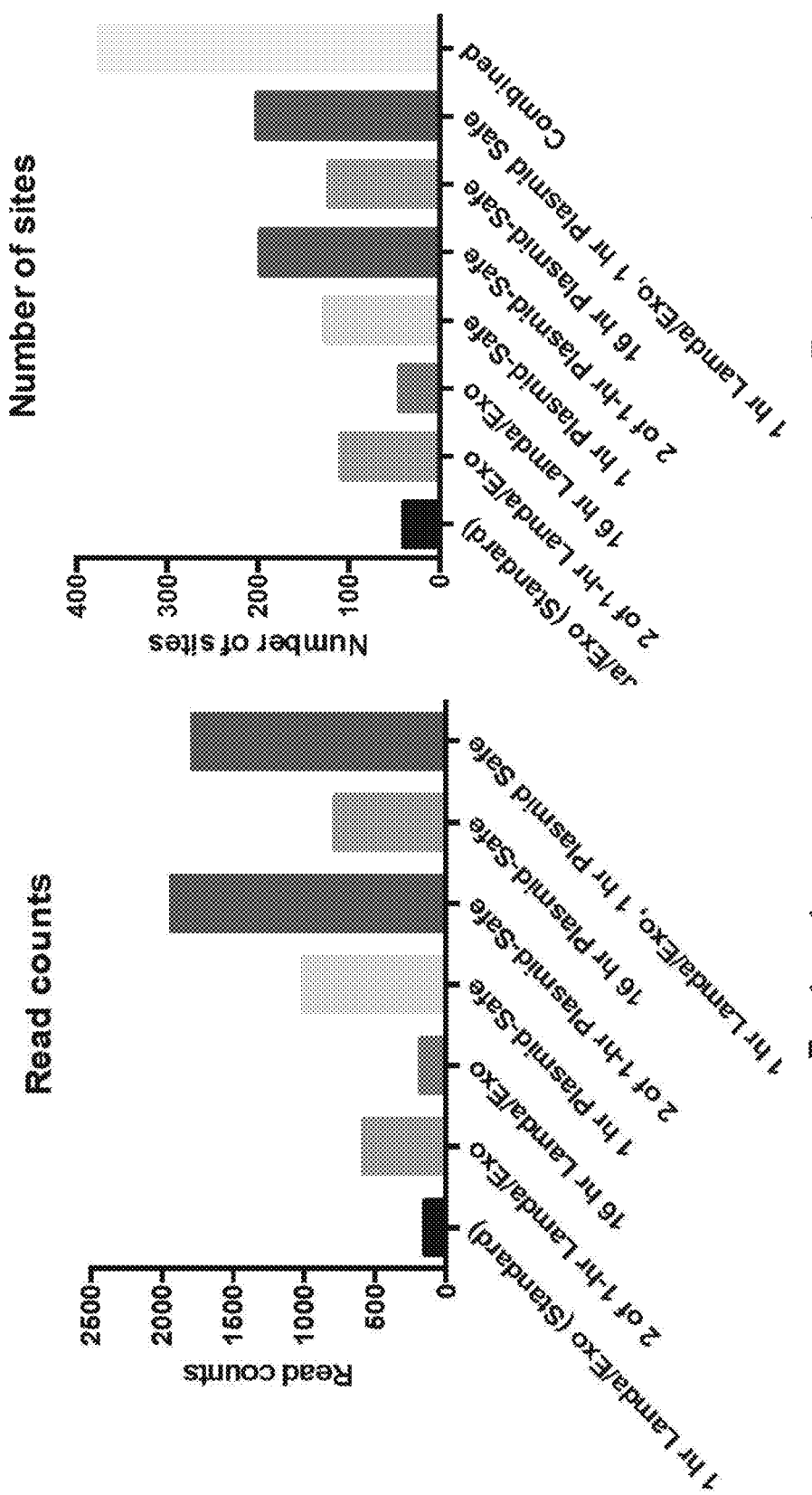
FIGS. 4A-D. Analysis of FIND-seq in vitro cleavage selection assay results using different exonuclease treatment conditions. (a) Mapped read counts at genome-wide in vitro cleavage assay detected sites for a under different exonuclease treatments. (b) Number of sites detected by genome-wide in vitro cleavage assay with different exonuclease treatments. (c) Average read counts at genome-wide in vitro cleavage assay detected sites under different exonuclease treatments. (d) Percentage of GUIDE-seq detected sites that are detected by genome-wide in vitro cleavage assay. Note there are three conditions where 100% of GUIDE-seq sites are detected using the simple in vitro assay.
Figures 4C, 4D:
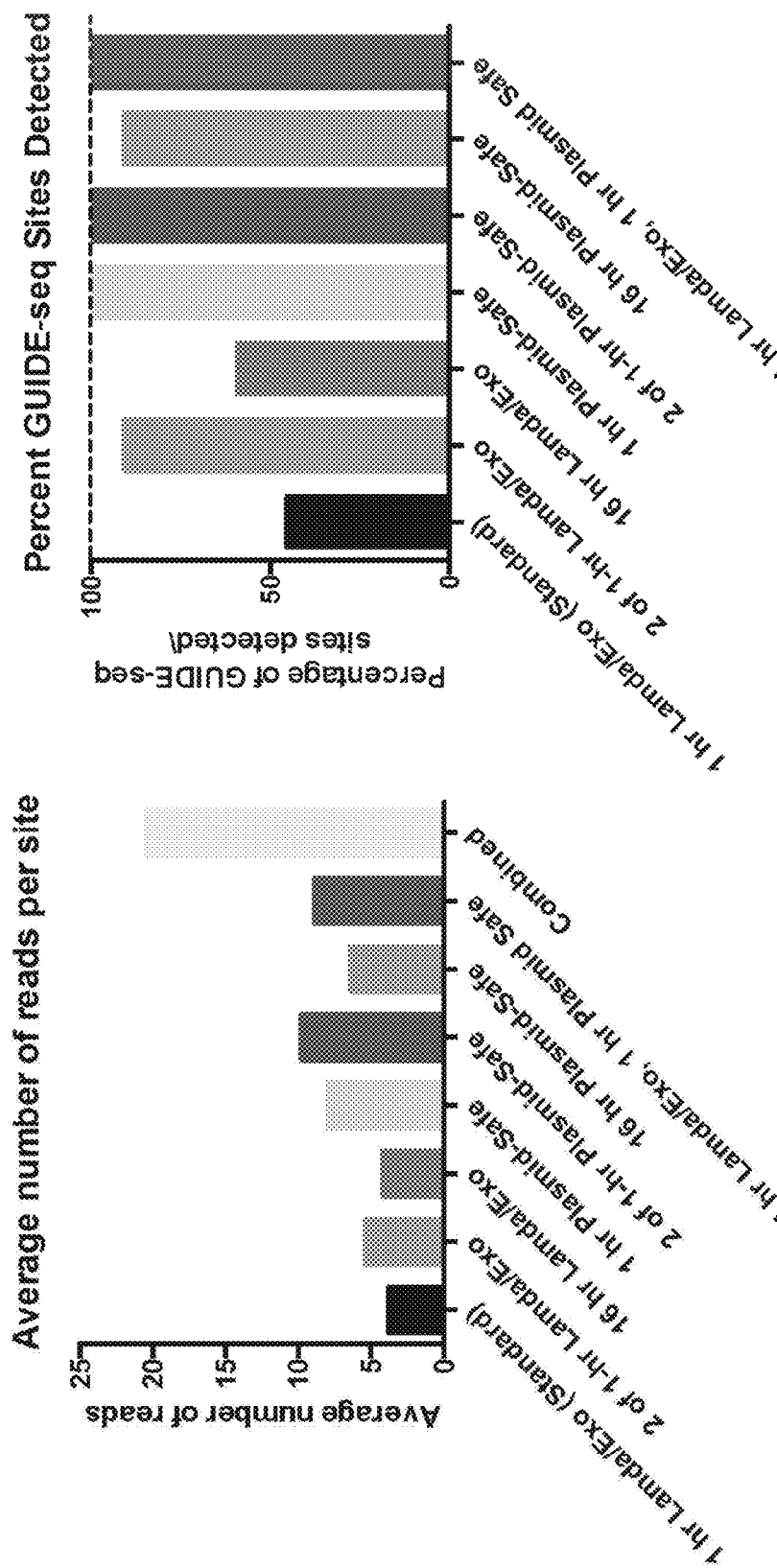
Figure 5A:
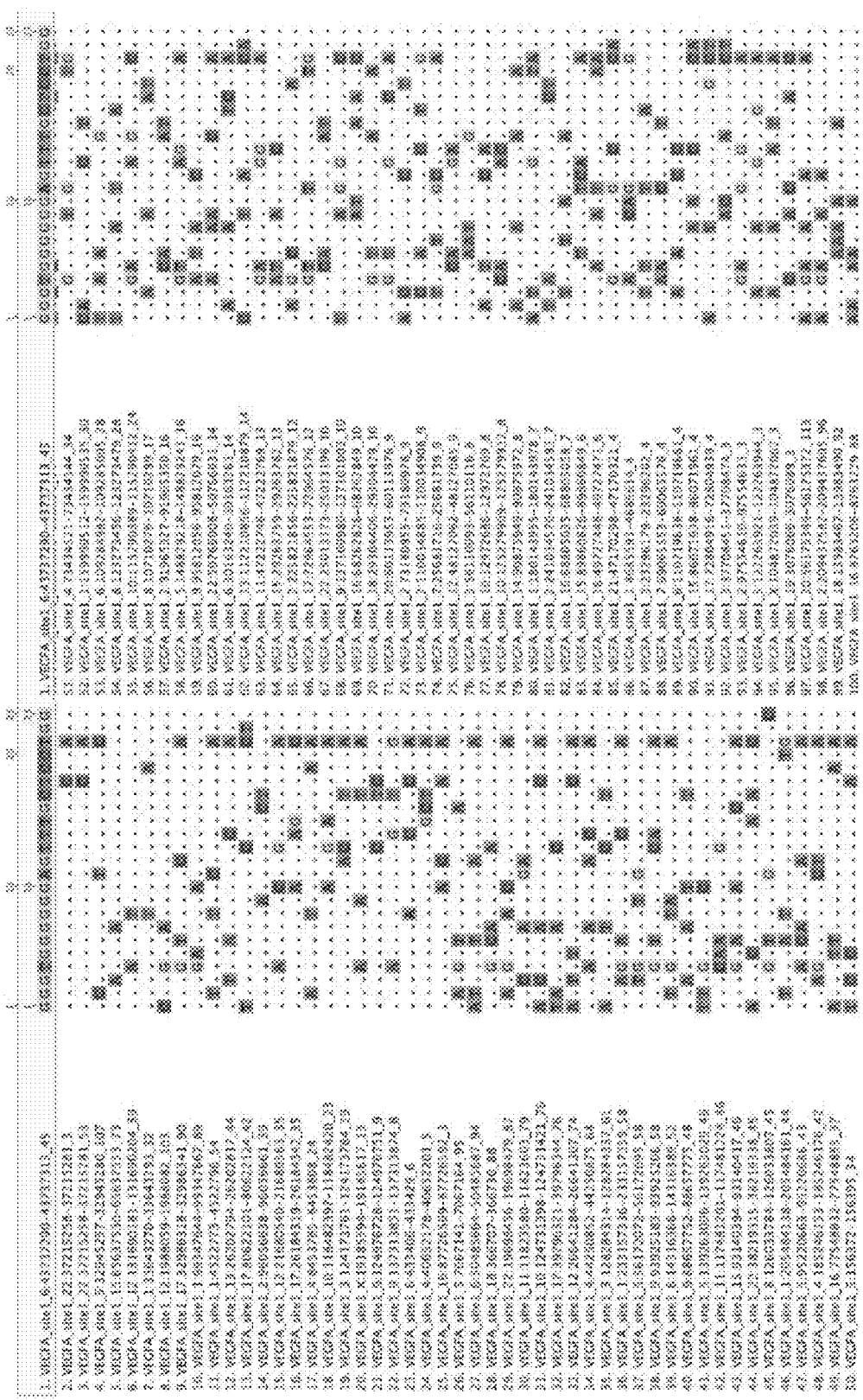
Figure 5B:
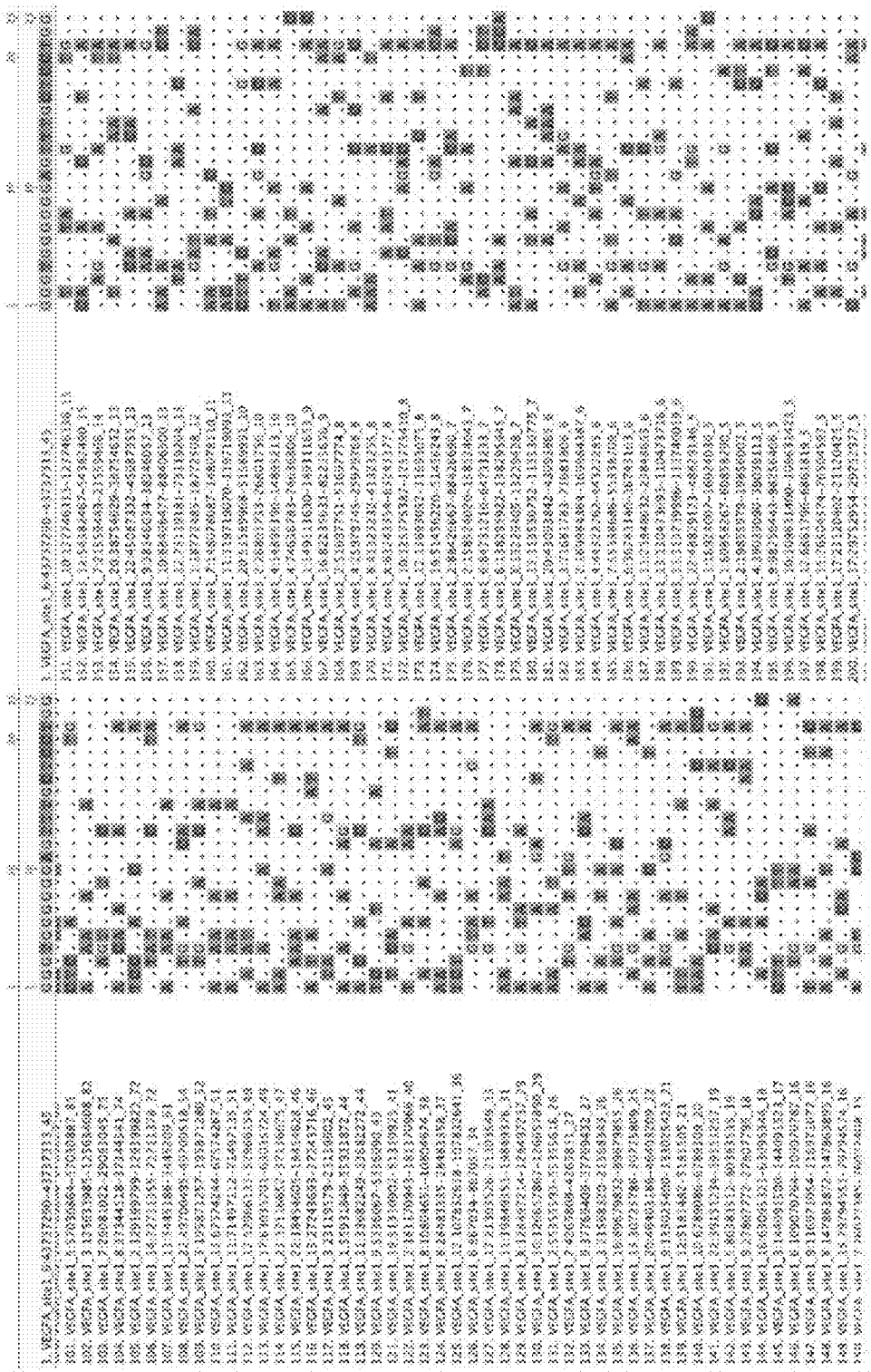
Figure 5D:
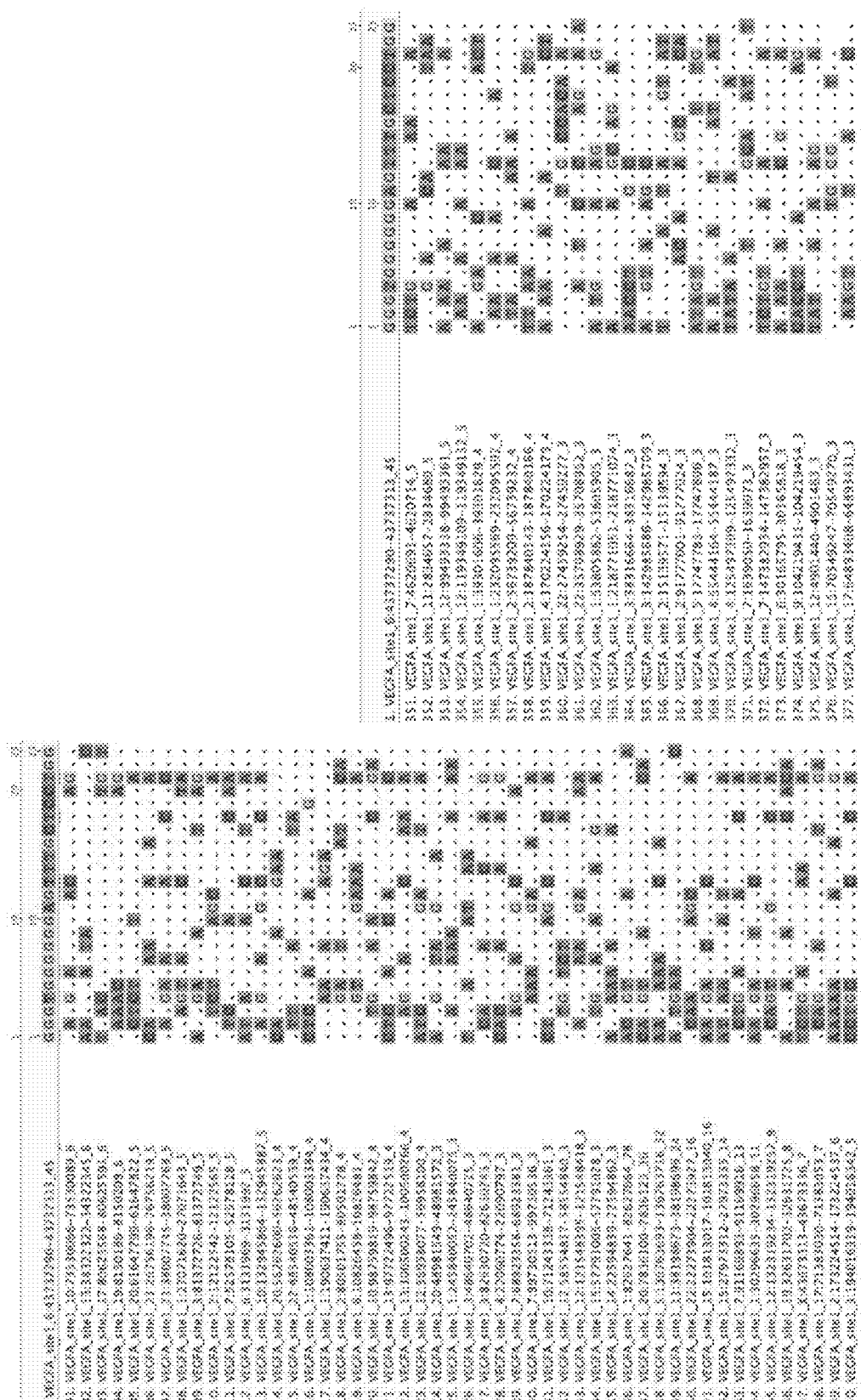

Following paired end next-generation sequencing, the resulting reads can be mapped back to the genome. Sites of nuclease cleavage will have multiple bi-direction reads originating at the site of the nuclease-induced DSB, typically within a nucleotide of the cut site (FIGS. 2A and 2B). As nuclease-induced cleavage produces 'uniform' ends, in contrast to the staggered ends that results from random physical shearing of DNA, these sites can be simply bioinformatically identified by their signature uniform read alignments.

Using an initial non-optimized version of this approach, off-target sites induced by four different gRNAs and Cas9 nuclease (FIG. 3) were successfully identified. The target sites are listed in Table 1.

TABLE 1

List of sgRNA target sites tested with in vitro cleavage selection assay.

| Target site name | Cells | Target Site (5'→3') | SEQ ID NO: |
|---|---|---|---|
| VEGFA site1 | U2OS | GGGTGGGGGGAGTTTGCTCCNGG | 19 |
| VEGFA site2 | U2OS | GACCCCCTCCACCCCGCCTCNGG | 20 |
| VEGFA site3 | U2OS | GGTGAGTGAGTGTGTGCGTGNGG | 21 |
| EMX1 | U2OS | GAGTCCGAGCAGAAGAAGAANGG | 22 |

The results of table 2 were encouraging for this assay, as the majority of GUIDE-seq detected sites were also detected by this method. In the first trial, 58-77% of sites overlapped between methods using 2.5-3M reads. ~20,000× enrichment was estimated for cleaved sites.

TABLE 2

List of sgRNA target sites tested with in vitro cleavage selection assay.

| site | cell-based GUIDE-seq total | in vitro total | both | percentage of cell-based GUIDE-seq sites detected |
|---|---|---|---|---|
| EMX1 | 16 | 19 | 10 | 63% |
| VEGFA site 1 | 22 | 41 | 17 | 77% |
| VEGFA site 2 | 152 | 194 | 98 | 64% |
| VEGFA site 3 | 60 | 129 | 35 | 58% |

A critical parameter for optimization of the present method was the efficiency of degradation of linear DNA fragments following the ligation of the first 5' single-tailed hairpin adapter. Indeed, without wishing to be bound by theory, most of the "background" reads mapped throughout the genome may be due to incomplete digestion of unligated DNA at this step, thereby leaving ends to which the second 3' single tailed hairpin adapter can be ligated.

Therefore, the methods were further optimized by testing various kinds and numbers of exonucleases and lengths of incubation to find an optimal treatment method. As seen in FIGS. 4A-4D, three treatments consistently yielded the highest number of reads and sites and also found 100% of the off-target sites identified by matched GUIDE-seq experiments with the same gRNAs: 1 hour PlasmidSafe treatment, two serial 1 hour PlasmidSafe treatments, and 1 hour of *Lambda* exonuclease treatment followed by 1 hour of PlasmidSafe treatment.

Figure 6:
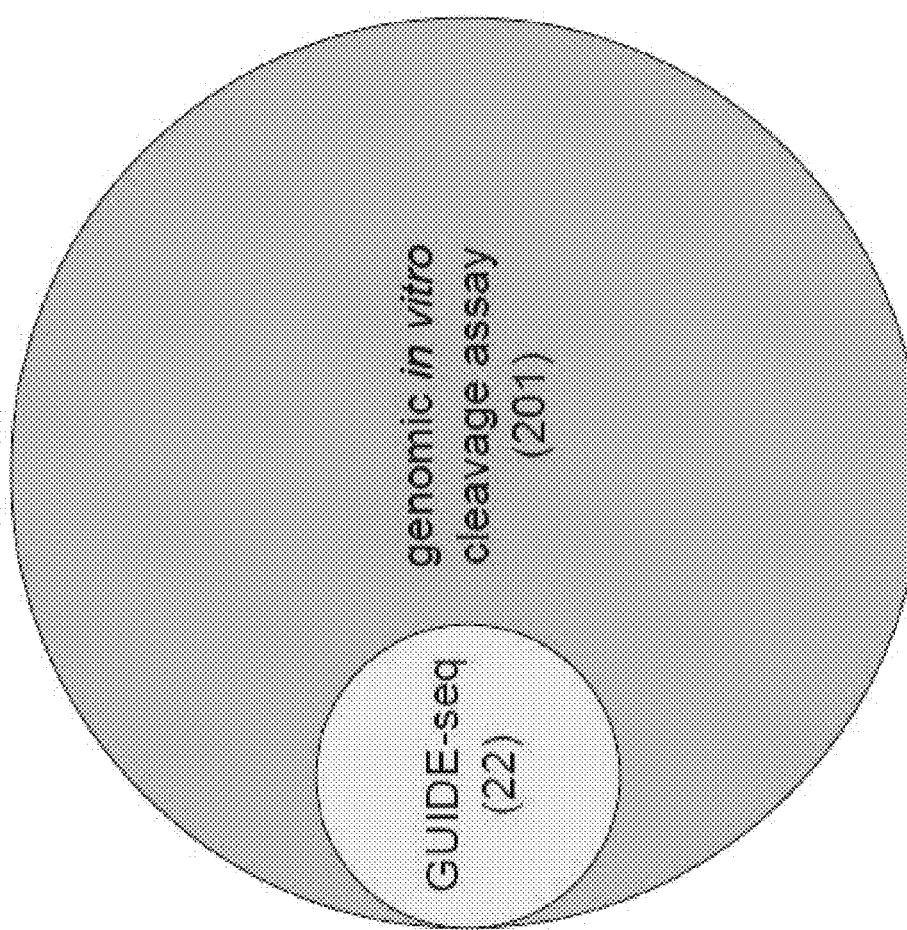
FIG. 6. Venn diagram of overlap between GUIDE-seq and FIND-seq genomic in vitro cleavage assay performed with 1 hour of lambda exonuclease and E. coli exonuclease I, and 1 hour of PlasmidSafe exonuclease treatment at the VEGFA target site 1. In this condition, 100% of GUIDE-seq sites are also detected with the in vitro assay.
Figure 7A:
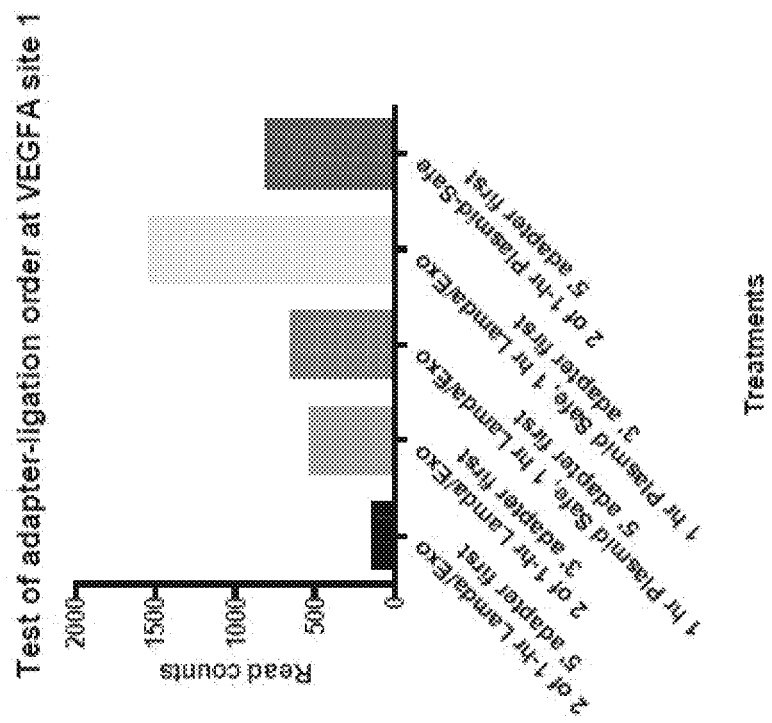
FIGS. 7A-B. Analysis of FIND-seq genomic in vitro cleavage assay testing the adapter ligation order with different exonuclease treatment conditions. The condition that detected the highest number of sites is 1 hr PlasmidSafe, 1 hr Lambda exonuclease/E. Coli exonuclease I treatment, with the 3' adapter added first. (a) Number of sites by FIND-seq genome-wide in vitro cleavage assay with different exonuclease treatments and adapter ligation order. (b) Read counts at FIND-seq detected off-target sites using different exonuclease treatments and adapter ligation order.
Figure 7B:
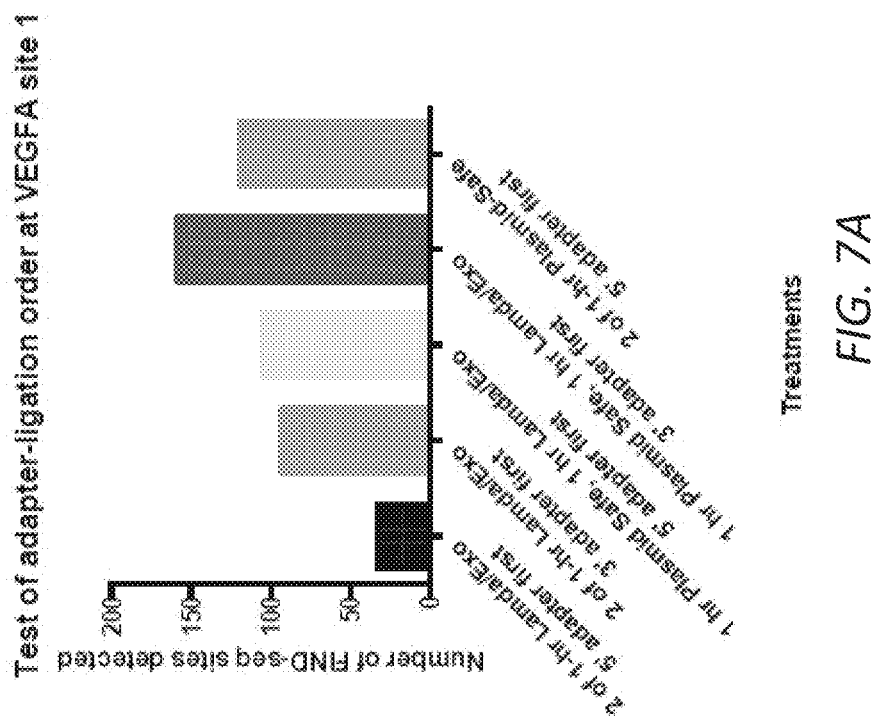

Using an optimized exonuclease treatment, the methods were again performed using CRISPR-Cas9 nuclease and a gRNA targeted to VEGFA site 1. This experiment yielded a larger number of off-target sites. Combining the various experiments performed with the VEGFA site 1 gRNA yields a larger number of off-target sites (FIGS. 5A-D). GUIDE-seq had previously been performed using this same VEGFA site 1 gRNA and a range of genome-wide off-target sites identified. Importantly, the present in vitro method performed with the optimized exonuclease treatment found ALL of the off-target sites previously identified by GUIDE-seq for the gRNA tested and a very large number of additional, previously unknown off-target sites as well (FIG. 6). This result demonstrates that these new methods are as sensitive as GUIDE-seq but offers the ability to identify sites that are not found by that earlier method. Reasons for this might include greater sensitivity of this in vitro method, negative biological selection against certain off-target mutations when practicing GUIDE-seq in cells, and/or negative effects of chromatin, DNA methylation, and gene expression on the activity of nucleases in cells.

Example 2. Exemplary FIND-Seq Protocol

Selection of Cleaved Amplicons for Next-Generation Sequencing (SCANS) In Vitro Assay for Finding Cleavage Sites of CRISPR/Cas9 Nuclease from Complex Genomic DNA Mixtures 1. End Repair (Red)

| Component | 1 rxn (ul) | 12 |
|---|---|---|
| Water | 8 | 115 |
| 10X Kapa End Repair Buffer | 7 | 101 |
| Kapa End Repair Enzyme Mix | 5 | 72 |
| Total master mix volume | 20 | 288 |
| Input DNA (0.1-5 ug) | 50 | |
| Total reaction volume | 70 | |

Incubate 30 minutes at 20 C.
1.7X SPRI cleanup using 120 ul Ampure XP beads.

2. A-Tailing (Blue)

| Component | 1 rxn (ul) | 12 |
|---|---|---|
| 10X Kapa A-Tailing Buffer | 5 | 72 |
| Kapa A-Tailing Enzyme | 3 | 43 |
| Total master mix volume | 8 | 115 |
| TE (0.1 mM EDTA) | 42 | |
| End repaired DNA with beads | 0 | |
| Total reaction volume | 50 | |

Incubate for 30 min at 30 C.
Cleanup by adding 90 ul of SPRI solution.

3. 5' Adapter Ligation (Yellow)

| Component | 1 rxn (ul) | 12 |
| --- | --- | --- |
| 5X Kapa Ligation Buffer | 10 | 144 |
| Kapa T4 DNA Ligase | 5 | 72 |
| Total master mix volume | 15 | 216 |
| A-tailed DNA with beads | 0 | |
| TE (0.1 mM EDTA) | 30 | |
| 5' Truseq Loop Adapter D50X (40 uM) | 5 | |
| Total reaction volume | 50 | |

Incubate for 1 hour at 20 C.
Cleanup by adding 50 ul of SPRI solution.

Proceed with 1 ug of 5' Adapter-ligated DNA into next step.

4. Exonuclease Treatment

| Component | 1 rxn (ul) | 12 |
| --- | --- | --- |
| 10X ExoI buffer | 5 | 72 |
| Lambda exonuclease (5 U/ul) | 4 | 58 |
| E. Coli Exonuclease I (20 U/ul) | 1 | 14 |
| Total master mix volume | 10 | 144 |
| Adapter-ligated DNA with beads | 0 | |
| TE (0.1 mM EDTA) | 40 | |
| Total reaction volume | 50 | |

Incubate for 1 hour at 37 C.
Cleanup by adding 50 ul of 1X Ampure XP beads.

5. Cleavage by Cas9

| Component | 1 rxn (ul) | 5 |
| --- | --- | --- |
| Water | 63 | 378 |
| 10X Cas9 buffer | 10 | 60 |
| Cas9 (1 uM ->900 nM final) | 9 | 54 |
| sgRNA (300 nM, ~100 ng/ul) | 3 | 18 |
| Total reaction volume | 85 | 510 |
| Incubate at room temperature for 10 minutes. | | |
| DNA (~400 bp, 250 ng) | 15 | |

Incubate for 1 hour at 37 C.
Purify with 1X SPRI bead cleanup (100 ul).

6. A-Tailing

| Component | 1 rxn (ul) | 5 |
| --- | --- | --- |
| 10X Kapa A-Tailing Buffer | 5 | 30 |
| Kapa A-Tailing Enzyme | 3 | 18 |
| Total master mix volume | 8 | 48 |
| TE (0.1 mM EDTA) | 42 | |
| End repaired DNA with beads | 0 | |
| Total reaction volume | 50 | |

Incubate for 30 min at 30 C.
Cleanup by adding 90 ul of SPRI solution.

7. 3' Adapter Ligation

| Component | 1 rxn (ul) | 5 |
| --- | --- | --- |
| 5X Kapa Ligation Buffer | 10 | 60 |
| Kapa T4 DNA Ligase | 5 | 30 |
| Total master mix volume | 15 | 90 |
| A-tailed DNA with beads | 0 | |
| TE (0.1 mM EDTA) | 30 | |
| 3' Truseq Loop Adapter D70X (40 uM) | 5 | |
| Total reaction volume | 50 | |

Incubate for 30 minutes at 20 C.
Cleanup by adding 50 ul of SPRI solution.

8. USER Enzyme Treatment
Add 3 ul of USER enzyme and treat for 30 minutes at 37 C. (Treatment is in TE 10 mM Tris, 0.1 mM EDTA.)
Purify with 1×SPRI solution (50 ul).

9. PCR Amplification
Amplify with Kapa Hifi manufacturer's protocol and primers oSQT1274/1275.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a library of covalently closed DNA fragments, the method comprising:
   providing DNA;
   randomly shearing the DNA to a defined average length to provide a population of DNA fragments;
   preparing the population of DNA fragments for end-ligation;
   ligating to the ends of the fragments a first hairpin adapter comprising a single stranded hairpin loop region comprising at least a single deoxyuridine and a first primer site, to prepare a population of ligated fragments; and
   purifying the ligated fragments using an exonuclease, thereby preparing a library of covalently closed DNA fragments.

2. The method of claim 1, wherein the first primer site is compatible for use in PCR priming and/or sequencing.

3. The method of claim 1, further comprising:
   contacting the library of covalently closed DNA fragments with a nuclease to induce double stranded breaks including site-specific breaks;
   ligating a second hairpin adapter comprising a single-stranded hairpin loop comprising at least a single deoxyuridine and a second primer site compatible for use with the first primer site in PCR priming and/or sequencing,
   contacting the library with an enzyme to nick the DNA at the deoxyuridine; and
   sequencing those fragments having a first and second hairpin adapter.

4. The method of claim 3, wherein the enzyme that nicks the DNA at the deoxyuridine is a uracil DNA glycosylase (UDG) or endonuclease VIII.

5. The method of claim 3, wherein treating the sample with a nuclease to induce double stranded breaks comprises contacting the sample with a Cas9 nuclease complexed with a specific guide RNA (gRNA).

6. The method of claim 3, wherein the nuclease that induces double stranded breaks is selected from the group consisting of meganucleases, MegaTALs, zinc-finger nucleases, transcription activator effector-like nucleases (TALEN), and Clustered Regularly Interspaced Short Palindromic Repeats (CRISPR)/Cas RNA-guided nucleases (CRISPR/Cas RGNs).

7. The method of claim 6, wherein the nuclease is a Cas9 nuclease, and the method also includes expressing in the cells a guide RNA that directs the Cas9 nuclease to a target sequence in the genome.

8. The method of claim 1, wherein the DNA is randomly sheared to an average length of 200-1000 bps.

9. The method of claim 1, wherein the DNA is genomic DNA isolated from a mammalian, plant, bacterial, or fungal cell.

10. The method of claim 1, wherein the DNA is synthetic.

11. The method of claim 1, wherein the first primer site in the first hairpin adapter comprises a next generation sequencing primer site, a randomized DNA barcode or unique molecular identifier (UMI).

12. A method of preparing a library of fragments comprising nuclease-induced double stranded breaks in DNA, the method comprising:
   providing DNA;
   randomly shearing the DNA to a defined average length;
   optionally end-repairing and then A-tailing the sheared DNA;
   ligating to the DNA a first hairpin adapter comprising:
   a first region of 10-20 nucleotides;
   a second region of 45-65 nucleotides that forms one or more single-stranded hairpin loops and comprises a first primer site compatible for use in PCR priming and/or sequencing; and
   a third region of 10-20 nucleotides that is complementary to the first region, with a single deoxyuridine nucleotide between the first and second regions;
   contacting the sample with one or more exonucleases, sufficient to degrade any DNA molecules that lack the first hairpin adapter ligated to both of their ends;
   treating the sample with a nuclease to induce double stranded breaks, including site-specific breaks, of the DNA;
   optionally end-repairing and then A-tailing the resulting ends;
   ligating a second hairpin adapter comprising a first region of 10-20 nucleotides; a second region of 40-60 nucleotides that forms one or more single-stranded hairpin loops and comprises a second primer compatible for use with the first primer site in PCR priming and/or sequencing; and a third region of 10-20 nucleotides that is complementary to the first region and that also contains a single deoxyuridine nucleotide between the second and third regions, to create a population wherein the DNA fragments that were cleaved by the nuclease have a first and second hairpin adapter ligated to their respective ends; thereby preparing a library of fragments wherein one end was created by a nuclease-induced double stranded break in the DNA.

13. The method of claim 12, further comprising:
   contacting the library with uracil DNA glycosylase (UDG) and/or endonuclease VIII to nick the DNA at the deoxyuridine.

14. The method of claim 12, wherein treating the sample with a nuclease to induce site-specific cleavage comprises contacting the sample with a Cas9 nuclease complexed with a specific guide RNA (gRNA).

15. A method for detecting nuclease-induced double stranded breaks (DSBs) in DNA, the method comprising:
providing DNA;
randomly shearing the DNA to a defined average length;
optionally end-repairing and then A-tailing the sheared DNA;
ligating a first hairpin adapter comprising:
a first region of 10-20 nucleotides;
a second region of 45-65 nucleotides that forms one or more single-stranded hairpin loops and comprises a first primer site compatible for use in PCR priming and/or sequencing; and
a third region of 10-20 nucleotides that is complementary to the first region, with a single deoxyuridine nucleotide between the first and second regions;
contacting the sample with one or more exonucleases, sufficient to degrade any DNA molecules that lack the first hairpin adapter ligated to both of their ends;
treating the sample with a nuclease to induce double stranded breaks, including site-specific breaks, of the DNA;
optionally end-repairing and then A-tailing the resulting cleaved ends;
ligating a second hairpin adapter comprising a first region of 10-20 nucleotides; a second region of 40-60 nucleotides that forms one or more single-stranded hairpin loops and comprises a second primer compatible for use with the first primer site in PCR priming and/or sequencing; and a third region of 10-20 nucleotides that is complementary to the first region, and that also contains a single deoxyuridine nucleotide between the second and third regions, to create a population wherein the DNA fragments that were cleaved by the nuclease have the first and second hairpin adapters ligated to their respective ends; thereby preparing a library of fragments comprising nuclease-induced double stranded breaks in the DNA, wherein one end was created by a nuclease-induced double stranded break in the DNA;
contacting the library with uracil DNA glycosylase (UDG) and/or endonuclease VIII, a DNA glycosylase-lyase to nick the DNA at the deoxyuridine; and
sequencing those fragments bearing a first and a second hairpin adapter;
thereby detecting DSBs induced by the nuclease.

16. The method of claim 15, wherein the nuclease is selected from the group consisting of meganucleases, Mega-TALs, zinc-finger nucleases, transcription activator effector-like nucleases (TALEN), and Clustered Regularly Interspaced Short Palindromic Repeats (CRISPR)/Cas RNA-guided nucleases (CRISPR/Cas RGNs).

17. The method of claim 15, wherein treating the sample with a nuclease to induce double stranded breaks comprises contacting the sample with a Cas9 nuclease complexed with a specific guide RNA (gRNA).

18. A method of determining which of a plurality of guide RNAs is most specific, the method comprising, for each of the plurality of guide RNAs:
providing DNA;
randomly shearing the DNA to a defined average length;
end-repairing and then A-tailing the sheared DNA;
ligating a first hairpin adapter comprising:
a first region of 10-20 nucleotides;
a second region of 45-65 nucleotides, that forms one or more single-stranded hairpin loops and comprises a first primer site compatible for use in PCR priming and/or sequencing; and
a third region of 10-20 nucleotides that is complementary to the first region, with a single deoxyuridine nucleotide between the first and second regions;
contacting the sample with one or more exonucleases, sufficient to degrade any DNA molecules that lack the first adapter ligated to both of their ends;
treating the sample with a Cas9 nuclease compatible with the guide RNA to induce site specific double stranded breaks of the DNA;
optionally end-repairing and then A-tailing the resulting cleaved ends;
ligating a second hairpin adapter comprising:
a first region of 10-20, nucleotides;
a second region of 40-60 nucleotides that forms one or more single-stranded hairpin loops and comprises a second primer compatible for use with the first primer site in PCR priming and/or sequencing; and
a third region of 10-20 nucleotides that is complementary to the first region, and that also contains a single deoxyuridine nucleotide between the second and third regions, to create a population wherein the DNA fragments that have a first and second hairpin adapter ligated to their ends are those that were cleaved by the nuclease; thereby preparing a library of fragments comprising nuclease-induced double stranded breaks in DNA wherein one end was created by a nuclease-induced double stranded break in the DNA;
contacting the library with uracil DNA glycosylase (UDG) and/or endonuclease VIII to nick the DNA at the deoxyuridine; and
sequencing those fragments bearing a first and a second hairpin adapter, thereby detecting DSBs induced by the nuclease in each sample;
optionally identifying whether each DSB is on-target or off-target;
comparing the DSBs induced by the nuclease in each sample; and
determining which of the plurality of guide RNAs induced the fewest off-target DSBs.

* * * * *

UNITED STATES PATENT AND TRADEMARK OFFICE
CERTIFICATE OF CORRECTION

PATENT NO. : 9,988,674 B2
APPLICATION NO. : 15/262972
DATED : June 5, 2018
INVENTOR(S) : J. Keith Joung and Shengdar Tsai Page 1 of 1

It is certified that error appears in the above-identified patent and that said Letters Patent is hereby corrected as shown below:

On the Title Page (*), Line 3, after "0 days." delete "days."

In the Claims

Column 278, Line 28 Claim 18, delete "10-20," and insert -- 10-20 --

Signed and Sealed this
Twenty-eighth Day of January, 2020

Andrei Iancu
*Director of the United States Patent and Trademark Office*

SEQUENCE LISTING

```
<160> NUMBER OF SEQ ID NOS: 766

<210> SEQ ID NO 1
<211> LENGTH: 83
<212> TYPE: DNA
<213> ORGANISM: Artificial Sequence
<220> FEATURE:
<223> OTHER INFORMATION: Description of Artificial Sequence: Synthetic
      oSQT1270 5'-Truseq-loop-adapter D501L primer
<220> FEATURE:
<223> OTHER INFORMATION: Description of Combined DNA/RNA Molecule:
      Synthetic oSQT1270 5'-Truseq-loop-adapter D501L primer

<400> SEQUENCE: 1
gatcggaaga gcuaatgata cggcgaccac cgagatctac actatagcct acactctttc    60
cctacacgac gctcttccga tct                                            83

<210> SEQ ID NO 2
<211> LENGTH: 83
<212> TYPE: DNA
```

<213> ORGANISM: Artificial Sequence
<220> FEATURE:
<223> OTHER INFORMATION: Description of Artificial Sequence: Synthetic
oSQT1302 5'-Truseq-loop-adapter D502L primer
<220> FEATURE:
<223> OTHER INFORMATION: Description of Combined DNA/RNA Molecule:
Synthetic oSQT1302 5'-Truseq-loop-adapter D502L primer

<400> SEQUENCE: 2
gatcggaaga gcuaatgata cggcgaccac cgagatctac acatagaggc acactctttc    60
cctacacgac gctcttccga tct                                           83

<210> SEQ ID NO 3
<211> LENGTH: 83
<212> TYPE: DNA
<213> ORGANISM: Artificial Sequence
<220> FEATURE:
<223> OTHER INFORMATION: Description of Artificial Sequence: Synthetic
oSQT1303 5'-Truseq-loop-adapter D503L primer
<220> FEATURE:
<223> OTHER INFORMATION: Description of Combined DNA/RNA Molecule:
Synthetic oSQT1303 5'-Truseq-loop-adapter D503L primer

<400> SEQUENCE: 3
gatcggaaga gcuaatgata cggcgaccac cgagatctac accctatcct acactctttc    60
cctacacgac gctcttccga tct                                           83

<210> SEQ ID NO 4
<211> LENGTH: 83
<212> TYPE: DNA
<213> ORGANISM: Artificial Sequence
<220> FEATURE:
<223> OTHER INFORMATION: Description of Artificial Sequence: Synthetic
oSQT1304 5'-Truseq-loop-adapter D504L primer
<220> FEATURE:
<223> OTHER INFORMATION: Description of Combined DNA/RNA Molecule:
Synthetic oSQT1304 5'-Truseq-loop-adapter D504L primer

<400> SEQUENCE: 4
gatcggaaga gcuaatgata cggcgaccac cgagatctac acggctctga acactctttc    60
cctacacgac gctcttccga tct                                           83

<210> SEQ ID NO 5
<211> LENGTH: 83
<212> TYPE: DNA
<213> ORGANISM: Artificial Sequence
<220> FEATURE:
<223> OTHER INFORMATION: Description of Artificial Sequence: Synthetic
oSQT1305 5'-Truseq-loop-adapter D505L primer
<220> FEATURE:
<223> OTHER INFORMATION: Description of Combined DNA/RNA Molecule:
Synthetic oSQT1305 5'-Truseq-loop-adapter D505L primer

<400> SEQUENCE: 5
gatcggaaga gcuaatgata cggcgaccac cgagatctac acaggcgaag acactctttc    60
cctacacgac gctcttccga tct                                           83

<210> SEQ ID NO 6
<211> LENGTH: 83
<212> TYPE: DNA
<213> ORGANISM: Artificial Sequence
<220> FEATURE:
<223> OTHER INFORMATION: Description of Artificial Sequence: Synthetic
oSQT1315 5'-Truseq-loop-adapter D506L primer
<220> FEATURE:
<223> OTHER INFORMATION: Description of Combined DNA/RNA Molecule:
Synthetic oSQT1315 5'-Truseq-loop-adapter D506L primer

<400> SEQUENCE: 6
gatcggaaga gcuaatgata cggcgaccac cgagatctac actaatctta acactctttc    60
cctacacgac gctcttccga tct    83

<210> SEQ ID NO 7
<211> LENGTH: 83
<212> TYPE: DNA
<213> ORGANISM: Artificial Sequence
<220> FEATURE:
<223> OTHER INFORMATION: Description of Artificial Sequence: Synthetic
      oSQT1316 5'-Truseq-loop-adapter D507L primer
<220> FEATURE:
<223> OTHER INFORMATION: Description of Combined DNA/RNA Molecule:
      Synthetic oSQT1316 5'-Truseq-loop-adapter D507L primer

<400> SEQUENCE: 7
gatcggaaga gcuaatgata cggcgaccac cgagatctac accaggacgt acactctttc    60
cctacacgac gctcttccga tct    83

<210> SEQ ID NO 8
<211> LENGTH: 83
<212> TYPE: DNA
<213> ORGANISM: Artificial Sequence
<220> FEATURE:
<223> OTHER INFORMATION: Description of Artificial Sequence: Synthetic
      oSQT1317 5'-Truseq-loop-adapter D508L primer
<220> FEATURE:
<223> OTHER INFORMATION: Description of Combined DNA/RNA Molecule:
      Synthetic oSQT1317 5'-Truseq-loop-adapter D508L primer

<400> SEQUENCE: 8
gatcggaaga gcuaatgata cggcgaccac cgagatctac acgtactgac acactctttc    60
cctacacgac gctcttccga tct    83

<210> SEQ ID NO 9
<211> LENGTH: 79
<212> TYPE: DNA
<213> ORGANISM: Artificial Sequence
<220> FEATURE:
<223> OTHER INFORMATION: Description of Artificial Sequence: Synthetic
      oSQT1271 3'-Truseq-loop-adapter D701L primer
<220> FEATURE:
<223> OTHER INFORMATION: Description of Combined DNA/RNA Molecule:
      Synthetic oSQT1271 3'-Truseq-loop-adapter D701L primer

<400> SEQUENCE: 9
gatcggaaga gcacacgtct gaactccagt cacattactc gatctcgtat gccgtcttct    60
gcttgugctc ttccgatct    79

<210> SEQ ID NO 10
<211> LENGTH: 79
<212> TYPE: DNA
<213> ORGANISM: Artificial Sequence
<220> FEATURE:
<223> OTHER INFORMATION: Description of Artificial Sequence: Synthetic
      oSQT1306 3'-Truseq-loop-adapter D702L primer
<220> FEATURE:
<223> OTHER INFORMATION: Description of Combined DNA/RNA Molecule:
      Synthetic oSQT1306 3'-Truseq-loop-adapter D702L primer

<400> SEQUENCE: 10
gatcggaaga gcacacgtct gaactccagt cactccggag aatctcgtat gccgtcttct    60
gcttgugctc ttccgatct    79

<210> SEQ ID NO 11
<211> LENGTH: 79
<212> TYPE: DNA
<213> ORGANISM: Artificial Sequence
<220> FEATURE:
<223> OTHER INFORMATION: Description of Artificial Sequence: Synthetic
oSQT1307 3'-Truseq-loop-adapter D703L primer
<220> FEATURE:
<223> OTHER INFORMATION: Description of Combined DNA/RNA Molecule:
Synthetic oSQT1307 3'-Truseq-loop-adapter D703L primer

<400> SEQUENCE: 11
gatcggaaga gcacacgtct gaactccagt caccgctcat tatctcgtat gccgtcttct    60
gcttgugctc ttccgatct                                                 79

<210> SEQ ID NO 12
<211> LENGTH: 79
<212> TYPE: DNA
<213> ORGANISM: Artificial Sequence
<220> FEATURE:
<223> OTHER INFORMATION: Description of Artificial Sequence: Synthetic
oSQT1308 3'-Truseq-loop-adapter D704L primer
<220> FEATURE:
<223> OTHER INFORMATION: Description of Combined DNA/RNA Molecule:
Synthetic oSQT1308 3'-Truseq-loop-adapter D704L primer

<400> SEQUENCE: 12
gatcggaaga gcacacgtct gaactccagt cacgagattc catctcgtat gccgtcttct    60
gcttgugctc ttccgatct                                                 79

<210> SEQ ID NO 13
<211> LENGTH: 79
<212> TYPE: DNA
<213> ORGANISM: Artificial Sequence
<220> FEATURE:
<223> OTHER INFORMATION: Description of Artificial Sequence: Synthetic
oSQT1309 3'-Truseq-loop-adapter D705L primer
<220> FEATURE:
<223> OTHER INFORMATION: Description of Combined DNA/RNA Molecule:
Synthetic oSQT1309 3'-Truseq-loop-adapter D705L primer

<400> SEQUENCE: 13
gatcggaaga gcacacgtct gaactccagt cacattcaga atctcgtat gccgtcttct     60 gcttgugctc ttccgatct                                                 79

<210> SEQ ID NO 14
<211> LENGTH: 79
<212> TYPE: DNA
<213> ORGANISM: Artificial Sequence
<220> FEATURE:
<223> OTHER INFORMATION: Description of Artificial Sequence: Synthetic
oSQT1318 3'-Truseq-loop-adapter D706L primer
<220> FEATURE:
<223> OTHER INFORMATION: Description of Combined DNA/RNA Molecule:
Synthetic oSQT1318 3'-Truseq-loop-adapter D706L primer

<400> SEQUENCE: 14
gatcggaaga gcacacgtct gaactccagt cacgaattcg tatctcgtat gccgtcttct    60
gcttgugctc ttccgatct                                                 79

<210> SEQ ID NO 15
<211> LENGTH: 79
<212> TYPE: DNA
<213> ORGANISM: Artificial Sequence
<220> FEATURE:
<223> OTHER INFORMATION: Description of Artificial Sequence: Synthetic oSQT1319 3'-Truseq-loop-adapter D707L primer
<220> FEATURE:
<223> OTHER INFORMATION: Description of Combined DNA/RNA Molecule:
    Synthetic oSQT1319 3'-Truseq-loop-adapter D707L primer

<400> SEQUENCE: 15
gatcggaaga gcacacgtct gaactccagt cacctgaagc tatctcgtat gccgtcttct    60
gcttgugctc ttccgatct                                                 79

<210> SEQ ID NO 16
<211> LENGTH: 79
<212> TYPE: DNA
<213> ORGANISM: Artificial Sequence
<220> FEATURE:
<223> OTHER INFORMATION: Description of Artificial Sequence: Synthetic
    oSQT1320 3'-Truseq-loop-adapter D708L primer
<220> FEATURE:
<223> OTHER INFORMATION: Description of Combined DNA/RNA Molecule:
    Synthetic oSQT1320 3'-Truseq-loop-adapter D708L primer

<400> SEQUENCE: 16
gatcggaaga gcacacgtct gaactccagt cactaatgcg catctcgtat gccgtcttct    60
gcttgugctc ttccgatct                                                 79

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
    oSQT1274 Truseq F1 primer

<400> SEQUENCE: 17
aatgatacgg cgaccaccga g                                              21

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
    oSQT1275 Truseq R1 primer

<400> SEQUENCE: 18
caagcagaag acggcatacg agat                                           24

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
    VEGFA site1 oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 19
gggtgggggg agtttgctcc ngg                                            23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic VEGFA site2 oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 20
gaccccctcc acccgcctc ngg                                              23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site3 oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 21
ggtgagtgag tgtgtgcgtg ngg                                             23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1 site oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 22
gagtccgagc agaagaagaa ngg                                             23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_on_target_sequence
<220> FEATURE:
<221> NAME/KEY: modified_base
<222> LOCATION: (21)..(21)
<223> OTHER INFORMATION: a, c, t, g, unknown or other

<400> SEQUENCE: 23
gagtccgagc agaagaagaa ngg                                             23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 24
gagttagagc agaagaagaa agg                                             23

<210> SEQ ID NO 25
<211> LENGTH: 23
<212> TYPE: DNA
<213> ORGANISM: Artificial Sequence

```
<220> FEATURE:
<223> OTHER INFORMATION: Description of Artificial Sequence: Synthetic
      EMX1_offtarget_sequence

<400> SEQUENCE: 25
aagtccgagg agaggaagaa agg                                              23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 26
gagcctgagc agaaggagaa ggg                                              23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 27
gaggccgagc agaagaaaga cgg                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 28
gagtaagaga agaagaagaa ggg                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 29
aagtctgagc acaagaagaa tgg                                              23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 30
gagccggagc agaagaagga ggg                                              23

<210> SEQ ID NO 31
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      EMX1_offtarget_sequence

<400> SEQUENCE: 31
acgtctgagc agaagaagaa tgg                                            23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 32
gagtcctagc aggagaagaa gag                                            23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 33
gagtctaagc agaagaagaa gag                                            23

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 34
gagtccaagc agtagaggaa ggg                                            23

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 35
gagcacgagc aagagaagaa ggg                                            23

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 36
aagcccgagc aaaggaagaa agg                                            23

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued

```
      EMX1_offtarget_sequence

<400> SEQUENCE: 37
aaatccaacc agaagaagaa agg                                           23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 38
aggtcagagc agaagaaaag agg                                           23

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 39
aaggccaagc agaagagtaa tgg                                           23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 40
agttccaagc agaggaagaa ggg                                           23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      EMX1_offtarget_sequence

<400> SEQUENCE: 41
aggtctgagc agaagaggaa gag                                           23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_on_target_sequence
<220> FEATURE:
<221> NAME/KEY: modified_base
<222> LOCATION: (21)..(21)
<223> OTHER INFORMATION: a, c, t, g, unknown or other

<400> SEQUENCE: 42
gggtgggggg agtttgctcc ngg                                           23

<210> SEQ ID NO 43
<211> LENGTH: 23
<212> TYPE: DNA
```

<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 43
gggtgggggg agtttgcccc agg                                              23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 44
gcgtgggggg tgtttgctcc cgg                                              23

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 45
gggagggtgg agtttgctcc tgg                                              23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 46
ggatggaggg agtttgctcc tgg                                              23

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 47
ggggaggggA agtttgctcc tgg                                              23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 48
cgggggaggg agtttgctcc tgg                                              23

<210> SEQ ID NO 49
<211> LENGTH: 23
<212> TYPE: DNA
<213> ORGANISM: Artificial Sequence

```
<220> FEATURE:
<223> OTHER INFORMATION: Description of Artificial Sequence: Synthetic
      VEGFA site 1_offtarget_sequence

<400> SEQUENCE: 49
gggggtgggg actttgctcc agg                                              23

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 50
gtgtgagtgg agtttgctct ggg                                              23

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 51
aggtggtggg agcttgttcc tgg                                              23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 52
gagggtgggg agtttactcc tgg                                              23

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 53
ggtgggggtg ggtttgctcc tgg                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 54
gggagcaggg aatttgctcc agg                                              23

<210> SEQ ID NO 55
<211> LENGTH: 23
<212> TYPE: DNA
<213> ORGANISM: Artificial Sequence
<220> FEATURE:
```

<223> OTHER INFORMATION: Description of Artificial Sequence: Synthetic
      VEGFA site 1_offtarget_sequence

<400> SEQUENCE: 55 ttggggggc agtttgctcc tgg                                              23

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 56
gtgggggtag agtttgctcc agg                                              23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 57
atgtgtgggg aatttgctcc agg                                              23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 58
ggatggaggt agtttgttcc tgg                                              23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 59
agctggaggg agtttgcccc agg                                              23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 60
ggctggaggg gatttgctcc tgg                                              23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic VEGFA site 1_offtarget_sequence

<400> SEQUENCE: 61
agtttggggg agtttgcccc agg                                              23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 62
tagtggaggg agcttgctcc tgg                                              23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 63
gggggcaggg agattgctcc tgg                                              23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 64 gaggggagc agtttgctcc agg                                               23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 65
agggagggag aatttgctcc tgg                                              23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 66
aggaaggagg agttagctcc tgg                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 67
aggaaggagg agttagctcc tgg                                              23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 68
aggaaggagg agttagctcc tgg                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 69
aggaaggagg agttagctcc tgg                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 70
tcttgggggg aagttgctcc agg                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 71
aagtaaggga agtttgctcc tgg                                              23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 72
gtgcaggggg aatttgcttc cgg                                              23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence -continued

<400> SEQUENCE: 73
agggaggagg aatttgctcc agg                                              23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 74
aagtgggaag agtttgttcc agg                                              23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 75
ggaaaggagg agcttgctcc agg                                              23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 76
agtgggggag agtatgctcc ggg                                              23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 77
cccgggggga agcttgctcc agg                                              23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 78
gggaggagag agtttgctct ctg                                              23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 79 ctggtgggggg agcttgctcc agg                                              23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 80
acggtggggg aatttgctcc tga                                               23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_offtarget_sequence

<400> SEQUENCE: 81
gaggggggag ggattgcttt agg                                               23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_on_target_sequence
<220> FEATURE:
<221> NAME/KEY: modified_base
<222> LOCATION: (21)..(21)
<223> OTHER INFORMATION: a, c, t, g, unknown or other

<400> SEQUENCE: 82
gaccccctcc acccgcctc ngg                                                23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 83 gaccccccc acccgcccc cgg                                                 23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 84
gaccctgtcc accccacctc agg                                               23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic VEGFA site 2_offtarget_sequence

<400> SEQUENCE: 85
ggccccctcc tcctcgcctc tgg                                              23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 86
aaccccatcc acccggcctc agg                                              23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 87
ctacccctcc accccgcctc cgg                                              23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 88 cacccctca acaccgcctc agg                                               23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 89 gaccctccc accccgactc cgg                                               23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 90
gacccactgc acccagcctc agg                                              23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 91
gggcccctcc accccgcctc tgg                                              23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 92
caccccctcc cctccgcctc agg                                              23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 93
gacaccttcc accccgtctc tgg                                              23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 94
taccccccac accccgcctc tgg                                              23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 95
gccccgctcc tcccgcctc cgg                                               23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 96
gcccccaccc accccgcctc tgg                                              23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

```
<400> SEQUENCE: 97
gccccccacc accccacctc ggg                                              23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 98
gtccccctcc tccccacctc cgg                                              23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 99
tgccccctcc ccccagcctc tgg                                              23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 100 gaccoctccc tccccacctc agg                                              23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 101
gccaccttcc accccacctc agg                                              23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 102
ggccctctcc actccacctc agg                                              23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 103
```
gacacacccc accccacctc agg                                          23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 104 tactccccc acccagcctc agg                                           23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 105
cccccccccc accccgcccc cgg                                          23

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 106 attcccccc accccgcctc agg                                           23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 107
agtcccctcc accctcctc agg                                           23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 108 gaccoctacc accccatctc agg                                          23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 109 gtcccctcc tccctgtctc agg                                               23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 110 caacccccc accccgcttc agg                                               23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 111 caccacccc accccgcccc tgg                                               23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 112
gcccccccca accccgcccc cgg                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 113
ctccccaccc accccgcctc agg                                              23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 114
gccgcccccc actccgcctc cgg                                              23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 115
ctcccccccc tcccgcctc ggg                                               23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 116 gacccccacct accccacctc agg                                          23

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 117
gacacacccc ccccgcctc cgg                                            23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 118 ctcccctcc tcccgtctc ggg                                             23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 119
ggcccactcc actccgtctc cgg                                           23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 120
aacctccacc tccccgcctc agg                                           23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 121 gacaccccccc accccactc agg                                           23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 122
gaccccctcc tccccggcct cgg                                              23

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 123
gtcccctccc tccccgcctc tgg                                              23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 124
acaccccccc accccgcctc agg                                              23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 125 cactccccccc accccgcccc agg                                             23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 126
aagccccccc accccgcccc ggg                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 127
ccccaccccc accccgcctc agg                                              23

```
<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 128 agccccccc accccgactc agg                                              23

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 129
cgccctcccc accccgcctc cgg                                             23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 130
ggctccctcc gccccgcccc ggg                                             23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 131
cacccccccc cccccacctc cgg                                             23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 132
gtcactcccc accccgcctc tgg                                             23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 133 ttcccectcc tcccagcctc tgg                                             23

<210> SEQ ID NO 134
```

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 134
gccacccacc accccacctc agg                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 135
cccccccccc ccccgcctc agg                                               23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 136
gtcccctccc accccgcctc cag                                              23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 137 tgccccccccc accccacctc tgg                                             23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 138
ctcccccgcc accccgcccc agg                                              23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 139 tgccccctccc accccgcctc tgg                                             23

<210> SEQ ID NO 140
<211> LENGTH: 23

```
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 140
ccgcccctcc accccgccac tgg                                           23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 141
actcccctcc accccggctc ggg                                           23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 142
ttccccttcc acccagcctc tgg                                           23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 143
gagctccccc accccgcccc ggg                                           23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 144
agcccccccc accccgcccc tgg                                           23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 145
ttctccctcc tcccgcctc ggg                                            23

<210> SEQ ID NO 146
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 146
ctccccctcc ccccagcctc tgg                                              23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 147
agcccccacc tccccgcctc ggg                                              23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 148 gcccccacc accccacccc cgg                                               23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 149
tgcccccccc accccgcccc cgg                                              23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 150
tggcccctcc gccccacctc tgg                                              23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 151
tacccctgcc accccatctc tgg                                              23

<210> SEQ ID NO 152
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      VEGFA site 2_offtarget_sequence

<400> SEQUENCE: 152
aaccccaccc accccatctc agg                                              23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 153
ccacccctcc cacccgcctc tgg                                              23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 154
ctccctcccc accccacctc tgg                                              23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 155 acccccccccc cccccgcccc cgg                                             23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 156
tcctccttcc actccgcctc tgg                                              23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 157 ttcccccccca accccacctc ggg                                             23

<210> SEQ ID NO 158
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      VEGFA site 2_offtarget_sequence

<400> SEQUENCE: 158
gcccccacca gccccgcctc ggg                                            23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 159
ccaccccccc accccgcccc agg                                            23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 160
ttcccactcc acccccttc tgg                                             23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 161
tctcccctcc ccctcgcctc tgg                                            23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 162
cccccccccc ccccgcccc ggg                                             23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 163
tggtccctcc accccgccgc cgg                                            23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
```

VEGFA site 2_offtarget_sequence

<400> SEQUENCE: 164
cttcccctcc ccccgcccc cgg                                        23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 165
gatcctccca actccgcctc tgg                                       23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 166
ctcctcctcc gcccgcccc ggg                                        23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 167
aggcccccac accccgcctc agg                                       23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 168 agaccctgc ccccgcctc cgg                                         23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 169
tgcaccctcc gcccgcccc cgg                                        23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 170 tgcaccccc accccgcccc tgg                                          23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 171
ttcccccagc accccgccta ggg                                          23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 172
gccccacccc actccacctc tgg                                          23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 173 tccaccccc accccgcccc ggg                                           23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 174
actccccgcc accccgcccc tgg                                          23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 175
ccctcccccc gccccgcctc cgg                                          23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 176
gtaccccacc accccgcccc agg    23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 177
ggctcacccc accccacctc tgg    23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 178
tccccccacc accccacccc cgg    23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 179
catctccccc accccacctc agg    23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 180
cccccacccc accccgcctc cag    23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 181
tcacccctcc ccctcgcctc tgg    23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 182
cactccccac accccacctc agg                                        23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 183
tccacccccc acccagcctc cgg                                        23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 184 aggcccccccc gccccgcctc agg                                       23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 185 ctcaccccccc accccacctc tgg                                       23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 186
gcttccctcc accccgcatc cgg                                        23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 187
tgtcccctct accccgcttc agg                                        23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 188
acctccctcc acctcacctc cgg                                              23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 189
tctcccctcc accccgccct cgg                                              23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 190
cacctccaca actccgcctc tgg                                              23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 191
ttctccctcc gccccgcccc tgg                                              23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 192
accccacccc acccagcctc tgg                                              23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 193 ttcccccca accccacctc ggg                                               23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 194
tctcccctgt accccgcctc tgg                                              23

```
<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 195
accaccctcc gcccgcctc cag                                              23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 196
caccccctcc accctgcct cgg                                              23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 197 ccccgcccc accccacctc agg                                              23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 198
tccccacccc gcccgcctc tgg                                              23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 199
ctttccctcc acccagcctc tgg                                             23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 200
tttcccttcc acccagcctc tgg                                             23
```

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 201 tccgccccc accccacctc cgg                                              23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 202
tatcctcccc accccgcccc ggg                                             23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 203
acccccctac accccaccac cgg                                             23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 204
cccccccccc ccccgcccc ggg                                              23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 205
tctcccctcc ccctcgcctc tgg                                             23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 206
cgcccacccc accccacctc agg                                             23

```
<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 207
aatccccact accccacctc tgg                                              23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 208
ttcccactcc atcccgcttc tgg                                              23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 209
accccacccc accccgtctc cgg                                              23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 210
tcacccctct tccccgcctc ggg                                              23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 211
cccccccctc accccgcccc tgg                                              23

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 212 aacaccccccc accccacccc ggg                                             23

<210> SEQ ID NO 213
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 213
ccaccccccc accccgcccc tgg                                            23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 214
tgcccccttc tccccgcccc tgg                                            23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 215 tccccccctca gccccgcccc agg                                           23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 216
ctcccccagc ccccgcctc cgg                                             23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 217 ctgcccccc accccgccac tgg                                             23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 218 tccccctcc accccgccc ccg                                              23

<210> SEQ ID NO 219
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 219
taaatcctcc accccacctc agg                                           23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 220
actacccacc tccccgcctc agg                                           23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 221
cctcccccac accccgcatc cgg                                           23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 222 accccgcca tccccgcctc agg                                            23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 223
cctccccaac accccgcccc ggg                                           23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 224
tccccacccc accccacccc cgg                                           23

<210> SEQ ID NO 225
<211> LENGTH: 23
<212> TYPE: DNA
```

<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 225
cttcccccac accccgcccc agg                                          23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 226 cataccccc accccgcccc ggg                                           23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 227 atccctccc accccgcaac cgg                                           23

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 228
tcactccccc accccacctc tgg                                          23

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 229
cccccccccc gccccgcccc ccg                                          23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 230
gctactctcc accccacctc tgg                                          23

<210> SEQ ID NO 231
<211> LENGTH: 23
<212> TYPE: DNA
<213> ORGANISM: Artificial Sequence

```
<220> FEATURE:
<223> OTHER INFORMATION: Description of Artificial Sequence: Synthetic
      VEGFA site 2_offtarget_sequence

<400> SEQUENCE: 231
atctccccac accccgcctt cgg                                              23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 232 acccccccc cacccgcccc cgg                                               23

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 233
ccgctcctcc accccacctc gag                                              23

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 234
ccctcccccc accccacatc agg                                              23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 235
acaccgctcc accccgcttc cag                                              23

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 236
ctgccccccc accccaactc agg                                              23

<210> SEQ ID NO 237
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      VEGFA site 2_offtarget_sequence

<400> SEQUENCE: 237
cggcctcccc accccgcccc cgg                                              23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 238
ggccccaccc accccgcctt ctg                                              23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 239
attcaccccc accccgactc tgg                                              23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 240
cagtcccccc accccacctc tgg                                              23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 241
actcccaccc accccacctc agg                                              23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 242 ctaccccccac tccccgcctc cgg                                             23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
```

VEGFA site 2_offtarget_sequence

<400> SEQUENCE: 243
acaccctccc accccgcttc tgg                                              23

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 244
cattcccccc accccacctc agg                                              23

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 245 cctcacccccc accccacctc tgg                                             23

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 246
aggccctccc accccgcatc agg                                              23

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 247
atgccccacc ccccgcccc cgg                                               23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 248 tttcccccccc accccaactc agg                                             23

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 249
cctccccaac ccccgcctc aag                                              23

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 250
cccccacccc ccccaccccc tgg                                             23

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 251
cgtctccccc ccccacctc agg                                              23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 252
tctctcctcc ccccacatc agg                                              23

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 253 ccccacccccc ccccatctc tgg                                             23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 254 aagaccccccc ccccgcccc agg                                             23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 255 atgtccccccc tccccgcctc ggg                                              23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 256
ggctccctcc gctccaaccc agg                                               23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 257
ctcccctcca ccccagcctc cgg                                               23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 258 cttgccccccc ccccaccctc ggg                                              23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 259
ttcccccacc acccgccct ccg                                                23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 260
cttatccccc accccaccctc agg                                              23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 261 acaccccccca ccccaccctc tgg                                                  23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 262
cctcctcccc gccccgcctc cgc                                                   23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 263
cgccctcccc attccgcccc ggg                                                   23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 2_offtarget_sequence

<400> SEQUENCE: 264 tccccccac ccccgacctc agg                                                    23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_on_target_sequence
<220> FEATURE:
<221> NAME/KEY: modified_base
<222> LOCATION: (21)..(21)
<223> OTHER INFORMATION: a, c, t, g, unknown or other

<400> SEQUENCE: 265
ggtgagtgag tgtgtgcgtg ngg                                                   23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 266
ggtgagtgag tgtgtgtgtg agg                                                   23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic VEGFA site 3_offtarget_sequence

<400> SEQUENCE: 267
agtgtgtgag tgtgtgcgtg tgg								23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 268
gctgagtgag tgtatgcgtg tgg								23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 269
ggtgtgtgag tgtgtgtgtg tgg								23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 270
ggtgagtgtg tgtgtgcatg tgg								23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 271
tgtgggtgag tgtgtgcgtg agg								23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 272
ggtgagtgag agtgtgtgtg tgg								23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 273
ggtgagtgag tgcgtgcggg tgg                                          23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 274
gttgagtgaa tgtgtgcgtg agg                                          23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 275
agtgagtgag tgtgtgtgtg ggg                                          23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 276
tgtgtgtgag tgtgtgtgtg tgg                                          23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 277
tgtatgtgag tgtgtgcgtg tgg                                          23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 278
tgtgagtggg tgtgtgcatg tgg                                          23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 279 gggggggtgag tgtgtgtgtg ggg     23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 280
tgtgtgtgag tgtgtgtgtg ggg     23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 281
tgtgagagag agtgtgcgtg tgg     23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 282
tgtgggtgag tgtgtgtgtg tgg     23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 283
tgtgtgtgag tgtgtgtgtg tgg     23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 284
tgtgagtgtg tgtgtgtgtg tgg     23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 285
agtgaatgag tgtgtgtgtg tgg                                    23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 286
tgtgtgtgag tgtgtgtgtg tgg                                    23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 287
gatgtgtgag tgtgtgcctg tgg                                    23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 288
ggtgagcaag tgtgtgtgtg tgg                                    23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 289
tgtgtgtgag tgtgtgtgtg ggg                                    23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 290
tgtgtgtgag tgtgtgtgtg tgg                                    23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 291
tgtgagtgag tgtgtgtatg ggg                                              23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 292
agagagtgag tgtgtgcatg agg                                              23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 293
ggtgtgtggg tgtgtgtgtg ggg                                              23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 294
ggtgggtgtg tgtgtgtgtg ggg                                              23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 295
gatgagtgtg tgtgtgtgtg agg                                              23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 296
tgtgtgtgag tgtgtgtgtg tgg                                              23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 297
tgtgggtggg tgtgtgcgtg tgg                                              23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 298
ggtgtgtgag tgtatgtgtg tgg                                          23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 299
tgtgtgtgag tgtgtgtgtg tgg                                          23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 300
tgtgtgtgag tgtgtgtgtg tgg                                          23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 301
tgtgtgtgag tgtgtgcatg tgg                                          23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 302
ggtgtgtgag tgtgtgcatt ggg                                          23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 303
tgtgtgtgag tgtgtgtgtg tgg                                          23

```
<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 304
tgtgtgtgag tgtgtgtgtg tgg                                              23

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 305
agcgagtgag tgtgtgtgtg ggg                                              23

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 306
tgtgtgtgag tgtgtgtgtg tgg                                              23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 307
tgtgtgtgag tgtgtgtgtg agg                                              23

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 308
ggtgggtgtg tgtgtgtgtg tgg                                              23

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 309
ggtgtatgag tgtgtgtgtg agg                                              23
```

-continued

```
<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 310
cgtgtgtgag tgtgtgtgtg ggg                                              23

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 311
tgtgtgtgag tgtgtgtgtg ggg                                              23

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 312
tgtgtgtgag tgtgtgtgtg tgg                                              23

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 313
tgtgagtgtg tgtgtgcatg tgg                                              23

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 314
tgtgtgtgag tgtgtgtgtg ggg                                              23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 315
tgtgtgtgag tgtgtgcatg agg                                              23

<210> SEQ ID NO 316
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 316
tgtgtgtgag tgtgtgtgtg ggg                                          23

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 317
agtgagtgag tgagtgagtg ggg                                          23

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 318
tgtgagtgcg tgtgtgtgtg tgg                                          23

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 319
tgtgtgtgag tgtgtgtgtg ggg                                          23

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 320
tgagtgtgag tgtgtgcgtg ggg                                          23

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 321
agggagtgac tgtgtgcgtg tgg                                          23

<210> SEQ ID NO 322
<211> LENGTH: 23
```

-continued

```
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 322
ggtggatgag tgtgtgtgtg ggg                                          23

<210> SEQ ID NO 323
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 323
gatgagtgtg tgtgtgtgtg cgg                                          23

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 324
tgtgaatgtg tgtgtgcgtg tgg                                          23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 325
tgtgtgtgag tgtgtgtgtg tgg                                          23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 326
tgtgtgtgag tgtgtgtgtg tgg                                          23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 327
tgtgagtaag tgtgtgtgtg tgg                                          23

<210> SEQ ID NO 328
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 328
tgtgagtgtg tgtgtgtgtg ggg                                          23

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 329
agcgagtggg tgtgtgcgtg ggg                                          23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 330
tgtgagtgtg tgtgtgtgtg tgg                                          23

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 331
tgtgtgtgag tgtgtgtgtg tgg                                          23

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 332
ggtaagtgtg tgtgtgcatg tgg                                          23

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 333
agtgagtgag tgtgtgtgtg tga                                          23

<210> SEQ ID NO 334
<211> LENGTH: 23
<212> TYPE: DNA
<213> ORGANISM: Artificial Sequence
```

-continued

```
<220> FEATURE:
<223> OTHER INFORMATION: Description of Artificial Sequence: Synthetic
      VEGFA site 3_offtarget_sequence

<400> SEQUENCE: 334
catgagtgag tgtgtgggtg ggg                                              23

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 335
tgtgagtggg tgtgtgtgtg ggg                                              23

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 336
actgtgtgag tgtgtgcgtg agg                                              23

<210> SEQ ID NO 337
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 337
tgtgagtgaa tgtgtgtgtg tgg                                              23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 338
cgtgagtgtg tgtatgcgtg tgg                                              23

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 339
tgtgagtggg tgtgtgtgtg tgg                                              23

<210> SEQ ID NO 340
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      VEGFA site 3_offtarget_sequence

<400> SEQUENCE: 340
agagagagag tgtgtgtgtg tgg                                          23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 341
agagagagag tgtgtgtgtg tgg                                          23

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 342
agtgtgtgag tgtgtgtatg agg                                          23

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 343
agtgagtgtg tgtgtgtgtg tgt                                          23

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 344
tgtgagtgtg tgtgtgtgtg tgt                                          23

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 345
tctaagtgag tgtgtgtgtg tgg                                          23

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
```

VEGFA site 3_offtarget_sequence

<400> SEQUENCE: 346
agagagagag tgtgtgtgtg tgg                                              23

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 347
agagagagag tgtgtgtgtg tgg                                              23

<210> SEQ ID NO 348
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 348
agagagagag tgtgtgtgtg ggg                                              23

<210> SEQ ID NO 349
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 349
actgagtgag tgtgagtgtg agg                                              23

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 350
agtgagaaag tgtgtgcatg cgg                                              23

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 351
agggagtgag tgtgtaagtg tgg                                              23

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

```
<400> SEQUENCE: 352
tgtgtgtgag tgtgtgtggg ggg                                            23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 353
agagagagag tgtgtgtgtg tgg                                            23

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 354
catgcgtgag tgtgtgcatg ggg                                            23

<210> SEQ ID NO 355
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 355
tgtgaatgtg tgtgtgcatg tgg                                            23

<210> SEQ ID NO 356
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 356
tgtgagtgta tgtgtgtgtg tgg                                            23

<210> SEQ ID NO 357
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 357
tgtgaaggag tgtgtgtgtg tgg                                            23

<210> SEQ ID NO 358
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence
```

```
<400> SEQUENCE: 358
tgtaagagag tgtgtgtgtg ggg                                             23

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 359
ggcggatgag tgtgtgtgtg tgg                                             23

<210> SEQ ID NO 360
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 360
agggagtgag tgtgagagtg cgg                                             23

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 361
tgtgagtgta tgtgtgtgtg agg                                             23

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 362
agagagagag tgtgtgtgtg tgg                                             23

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 363
gtagagtgag tgtgtgtgtg tgg                                             23

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 364
```
tgtgagtatg tgtgtgcatg tgg                                              23

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 365
tgtgagtggg tgtgtatgtg agg                                              23

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 366
catgagtgac tgtgtgtgtg tgg                                              23

<210> SEQ ID NO 367
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 367
attgagtgag tatgtgtgtg agg                                              23

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 368
tgtgatagag tgtgtgtgtg agg                                              23

<210> SEQ ID NO 369
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 369
tgtgtgtgag tgtgtgtgtg tgt                                              23

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 370
agtgagtatg tgtgtgtgtg ggg                                              23

<210> SEQ ID NO 371
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 371
agagagagag tgtgtgtgtg agg                                              23

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 372
gataagtgag tatgtgtgtg tgg                                              23

<210> SEQ ID NO 373
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 373
ggagaatagg tgtgtgcgtg ggg                                              23

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 374
tgtgtatgag tgtgtgtgtg tgg                                              23

<210> SEQ ID NO 375
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 375
agagagagag tgtgtgtgtg agg                                              23

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 376
tgtgagtgta tgtgtgtgtg ggg                                              23

<210> SEQ ID NO 377
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 377
tgtgagtatg tgtgtgtgtg tgg                                              23

<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 378
tgtgagtgag tatgtacatg tgg                                              23

<210> SEQ ID NO 379
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 379
cgtgagtgtg tgtgtgtgtg ggt                                              23

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 380
ctggagtgag tgtgtgtgtg tgg                                              23

<210> SEQ ID NO 381
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 381
agggaatgag tgtgtgtgtg tgg                                              23

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 382
tgtgcgtgag tgtgtgtgtg tat                                              23

<210> SEQ ID NO 383
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 383
gaagagtaag tgtgtgtgtg ggg                                   23

<210> SEQ ID NO 384
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 384
gcagagtgag tgtgtgtgtt ggg                                   23

<210> SEQ ID NO 385
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 385
aatgaatgaa tgtgtgcatg tgg                                   23

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 386
taagagtgag tgtgtgtgtg gtg                                   23

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 387
gtgtagtgag tgtatgtgtg agg                                   23

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 388
tgcatgtgag tgtgtgtgtg tgg                                   23

```
<210> SEQ ID NO 389
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 3_offtarget_sequence

<400> SEQUENCE: 389
cgtgtgtgtg tgtgtgtgtg tat                                              23

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_on_target_sequence

<400> SEQUENCE: 390
gggtgggggg agtttgctcc tgg                                              23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 391
gggtgggggg agtttgcccc agg                                              23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 392
gggtgggggg agtttgcccc agg                                              23

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 393
gcgtgggggg tgtttgctcc cgg                                              23

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 394
ggatggaggg agtttgctcc tgg                                              23

<210> SEQ ID NO 395
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 395
gggagggtgg agtttgctcc tgg                                               23

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 396
gggtgggtgg agtttgctac tgg                                               23

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 397 cgggggagggg agtttgctcc tgg                                              23

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 398
gggggtgggg actttgctcc agg                                               23

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 399
ggggagggga agtttgctcc tgg                                               23

<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 400
gtgtgggtgg cgtttgctcc agg                                               23

<210> SEQ ID NO 401
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 401
ggttgagggg agtctgctcc agg                                              23

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 402
tggtgggggg agcttgctcc ctg                                              23

<210> SEQ ID NO 403
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 403
gggtggggag agtttcttcc tgg                                              23

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 404 gggaggggc aggttgctcc agg                                               23

<210> SEQ ID NO 405
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 405
gggtggggga agtaggctcc cgg                                              23

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 406
gagtgggtgg agtttgctac agg                                              23

<210> SEQ ID NO 407
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 407
gggtggggga aggtagctcc agg                                              23

<210> SEQ ID NO 408
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 408
gggtgggggg aacttgttcc agg                                              23

<210> SEQ ID NO 409
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 409
gggaggggag agtttgttcc agg                                              23

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 410
gggtgggggg agcttgtccc tgg                                              23

<210> SEQ ID NO 411
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 411
gggaggggag agtgtgttcc ggg                                              23

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 412
gggtgggagg agtctgcccc agg                                              23

<210> SEQ ID NO 413
<211> LENGTH: 23
<212> TYPE: DNA
<213> ORGANISM: Artificial Sequence
```

<220> FEATURE:
<223> OTHER INFORMATION: Description of Artificial Sequence: Synthetic
      VEGFA site 1_off_target_sequence

<400> SEQUENCE: 413
gggtgggggg agttgcttcc agg                                              23

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 414 gggtgggggga actttgcacc agg                                             23

<210> SEQ ID NO 415
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 415
gagggtgggg agtttactcc tgg                                              23

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 416
atgtgtgggg aatttgctcc agg                                              23

<210> SEQ ID NO 417
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 417
gggggcaggg agattgctcc tgg                                              23

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 418 gaggggagc agtttgctcc agg                                               23

<210> SEQ ID NO 419
<211> LENGTH: 23
<212> TYPE: DNA
<213> ORGANISM: Artificial Sequence
<220> FEATURE:

```
<223> OTHER INFORMATION: Description of Artificial Sequence: Synthetic
      VEGFA site 1_off_target_sequence

<400> SEQUENCE: 419
ggctggaggg gatttgctcc tgg                                              23

<210> SEQ ID NO 420
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 420
agctggaggg agtttgcccc agg                                              23

<210> SEQ ID NO 421
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 421
tagtggaggg agcttgctcc tgg                                              23

<210> SEQ ID NO 422
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 422 agtttgggggg agtttgcccc agg                                             23

<210> SEQ ID NO 423
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 423
gggaggaggg aatctgctcc agg                                              23

<210> SEQ ID NO 424
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 424
aggtggtggg agcttgttcc tgg                                              23

<210> SEQ ID NO 425
<211> LENGTH: 23
<212> TYPE: DNA
<213> ORGANISM: Artificial Sequence
<220> FEATURE:
<223> OTHER INFORMATION: Description of Artificial Sequence: Synthetic
```

VEGFA site 1_off_target_sequence

<400> SEQUENCE: 425
ggaggagggg agtctgctcc agg                                      23

<210> SEQ ID NO 426
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 426 ggtggggtg ggtttgctcc tgg                                       23

<210> SEQ ID NO 427
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 427
gggggtgggg agcatgctcc agg                                      23

<210> SEQ ID NO 428
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 428
gtgggggtag agtttgctcc agg                                      23

<210> SEQ ID NO 429
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 429
ggatggaggt agtttgttcc tgg                                      23

<210> SEQ ID NO 430
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 430 ttggggggc agtttgctcc tgg                                       23

<210> SEQ ID NO 431
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 431
gggcaagggg aggttgctcc tgg                                              23

<210> SEQ ID NO 432
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 432
gggggaggga agtttcctcc agg                                              23

<210> SEQ ID NO 433
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 433
aggtcggggg agttagatcc cgg                                              23

<210> SEQ ID NO 434
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 434
gggggtgggg ggtttgctcc tgc                                              23

<210> SEQ ID NO 435
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 435
gtgtgagtgg agtttgctct ggg                                              23

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 436
gggagcaggg aatttgctcc agg                                              23

<210> SEQ ID NO 437
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

```
<400> SEQUENCE: 437 ggagggggggg cttttgctcc agg                                          23

<210> SEQ ID NO 438
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 438
aggtttgggg agtttgctac agg                                           23

<210> SEQ ID NO 439
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 439
tgctcggggg agtttgcacc agg                                           23

<210> SEQ ID NO 440
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 440 gggggggggtg ggtttgctct ggg                                          23

<210> SEQ ID NO 441
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 441
cagtgggggg agctttctcc tgg                                           23

<210> SEQ ID NO 442
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 442
tggagagggg agttggctcc tgg                                           23

<210> SEQ ID NO 443
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 443
```
tggtgggagg tgtttgatcc tgg                                              23

<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 444
ggggaggggg agatggctcc cgg                                              23

<210> SEQ ID NO 445
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 445
ggatggggag agtttgcatc tgg                                              23

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 446
gggtcagggg agttatctcc tgg                                              23

<210> SEQ ID NO 447
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 447
ggggtggggg agagtgctcc agg                                              23

<210> SEQ ID NO 448
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 448
gggagtgagg actttgctcc tgg                                              23

<210> SEQ ID NO 449
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 449
gggagggaag agttcgctcc agg                                                   23

<210> SEQ ID NO 450
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 450
gagtgggagg agtttgtccc agg                                                   23

<210> SEQ ID NO 451
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 451
cggtggggtg aatttgctcc cag                                                   23

<210> SEQ ID NO 452
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 452
ggggaggggg agggtgctcc agg                                                   23

<210> SEQ ID NO 453
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 453
gggatgggag agtctgctcc tgg                                                   23

<210> SEQ ID NO 454
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 454
gagggcgggg agtttgctac tgg                                                   23

<210> SEQ ID NO 455
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 455
ggggtggggg tgtttgctct ggg                                                   23

-continued

```
<210> SEQ ID NO 456
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 456
gggtcagggg agttatctcc tgg                                              23

<210> SEQ ID NO 457
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 457
tggtggggag gggttgctcc cgg                                              23

<210> SEQ ID NO 458
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 458
gggtggggat agtttacacc cgg                                              23

<210> SEQ ID NO 459
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 459
gggggtgggg agttagctca tgg                                              23

<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 460
gggggtgggg aggttgcccc agg                                              23

<210> SEQ ID NO 461
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 461
agctgggggg actttgcttc tgg                                              23
```

<210> SEQ ID NO 462
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 462
ggctgagggg agtctgttcc ggg                                               23

<210> SEQ ID NO 463
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 463
ggttggtggg gctttgctcc agg                                               23

<210> SEQ ID NO 464
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 464
gggtcagggg aggatgctcc tgg                                               23

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 465
gggtgaatgg agttggctcc tgg                                               23

<210> SEQ ID NO 466
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 466
gagttggggg actatgctcc tgg                                               23

<210> SEQ ID NO 467
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 467
gggcaggggg agactgctcc tgg                                               23

-continued

<210> SEQ ID NO 468
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 468
gagtgggagg agttagctca tgg                                              23

<210> SEQ ID NO 469
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 469
agttgggggg aggttgctct agg                                              23

<210> SEQ ID NO 470
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 470
gtgagggggg agtttgcctc tgg                                              23

<210> SEQ ID NO 471
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 471
ggttggtgga agttagctcc tgg                                              23

<210> SEQ ID NO 472
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 472
gggtgtgggg tcattgctcc agg                                              23

<210> SEQ ID NO 473
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 473
gggtagggag tgtttgctca agg                                              23

<210> SEQ ID NO 474

```
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 474
gggggggggg ggtctgctcc cag                                              23

<210> SEQ ID NO 475
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 475
gggaggggca ggtttgctcc ggg                                              23

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 476
ggtttgyggg tgtttgatcc tgg                                              23

<210> SEQ ID NO 477
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 477
gggaaggggg cgttttctcc tgg                                              23

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 478
ggatgagggg actctgctcc tgg                                              23

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 479
gggtgggaga agtctgctcc cag                                              23

<210> SEQ ID NO 480
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 480
aggtgggtgg agtttgctgc ctg                                          23

<210> SEQ ID NO 481
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 481
gggtggggac agttagctcc ctg                                          23

<210> SEQ ID NO 482
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 482 ggggagggg ggtgtgctcc agg                                           23

<210> SEQ ID NO 483
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 483
ggatgggagg aggttggtcc agg                                          23

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 484
ggatgggagg agtattctcc agg                                          23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 485
gggcggggag cgtttgcacc cgg                                          23

<210> SEQ ID NO 486
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 486
agggaggagg aatttgctcc agg                                              23

<210> SEQ ID NO 487
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 487
agggagggag aatttgctcc tgg                                              23

<210> SEQ ID NO 488
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 488
gggtgaaaga agtttactcc tgg                                              23

<210> SEQ ID NO 489
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 489
aagtaaggga agtttgctcc tgg                                              23

<210> SEQ ID NO 490
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 490
ctctgagggg agtttgctct ggg                                              23

<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 491
aggaaggagg agttagctcc tgg                                              23

<210> SEQ ID NO 492
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      VEGFA site 1_off_target_sequence

<400> SEQUENCE: 492
ggagtgggtg agcttgctcc tgg                                              23

<210> SEQ ID NO 493
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 493
aggcagaggg agattgctcc agg                                              23

<210> SEQ ID NO 494
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 494
tcctgagggc agtttgctcc agg                                              23

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 495
ggtatggggg agcttgctct agg                                              23

<210> SEQ ID NO 496
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 496
aggaaggagg agttagctcc tgg                                              23

<210> SEQ ID NO 497
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 497
ggtggagggg acattgctcc agg                                              23

<210> SEQ ID NO 498
<211> LENGTH: 23
<212> TYPE: DNA
<213> ORGANISM: Artificial Sequence
<220> FEATURE:
```

<223> OTHER INFORMATION: Description of Artificial Sequence: Synthetic
      VEGFA site 1_off_target_sequence

<400> SEQUENCE: 498
ggtgggggag agctagctcc ggg                                           23

<210> SEQ ID NO 499
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 499
aggaaggagg agttagctcc tgg                                           23

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 500
aggaaggagg agttagctcc tgg                                           23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 501
gagatggggg agtatgcacc agg                                           23

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 502
aggaggggga agaatgctcc agg                                           23

<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 503
aagtgggaag agtttgttcc agg                                           23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic VEGFA site 1_off_target_sequence

<400> SEQUENCE: 504
ggaaaggagg agcttgctcc agg                                         23

<210> SEQ ID NO 505
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 505
agttaggggg agtttattcc agg                                         23

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 506
gtatggggga agtgtgctcc agg                                         23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 507
aggagggagg aagttgctcc agg                                         23

<210> SEQ ID NO 508
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 508
agctgagggg agcttgctct ggg                                         23

<210> SEQ ID NO 509
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 509
tcgtggtggg aatttactcc tgg                                         23

<210> SEQ ID NO 510
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

```
<400> SEQUENCE: 510
gtgcaggggg aatttgcttc cgg                                              23

<210> SEQ ID NO 511
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 511
tggggagggg aaattgctcc tgg                                              23

<210> SEQ ID NO 512
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 512
gagtgaggag agcttgctcc atg                                              23

<210> SEQ ID NO 513
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 513
aagtgggagg agactgctcc agg                                              23

<210> SEQ ID NO 514
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 514
tcttgggggg aagttgctcc agg                                              23

<210> SEQ ID NO 515
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 515
ggggtagagg agtttgcgcc agg                                              23

<210> SEQ ID NO 516
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence
```

```
<400> SEQUENCE: 516
gggggtgggg agcaagctcc tgg                                              23

<210> SEQ ID NO 517
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 517
aagtgggaag tgtttgctcc tgg                                              23

<210> SEQ ID NO 518
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 518
aggggtaggg agattgctcc tgg                                              23

<210> SEQ ID NO 519
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 519
aggtggaggg gatttgttcc agg                                              23

<210> SEQ ID NO 520
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 520
aagtggagtg agtttgctct ggg                                              23

<210> SEQ ID NO 521
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 521
ggtggggtgt ggtttgctcc agg                                              23

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 522
```
aggtacgggg agcatgctcc agg                                              23

<210> SEQ ID NO 523
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 523
agatgggtga agtttgcttc tgg                                              23

<210> SEQ ID NO 524
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 524
ggaggaggga actttgctcc agg                                              23

<210> SEQ ID NO 525
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 525 gagggaagg agtttgctca agg                                              23

<210> SEQ ID NO 526
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 526
agataggggc agtttgcttc tgg                                              23

<210> SEQ ID NO 527
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 527
ggaggggagg gctttgctcc agg                                              23

<210> SEQ ID NO 528
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 528
ttgtaggtgg agttagctcc agg 23

<210> SEQ ID NO 529
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 529
aaatgggggg agtttgcccc ccg 23

<210> SEQ ID NO 530
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 530
gggcagaggg agttagcacc ggg 23

<210> SEQ ID NO 531
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 531
gggggagggg agaatgcccc agg 23

<210> SEQ ID NO 532
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 532
ggaagagggg agtttgaacc agg 23

<210> SEQ ID NO 533
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 533
gagtgagcag agtttgctcc tgc 23

<210> SEQ ID NO 534
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 534
ctttggggtt agtttgctcc tgg 23

```
<210> SEQ ID NO 535
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 535
ggtgggggaa agtttgctcc tga                                              23

<210> SEQ ID NO 536
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 536 tggggggag agattgcttc cgg                                               23

<210> SEQ ID NO 537
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 537
agataggggt agtttgctac agg                                              23

<210> SEQ ID NO 538
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 538
gaggggcagg aatttgctcc agg                                              23

<210> SEQ ID NO 539
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 539
agggtggggc cgtttgctcc cgg                                              23

<210> SEQ ID NO 540
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 540
gtgtggtagg aggttgctct ggg                                              23
```

<210> SEQ ID NO 541
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 541
cagtggaggg actttgttcc agg                                           23

<210> SEQ ID NO 542
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 542
ggagggaggg agattgctct agg                                           23

<210> SEQ ID NO 543
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 543
gtgtgagggg agtaagctct agg                                           23

<210> SEQ ID NO 544
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 544
gggcaggagg agtcagctcc agg                                           23

<210> SEQ ID NO 545
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 545
gggaaggagg gctttgctcc ggg                                           23

<210> SEQ ID NO 546
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 546
aagaggggag agtttgctcc ctg                                           23

```
<210> SEQ ID NO 547
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 547 ggtaggggggg aaattgcccc tgg                                              23

<210> SEQ ID NO 548
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 548
ggggatgggg agtttactcc cag                                               23

<210> SEQ ID NO 549
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 549
aagtgagtgg cgtttgctcc tgg                                               23

<210> SEQ ID NO 550
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 550
acgtgaggtc agtttgctcc tgg                                               23

<210> SEQ ID NO 551
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 551
ctttcggggg agtttgcgcc ggg                                               23

<210> SEQ ID NO 552
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 552
gggagggagg ggcttgcccc agg                                               23

<210> SEQ ID NO 553
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 553 tgggaggggga agtttgcacc agg                                          23

<210> SEQ ID NO 554
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 554
aagtgagtgg agtttgctcc tgc                                           23

<210> SEQ ID NO 555
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 555
agatggagga agtttgctcc agc                                           23

<210> SEQ ID NO 556
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 556
aggcaggggg agtttactca agg                                           23

<210> SEQ ID NO 557
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 557
tggaggggag agtttgttca ggg                                           23

<210> SEQ ID NO 558
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 558
gaggggaggg agcttcctcc cgg                                           23

<210> SEQ ID NO 559
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 559
aaatgggggg agattgctct tgg                                              23

<210> SEQ ID NO 560
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 560
gggtagatgg agcttgatcc agg                                              23

<210> SEQ ID NO 561
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 561
gggtcgggga gacttgctcc agg                                              23

<210> SEQ ID NO 562
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 562
aggagagggg agtctgttcc agg                                              23

<210> SEQ ID NO 563
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 563
gggggtgggg gatttgctcc cag                                              23

<210> SEQ ID NO 564
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 564
gggggcaggg agcatgctcc agg                                              23

<210> SEQ ID NO 565
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 565 ggaggggggga agattgcttc tgg                                            23

<210> SEQ ID NO 566
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 566
gactgggggg agtttgcttc ctg                                             23

<210> SEQ ID NO 567
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 567
ggaagagggg agtttgctcc cca                                             23

<210> SEQ ID NO 568
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 568
atgtgggggg aatttaatcc agg                                             23

<210> SEQ ID NO 569
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 569
aggtgtgagg acttagctcc cgg                                             23

<210> SEQ ID NO 570
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 570
gggtgagggg aataaactcc agg                                             23

<210> SEQ ID NO 571
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      VEGFA site 1_off_target_sequence

<400> SEQUENCE: 571 gggggggagga agagtgctcc agg                                               23

<210> SEQ ID NO 572
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 572
gtgaggggag aaattgctcc agg                                                23

<210> SEQ ID NO 573
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 573
ggatgggagt gatttgctcc agg                                                23

<210> SEQ ID NO 574
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 574
aggggtgggg tgtttgttcc agg                                                23

<210> SEQ ID NO 575
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 575
gagaggggag agcttgctca agg                                                23

<210> SEQ ID NO 576
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 576 tgggggtgg agcttgcacc tgg                                                 23

<210> SEQ ID NO 577
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      VEGFA site 1_off_target_sequence

<400> SEQUENCE: 577
aggagggagg aggatgctcc agg                                          23

<210> SEQ ID NO 578
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 578
aggtgcgagg ggtttgcacc tgg                                          23

<210> SEQ ID NO 579
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 579
agatgggggg atgttgctcc aag                                          23

<210> SEQ ID NO 580
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 580
agatggagga agtttgctcc agc                                          23

<210> SEQ ID NO 581
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 581
aggggagggg aggttgctac tgg                                          23

<210> SEQ ID NO 582
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 582
agctggaggg agtttgcctc agg                                          23

<210> SEQ ID NO 583
<211> LENGTH: 23
<212> TYPE: DNA
<213> ORGANISM: Artificial Sequence
<220> FEATURE:
<223> OTHER INFORMATION: Description of Artificial Sequence: Synthetic
```

-continued

VEGFA site 1_off_target_sequence

<400> SEQUENCE: 583
cagtgggcag agtttgcccc agg                                        23

<210> SEQ ID NO 584
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 584
ggggcgggga agcttgcttc cgg                                        23

<210> SEQ ID NO 585
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 585
ggtggggacc agtttgctcc agg                                        23

<210> SEQ ID NO 586
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 586
aggaggggag agtatgctac cgg                                        23

<210> SEQ ID NO 587
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 587
gagaggaggc agtttgcccc agg                                        23

<210> SEQ ID NO 588
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 588
gagtggtggg aattagttcc tgg                                        23

<210> SEQ ID NO 589
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

```
<400> SEQUENCE: 589 cgggggagg ggtttgctca agg                                          23

<210> SEQ ID NO 590
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 590
gagtaagtgg agattgctcc agg                                         23

<210> SEQ ID NO 591
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 591
agatgtgggg agagtgctcc agg                                         23

<210> SEQ ID NO 592
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 592
gtggggaggg ggtttgctac tgg                                         23

<210> SEQ ID NO 593
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 593
aagttggggg agtatgctac tgg                                         23

<210> SEQ ID NO 594
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 594
ggatggagtg agtgggctcc ggg                                         23

<210> SEQ ID NO 595
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence
```

```
<400> SEQUENCE: 595
gggaggggag agaatactcc agg                                              23

<210> SEQ ID NO 596
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 596 gtgggggtg attttgcccc cgg                                               23

<210> SEQ ID NO 597
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 597
gtgtggggta aatttgctcc cag                                              23

<210> SEQ ID NO 598
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 598
gaatggggag agtgtgctcc agg                                              23

<210> SEQ ID NO 599
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 599
gagtgagtgg agtttgatcc cgc                                              23

<210> SEQ ID NO 600
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 600
tagtggggat attttgctcc tgg                                              23

<210> SEQ ID NO 601
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 601
```
gagggggggg agtcagcccc cgg                                           23

<210> SEQ ID NO 602
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 602
ctgtgggggg accttgctcc cag                                           23

<210> SEQ ID NO 603
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 603
gggtgcgtgg ggtgtgctct ggg                                           23

<210> SEQ ID NO 604
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 604
gaggtgggcg agtttgcttc agg                                           23

<210> SEQ ID NO 605
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 605
tggttcaggg agtttgctct ggg                                           23

<210> SEQ ID NO 606
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 606
ggctgaaggg agtttgcttt agg                                           23

<210> SEQ ID NO 607
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 607
aggtgggagg agcttgaacc tgg                                            23

<210> SEQ ID NO 608
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 608
acttgggggg aggttgctac tgg                                            23

<210> SEQ ID NO 609
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 609
ggaagggagg agagtgctcc agg                                            23

<210> SEQ ID NO 610
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 610
gggtggggga aattcgcagc agg                                            23

<210> SEQ ID NO 611
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 611
gagtgggaag agtatgctcc cag                                            23

<210> SEQ ID NO 612
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 612
aggaggtgga aatttgctcc agg                                            23

<210> SEQ ID NO 613
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 613 gggtgggag agcttgcaga cgg                                             23

<210> SEQ ID NO 614
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 614
ggtggagggg agtttgcaca tgg                                              23

<210> SEQ ID NO 615
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 615
gagggagggg agtctgctcc cag                                              23

<210> SEQ ID NO 616
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 616
gggtaagggg gatctgctcc tgg                                              23

<210> SEQ ID NO 617
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 617
gggggagggg agaatgcccc agg                                              23

<210> SEQ ID NO 618
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 618
aggagagcgg agttggctcc tgg                                              23

<210> SEQ ID NO 619
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 619
aggtggggag gtttagctcc tgg                                              23

<210> SEQ ID NO 620
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 620
agtttggggg aaattgctcc agg                                              23

<210> SEQ ID NO 621
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 621
ttgtggagaa agtttgctcc tgg                                              23

<210> SEQ ID NO 622
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 622
tggggagggg agtttgcctc tgg                                              23

<210> SEQ ID NO 623
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 623
gggtgaggga agaatgttcc agg                                              23

<210> SEQ ID NO 624
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 624
ggaaggaggg agtttgctta agg                                              23

<210> SEQ ID NO 625
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 625 ggaggggggag agattgcttc tgg                                             23

```
<210> SEQ ID NO 626
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 626
cggtggggtg agaaagctcc tgg                                              23

<210> SEQ ID NO 627
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 627
agttaggggg agtttattcc agg                                              23

<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 628
ggtagggggg tatctgctcc agg                                              23

<210> SEQ ID NO 629
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 629
ggccagaggg agtttgctca ggg                                              23

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 630
gggtgggagg agtttgccca cag                                              23

<210> SEQ ID NO 631
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 631
aggaaggggg attctgctcc ggg                                              23

<210> SEQ ID NO 632
```

<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 632
gggaggagag agtttgctct ctg                                           23

<210> SEQ ID NO 633
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 633
ctggtggggg agcttgctcc agg                                           23

<210> SEQ ID NO 634
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 634
agtgggggag agtatgctcc ggg                                           23

<210> SEQ ID NO 635
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 635
tggggagggg agaaagctcc tgg                                           23

<210> SEQ ID NO 636
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 636
cccgggggga agcttgctcc agg                                           23

<210> SEQ ID NO 637
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 637
gagttggggg aatttgctct ctg                                           23

<210> SEQ ID NO 638
<211> LENGTH: 23

```
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 638
agggagaggg agcttgctcc cag                                          23

<210> SEQ ID NO 639
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 639
agaggggtgg agtttgttcc agg                                          23

<210> SEQ ID NO 640
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 640
aaagggggga actttgctcc agg                                          23

<210> SEQ ID NO 641
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 641 gtagggggc agtttgctcc cag                                           23

<210> SEQ ID NO 642
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 642
agggaagggg aatttgcacc tgg                                          23

<210> SEQ ID NO 643
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 643
gggtagaggg ggcttgtacc cgg                                          23

<210> SEQ ID NO 644
<211> LENGTH: 23
<212> TYPE: DNA
```

-continued

```
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 644 agaggggag agtttgcccc tgg                                              23

<210> SEQ ID NO 645
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 645
gagtagaggg agttaaatcc agg                                             23

<210> SEQ ID NO 646
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 646
aagtggaagg agcttgcacc agg                                             23

<210> SEQ ID NO 647
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 647
aggggaggga acattgctcc agg                                             23

<210> SEQ ID NO 648
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 648
gagtagaggg agttaaatcc agg                                             23

<210> SEQ ID NO 649
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 649
gaaagagggg agtttgcttc tgg                                             23

<210> SEQ ID NO 650
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      VEGFA site 1_off_target_sequence

<400> SEQUENCE: 650
ccttggaggg agtttattcc tgg                                              23

<210> SEQ ID NO 651
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 651
ggggtgggag agtttgctct ctg                                              23

<210> SEQ ID NO 652
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 652
agggtggagg agcatgctcc agg                                              23

<210> SEQ ID NO 653
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 653
ggagaggagg agttaactcc agg                                              23

<210> SEQ ID NO 654
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 654
agaagagggg attttgctcc tgg                                              23

<210> SEQ ID NO 655
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 655
ctgggagggg agcttgttcc tgg                                              23

<210> SEQ ID NO 656
<211> LENGTH: 23
<212> TYPE: DNA
<213> ORGANISM: Artificial Sequence
<220> FEATURE:
```

<223> OTHER INFORMATION: Description of Artificial Sequence: Synthetic
      VEGFA site 1_off_target_sequence

<400> SEQUENCE: 656
aggtaggaga agcttgctcc tga                                            23

<210> SEQ ID NO 657
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 657
atggggaggg ggtttgctcc cag                                            23

<210> SEQ ID NO 658
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 658
gagggagagg agtttactcc cag                                            23

<210> SEQ ID NO 659
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 659
agggtgagga agtttgctcg ggg                                            23

<210> SEQ ID NO 660
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 660
ggagaggagg agttagcacc ggg                                            23

<210> SEQ ID NO 661
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 661
aagtgggaga agcttgctct ggg                                            23

<210> SEQ ID NO 662
<211> LENGTH: 23
<212> TYPE: DNA
<213> ORGANISM: Artificial Sequence
<220> FEATURE:
<223> OTHER INFORMATION: Description of Artificial Sequence: Synthetic VEGFA site 1_off_target_sequence

<400> SEQUENCE: 662
aggaggaggg agtccgttcc ggg                                              23

<210> SEQ ID NO 663
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 663
aggcaggagg agaatgctcc agg                                              23

<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 664
gtgggaggat agcttgctcc tgg                                              23

<210> SEQ ID NO 665
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 665
gcttgagggg aatttgcttc agg                                              23

<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 666
ggtggggaga atcttgctcc agg                                              23

<210> SEQ ID NO 667
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 667 tttgggggggg atcttgctcc tgg                                             23

<210> SEQ ID NO 668
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence -continued

<400> SEQUENCE: 668
tcatgagggg actttgccccc agg                                             23

<210> SEQ ID NO 669
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 669
aagggagggg agcttgctcc aga                                              23

<210> SEQ ID NO 670
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 670 tcatggggggc agtttcccccc agg                                            23

<210> SEQ ID NO 671
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 671
gaattgggga agtttgcacc agg                                              23

<210> SEQ ID NO 672
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 672
ggtggaggtg ggtttgctcc gag                                              23

<210> SEQ ID NO 673
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 673
agggtgggtg agattactcc tgg                                              23

<210> SEQ ID NO 674
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

```
<400> SEQUENCE: 674
tcttggggag aattagctcc tgg                                            23

<210> SEQ ID NO 675
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 675 gtgggggat agcttgatcc ggg                                             23

<210> SEQ ID NO 676
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 676 ccttgggga aatttgttcc agg                                             23

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 677
tgtggggggg actttgcccc ggg                                            23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 678
aggcaggaag agtttgctca ggg                                            23

<210> SEQ ID NO 679
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 679
ttctgagggg agattgcccc tgg                                            23

<210> SEQ ID NO 680
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 680
```
ggaaaggagg agcttgctcc gag          23

<210> SEQ ID NO 681
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 681
gggaaagagg agcttgttcc tgg          23

<210> SEQ ID NO 682
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 682
gagcaggaga agcttgctcc ggg          23

<210> SEQ ID NO 683
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 683
agatggaagg agcttgctcg ggg          23

<210> SEQ ID NO 684
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 684
tattggggtg aatgtgctcc tgg          23

<210> SEQ ID NO 685
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 685 gaggggagg agtaagctcc tag          23

<210> SEQ ID NO 686
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 686
ggtggaaggc agtttgctcc tag                                          23

<210> SEQ ID NO 687
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 687
ctgtgggagg agattacacc agg                                          23

<210> SEQ ID NO 688
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 688
cacggagggg tgtttgctcc tgg                                          23

<210> SEQ ID NO 689
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 689
aggggagggg aacttgcacc agg                                          23

<210> SEQ ID NO 690
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 690
gagggagggg aacttgctca ggg                                          23

<210> SEQ ID NO 691
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 691
aagtgagtag agtttgctcc tgc                                          23

<210> SEQ ID NO 692
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 692
tgacgggggg agtttgctct ggt                                          23

<210> SEQ ID NO 693
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 693
gaaacggggg agtttgctca ggg                                          23

<210> SEQ ID NO 694
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 694
gctctggggt agtttgctcc agg                                          23

<210> SEQ ID NO 695
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 695
cagtggaagg agattactcc agg                                          23

<210> SEQ ID NO 696
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 696
gaggagaggg agattgcccc cgg                                          23

<210> SEQ ID NO 697
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 697
ggagtgaggg agcttgctct agg                                          23

<210> SEQ ID NO 698
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 698
agggagggag agtttgttca ggg                                          23

```
<210> SEQ ID NO 699
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 699
ggtctgggga gctttgctcc agg                                                23

<210> SEQ ID NO 700
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 700
gtctggggga agtttgccca agg                                                23

<210> SEQ ID NO 701
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 701
atgaggggga agcttgttcc agg                                                23

<210> SEQ ID NO 702
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 702
gaggggaggg ggcttgcccc agg                                                23

<210> SEQ ID NO 703
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 703
cagtggggag aggaagctcc tgg                                                23

<210> SEQ ID NO 704
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 704
gtttgggagg agtttgtacc tgg                                                23
```

```
<210> SEQ ID NO 705
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 705
ctctgagggg aatttgctgc tgg                                              23

<210> SEQ ID NO 706
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 706
gggaaggagg agagagctcc tgg                                              23

<210> SEQ ID NO 707
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 707
ggggaggtgg agtttattcc cag                                              23

<210> SEQ ID NO 708
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 708
ggggtggggg gaaatgctcc agg                                              23

<210> SEQ ID NO 709
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 709
ggtggggaga agtttgcccc gag                                              23

<210> SEQ ID NO 710
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 710
ctctgagggc aatttgctcc cgg                                              23

<210> SEQ ID NO 711
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 711
ggagggaggg agcttgaacc agg                                              23

<210> SEQ ID NO 712
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 712
atctgggggg gatttgttcc agg                                              23

<210> SEQ ID NO 713
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 713 aggggtagg ggttagctcc tgg                                               23

<210> SEQ ID NO 714
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 714
ggatggaaag agtttgcacc aag                                              23

<210> SEQ ID NO 715
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 715
tggtagggga tgtaagctcc tgg                                              23

<210> SEQ ID NO 716
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 716
gcatgggagg agtctgcacc ggg                                              23

<210> SEQ ID NO 717
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 717
cactgggagg agtatgcacc ggg                                              23

<210> SEQ ID NO 718
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 718
ggagggaggg ggcttgctca tgg                                              23

<210> SEQ ID NO 719
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 719
gggaaagggg gatttactcc agg                                              23

<210> SEQ ID NO 720
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 720
ctgtggggga ggcttgcccc agg                                              23

<210> SEQ ID NO 721
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 721
ggtggtctgg agtttgcacc tgg                                              23

<210> SEQ ID NO 722
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 722
gagtggaagg gatttgctca agg                                              23

<210> SEQ ID NO 723
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 723
ggtgggagga agtatggtcc agg                                              23

<210> SEQ ID NO 724
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 724
aggaaagagg agtttgatcc tgg                                              23

<210> SEQ ID NO 725
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 725
acggtggggg aatttgctcc tga                                              23

<210> SEQ ID NO 726
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 726
caggtgggag agtttgctcc cag                                              23

<210> SEQ ID NO 727
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 727
aagtaaaggg agcttactcc tgg                                              23

<210> SEQ ID NO 728
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 728
agtgaagggg agtttgctcc tgc                                              23

<210> SEQ ID NO 729
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      VEGFA site 1_off_target_sequence

<400> SEQUENCE: 729
gcaaggggga gctttgctcc agg                                               23

<210> SEQ ID NO 730
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 730
aaggaggcgg agcttgctcc tgg                                               23

<210> SEQ ID NO 731
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 731 atgaaggga attttgctcc agg                                                23

<210> SEQ ID NO 732
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 732
gctggagggg aatttgcccc agg                                               23

<210> SEQ ID NO 733
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 733
aaggagggtg agcttgctcc agg                                               23

<210> SEQ ID NO 734
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 734
gcagtggggg ggtttgcccc agg                                               23

<210> SEQ ID NO 735
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      VEGFA site 1_off_target_sequence

<400> SEQUENCE: 735
aggtagggag agtttgccca cag                                             23

<210> SEQ ID NO 736
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 736
tctggagggg agaatgctcc agg                                             23

<210> SEQ ID NO 737
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 737 gcagggagg agtttgttcc gag                                              23

<210> SEQ ID NO 738
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 738
aaaaaggggg aatttactcc ggg                                             23

<210> SEQ ID NO 739
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 739
cctgcggggg agcttgcccc agg                                             23

<210> SEQ ID NO 740
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 740
tctgggggga agttaactcc agg                                             23

<210> SEQ ID NO 741
<211> LENGTH: 23
<212> TYPE: DNA
<213> ORGANISM: Artificial Sequence
<220> FEATURE:
<223> OTHER INFORMATION: Description of Artificial Sequence: Synthetic
```

VEGFA site 1_off_target_sequence

<400> SEQUENCE: 741
gggggagggg catttgctct aag                                              23

<210> SEQ ID NO 742
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 742
agaaggaggg agaatgctcc agg                                              23

<210> SEQ ID NO 743
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 743
gaatgaggga agaatgctcc tgg                                              23

<210> SEQ ID NO 744
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 744
agggagggcg agtttgctca ctg                                              23

<210> SEQ ID NO 745
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 745
gaatgaggag agcttgcacc tgg                                              23

<210> SEQ ID NO 746
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 746
gtatgagggg aaatagctcc tgg                                              23

<210> SEQ ID NO 747
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence -continued

<400> SEQUENCE: 747
ttgaagggga agtttgctct ggg                                              23

<210> SEQ ID NO 748
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 748
agaagggagg aatttgctcc ctg                                              23

<210> SEQ ID NO 749
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 749
gggtgggggg tggtccacac agg                                              23

<210> SEQ ID NO 750
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 750
gggaggtggc agcttgagcc aga                                              23

<210> SEQ ID NO 751
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 751
agtgggggga agagtgctcc ggg                                              23

<210> SEQ ID NO 752
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 752
aggtggggga aggctagtca tgg                                              23

<210> SEQ ID NO 753
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 753 aacctgggggg ggcttgctcc tgg                                              23

<210> SEQ ID NO 754
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 754
agggtgagga ggcttgctcc tgg                                               23

<210> SEQ ID NO 755
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 755
tggtgggagg tgattgcgtc atg                                               23

<210> SEQ ID NO 756
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 756
gggtgacgag agatgcctcc cag                                               23

<210> SEQ ID NO 757
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 757 atagtgggggg agtttgttct ggg                                              23

<210> SEQ ID NO 758
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 758
agatgggagg attttattcc atg                                               23

<210> SEQ ID NO 759
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 759
tatagagggg aatttgctac tgg                                    23

<210> SEQ ID NO 760
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 760
gggtggtggg aggcagcatc tgt                                    23

<210> SEQ ID NO 761
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 761
tctgtgggga agattgctcc agg                                    23

<210> SEQ ID NO 762
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 762
agaaggaggg agctggctcc agg                                    23

<210> SEQ ID NO 763
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 763
cacctgggag agtttgctca ggg                                    23

<210> SEQ ID NO 764
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 764
tattggagga agagtgctcc agg                                    23

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 765

```
gggtgggggt ggggtgcttc t                                              21

<210> SEQ ID NO 766
<211> LENGTH: 23
<212> TYPE: DNA
<213> ORGANISM: Artificial Sequence
<220> FEATURE:
<223> OTHER INFORMATION: Description of Artificial Sequence: Synthetic
      VEGFA site 1_off_target_sequence

<400> SEQUENCE: 766
gaagtggggg tgttagctcc cgg                                            23
```